(12) United States Patent
Zhuang

(10) Patent No.: US 9,572,787 B2
(45) Date of Patent: Feb. 21, 2017

(54) INHIBITION OF RENAL FIBROSIS

(75) Inventor: Shougang Zhuang, Cheshire, CT (US)

(73) Assignee: Rhode Island Hospital, Providence, RI (US)

(*) Notice: Subject to any disclaimer, the term of this patent is extended or adjusted under 35 U.S.C. 154(b) by 145 days.

(21) Appl. No.: 14/117,728

(22) PCT Filed: May 21, 2012

(86) PCT No.: PCT/US2012/038799
§ 371 (c)(1),
(2), (4) Date: Nov. 14, 2013

(87) PCT Pub. No.: WO2012/159107
PCT Pub. Date: Nov. 22, 2012

(65) Prior Publication Data
US 2014/0088191 A1 Mar. 27, 2014

Related U.S. Application Data

(60) Provisional application No. 61/487,871, filed on May 19, 2011.

(51) Int. Cl.
*A61K 31/185* (2006.01)
*A61P 13/12* (2006.01)
*A61K 31/255* (2006.01)

(52) U.S. Cl.
CPC .................................. *A61K 31/255* (2013.01)

(58) Field of Classification Search
CPC ............................ A61K 31/255; A61K 31/185
USPC ........................................ 514/576, 577, 709
See application file for complete search history.

(56) References Cited

U.S. PATENT DOCUMENTS

| | | | |
|---|---|---|---|
| 5,223,242 A | 6/1993 | Khaw et al. | |
| 5,482,698 A | 1/1996 | Griffiths | |
| 5,525,338 A | 6/1996 | Goldenberg | |
| 5,620,675 A | 4/1997 | McBride et al. | |
| 5,690,907 A | 11/1997 | Lanza et al. | |
| 5,763,263 A | 6/1998 | Dehlinger | |
| 5,870,010 A | 2/1999 | Ackermann | |
| 5,958,371 A | 9/1999 | Lanza et al. | |
| 5,989,520 A | 11/1999 | Lanza et al. | |
| 6,083,486 A | 7/2000 | Weissleder et al. | |
| 6,676,926 B2 | 1/2004 | Hilger et al. | |
| 6,737,247 B2 | 5/2004 | Bogdanov et al. | |
| 8,633,250 B2 * | 1/2014 | Schnellmann | A61K 31/185 514/576 |
| 2011/0034559 A1 | 2/2011 | Schnellmann | |

FOREIGN PATENT DOCUMENTS

| EP | 0486809 A2 | 5/1992 |
|---|---|---|
| WO | WO-2009059425 A1 | 5/2009 |

OTHER PUBLICATIONS

Definition of prevent, Princeton University "About WordNet." WordNet. Princeton University. 2010. <http://wordnet.princeton.edu> accessed Sep. 18, 2012.*
Hildebrandt Lancet 2010, 375 (9722), 1287-1295.*
Ullmann et al. J. Med. Chem. 2005, 48, 7040-7048.*
Venkatachalam et al. Am. J. Physiol. Renal Physiol. 2010, 298, F1078-F1094.*
Chan et al. The American Journal of Sports and Medicine 2005, 33 (1), 43-51.*
Gagliardini et al. Expert Opinion on Biological Therapy 2007, 7 (3), 293-304.*
Guo et al. Am. J. Psysiol. Renal Physiol. 2001, 280, F777-F785.*
Silverstein Pediatr. Nephrol. 2009, 24, 1445-1452.*
Bundgaard. "Design of Prodrugs: Bioreversible Derivatives for Various Functional Groups and Chemical Entities." *Design of Prodrugs*. Bundgaard, ed. New York: Elsevier. (1985):1-92.
Katocs et al. "Biological Testing." *Remington's Pharmaceutical Sciences*. Gennaro, ed. Easton, PA: Mack Publishing Co. 18th ed. Chapter 27(1990):484-494.
Liu et al. "Suramin Inhibits Renal Fibrosis in Chronic Kidney Disease." *J. Am. Soc. Nephrol*. 22.6(2011):1064-1075.
Nakajima et al. "A Central Role for Stat3 in IL-6-Induced Regulation of Growth and Differentiation in M1 Leukemia Cells." *EMBO J*. 15.14(1996):3651-3658.
Nies et al. "Principles of Therapuetics." *Goodman & Gilman's The Pharmacological Basis of Therapeutics*. Hardman et al., eds. New York: McGraw-Hill. 9th ed. Chapter 3(1996):43-62.
Pang et al. "A Novel STAT3 Inhibitor, S3I-201, Attenuates Renal Interstitial Fibroblast Activation and Interstitial Fibrosis in Obstructive Nephropathy." *Kidney Int*. 78.3(2010):257-268.
Pietra et al. "Highly Conserved Amino-Acid Sequence Between Murine STAT3 and a Revised Human STAT3 Sequence." *Gene*. 213.1-2(1998):119-124.
Turkson et al. "Phosphotyrosyl Peptides Block Stat3-mediated DNA Binding Activity, Gene Regulation, and Cell Transformation." *J. Biol. Chem*. 276.48(2001):45443-45455.
Wang et al. "Regulation of the Innate and Adaptive Immune Responses by Stat-3 Signaling in Tumor Cells." *Nat. Med*. 10.1(2004):48-54.
Zhuang et al. "Suramin Promotes Recovery from Renal Ischemia/Reperfusion Injury in Mice." *Kidney Int*. 75.3(2009):304-311.
Chamberlain et al., The effect of suramin on healing adult rodent dermal wounds. J Anat. Feb. 1995;186 ( Pt 1):87-96.
Chan et al., Antifibrotic effects of suramin in injured skeletal muscle after laceration. J Appl Physiol; (1985). Aug. 2003;95(2):771-80.
Dreicer et al., Phase II trial of suramin in patients with metastatic renal cell carcinoma. Invest New Drugs. 1999;17(2):183-6.
Goldberg et al., Long-term outcomes of acute kidney injury. Adv Chronic Kidney Dis. Jul. 2008;15(3):297-307.
Haberstroh et al., TGF-beta stimulates rat mesangial cell proliferation in culture: role of PDGF beta-receptor expression. Am J Physiol. Feb. 1993;264(2 Pt 2):F199-205.
Li et al., Involvement of sphingosine 1-phosphate (SIP)/S1P3 signaling in cholestasis-induced liver fibrosis. Am J Pathol. Oct. 2009;175(4):1464-72.
Liu et al., Delayed administration of suramin attenuates the progression of renal fibrosis in obstructive nephropathy. J Pharmacol Exp Ther. Sep. 2011;338(3):758-66.

(Continued)

Primary Examiner — Sreeni Padmanabhan
Assistant Examiner — Irina Neagu
(74) Attorney, Agent, or Firm — Mintz Levin Cohn Ferris Glovsky and Popeo, P.C.; Ingrid A. Beattie

(57) ABSTRACT

The invention provides compositions and methods for inhibiting renal fibrosis.

19 Claims, 41 Drawing Sheets

(56) References Cited

OTHER PUBLICATIONS

Motzer et al., Phase II trial of suramin in patients with advanced renal cell carcinoma: treatment results, pharmacokinetics, and tumor growth factor expression. Cancer Res. Oct. 15, 1992;52(20):5775-9.
Smith et al., Acute renal failure in a patient receiving treatment with suramin. Am J Clin Oncol. Aug. 1997;20(4):433-4.
Stein et al., Suramin: an anticancer drug with a unique mechanism of action. J Clin Oncol. Apr. 1989;7(4):499-508.
Taniguti et al., Prevention of muscle fibrosis and myonecrosis in mdx mice by suramin, a TGF-β1 blocker. Muscle Nerve. Jan. 2011;43(1):82-7.
Turner et al., Antagonism of endogenous putative P2Y receptors reduces the growth of MDCK-derived cysts cultured in vitro. Am J Physiol Renal Physiol. Jan. 2007;292(1):F15-25.
Zhuang et al., Suramin promotes proliferation and scattering of renal epithelial cells. J Pharmacol Exp Ther. Jul. 2005;314(1):383-90.

\* cited by examiner

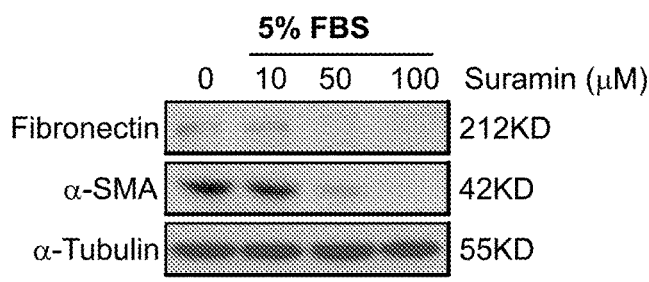
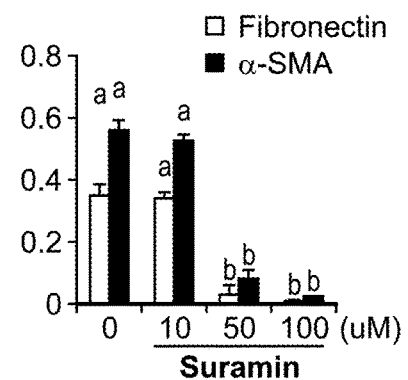
FIG. 13A
FIG. 13B
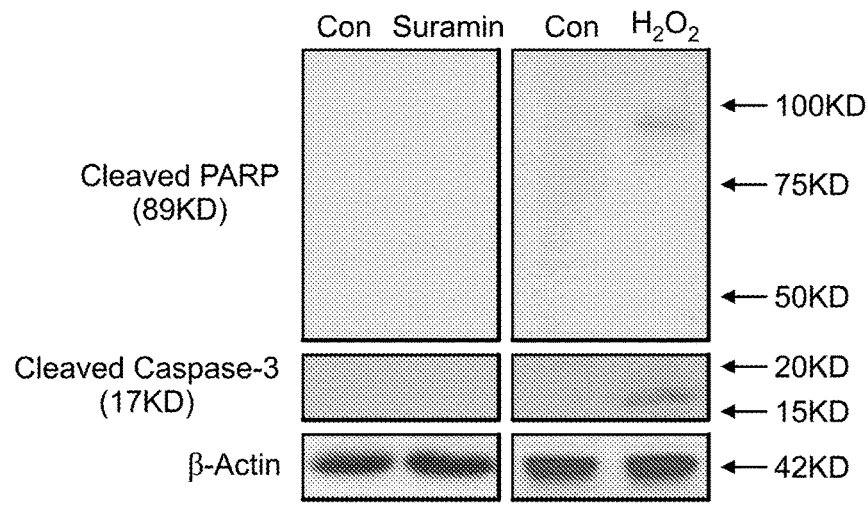
FIG. 13C

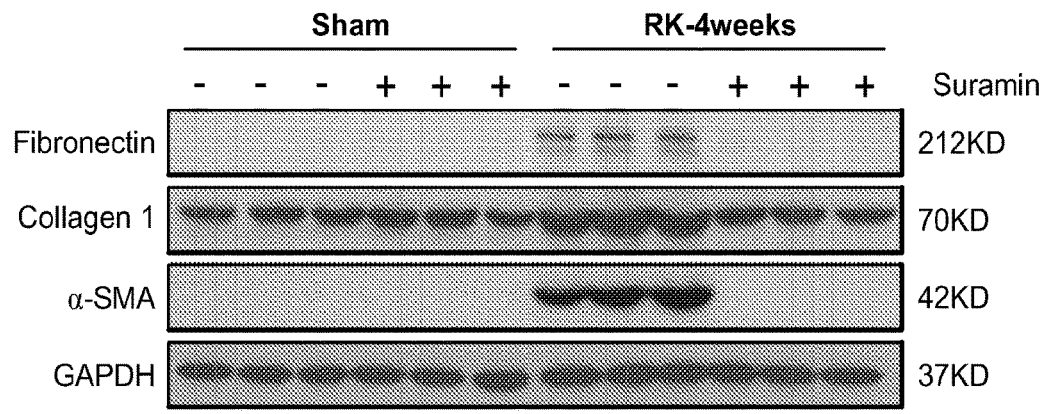
FIG. 17A
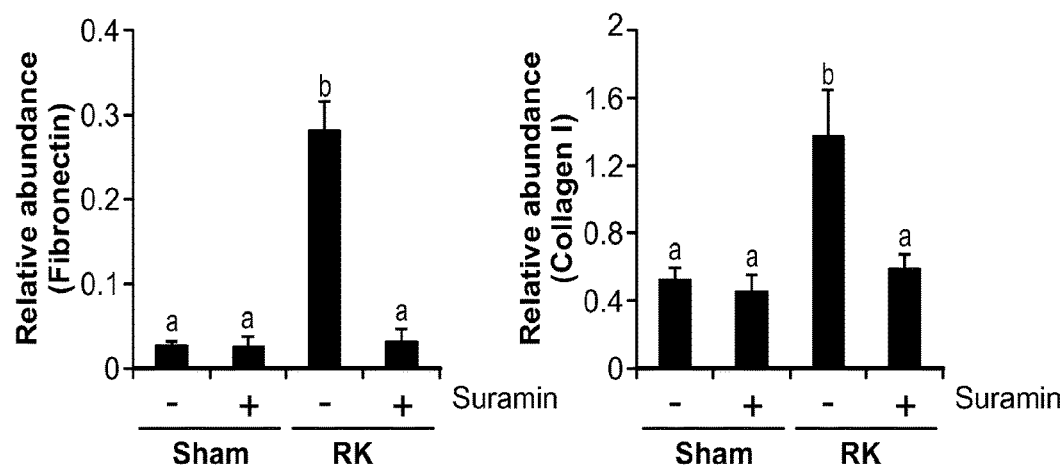
FIG. 17B
FIG. 17C

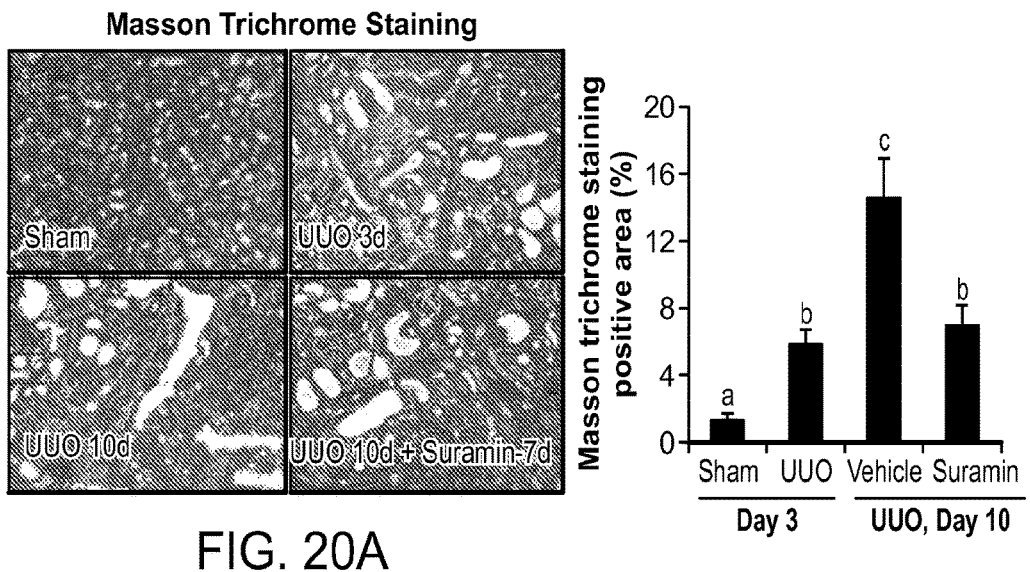
FIG. 20A
FIG. 20B
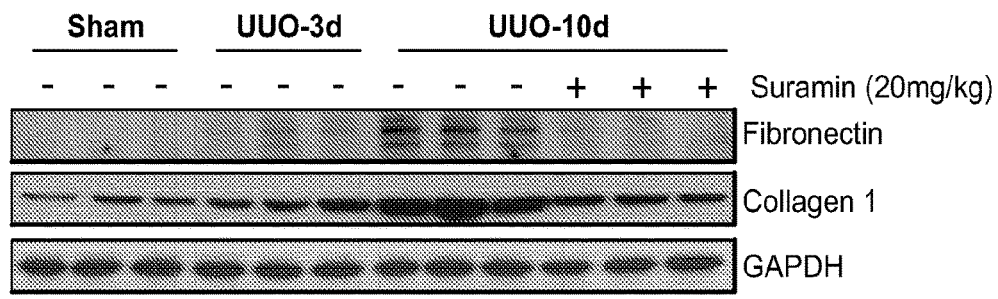
FIG. 20C
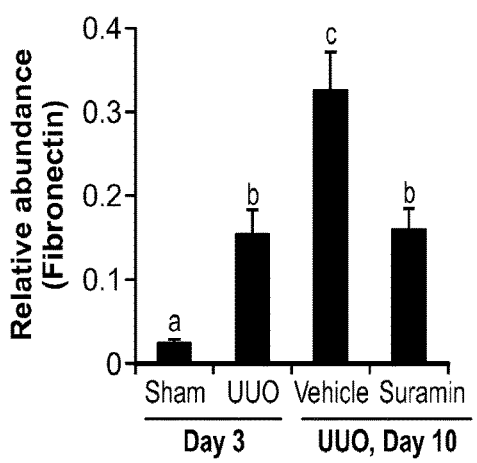
FIG. 20D
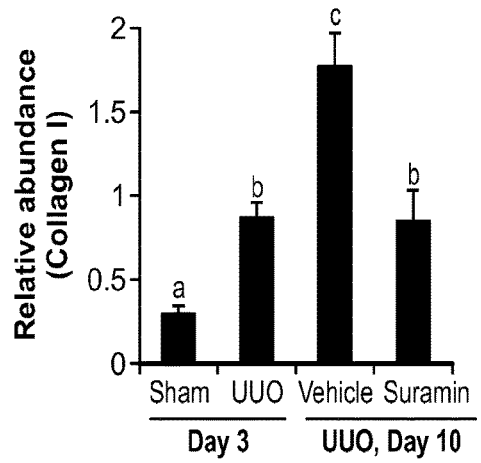
FIG. 20E FIG. 31A  FIG. 31B
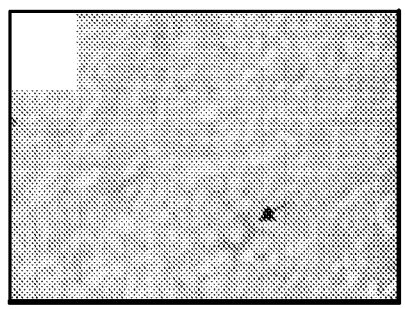 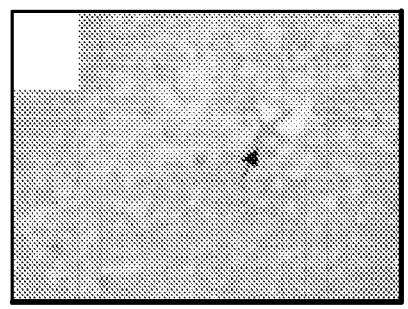
FIG. 31C  FIG. 31D
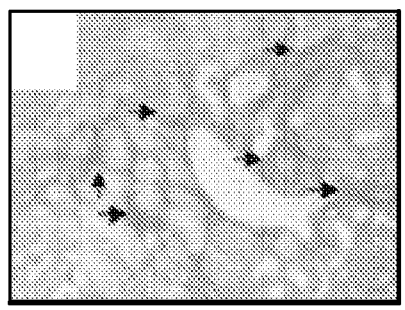 
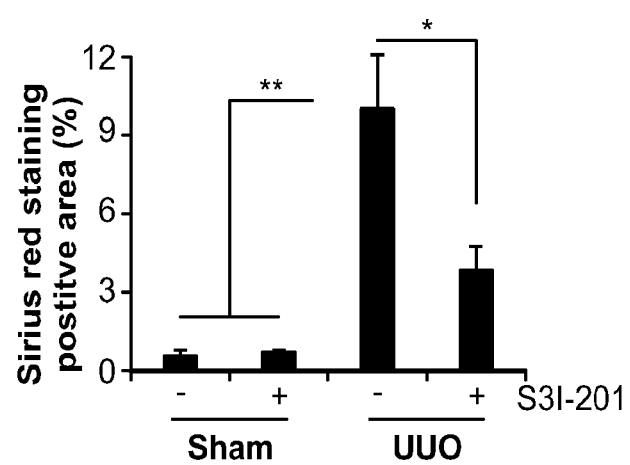
FIG. 31E FIG. 33A
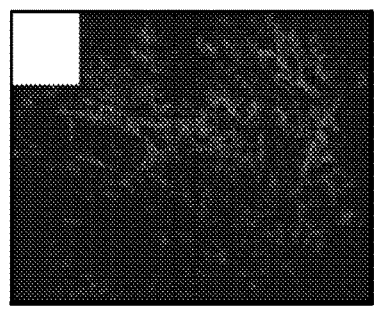
FIG. 33B
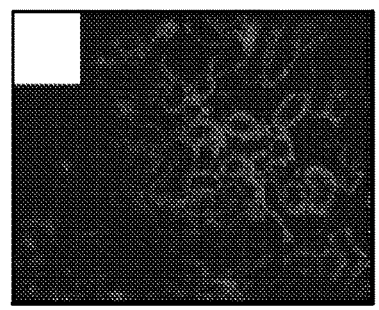
FIG. 33C
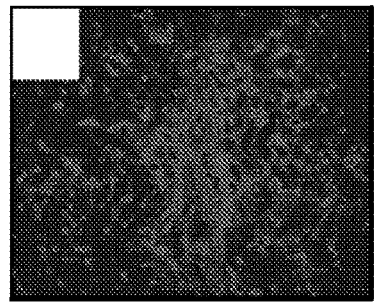
FIG. 33D
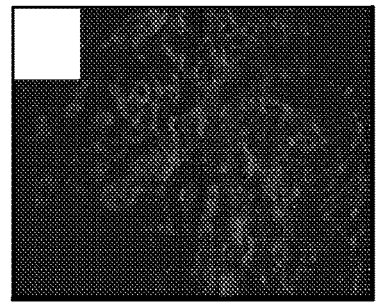
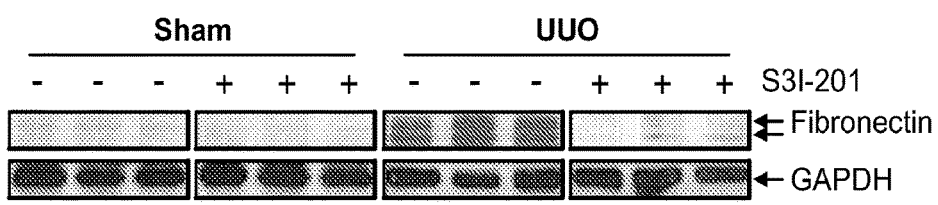
FIG. 33E
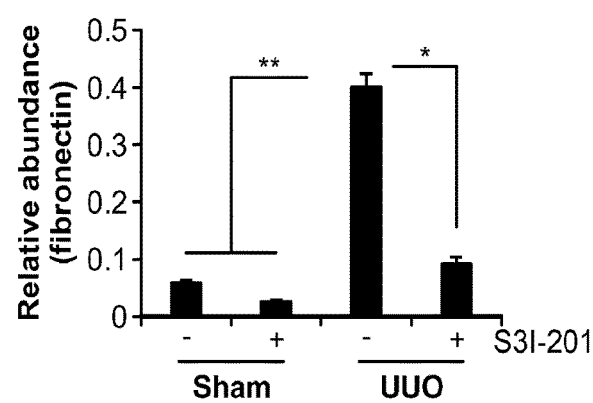
FIG. 33F

*p<0.05

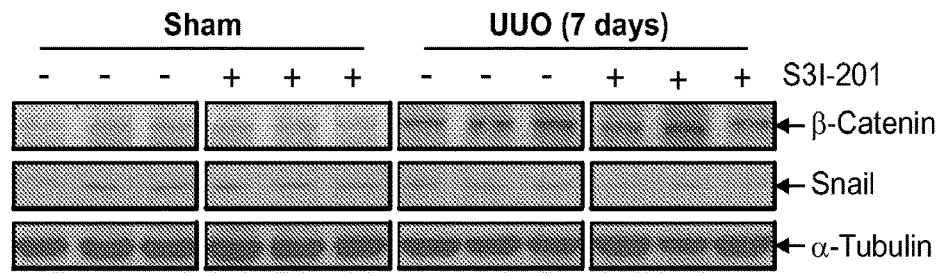
FIG. 40A
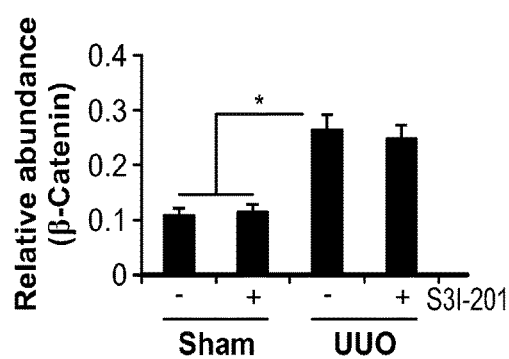 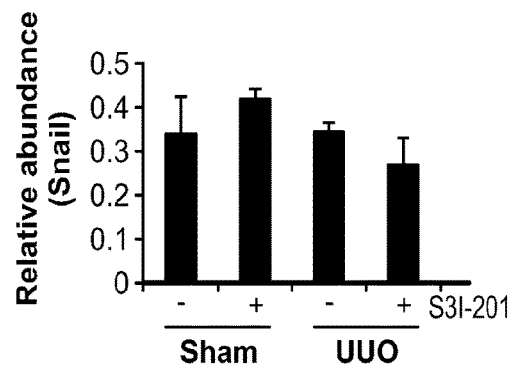
FIG. 40B  FIG. 40C

Tunel Staining
FIG. 41A
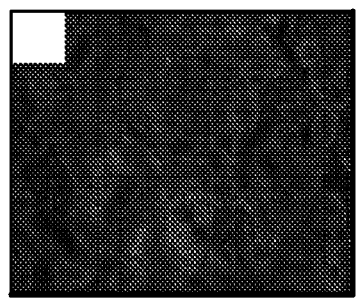
FIG. 41B
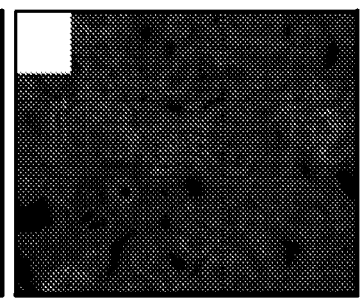
FIG. 41C
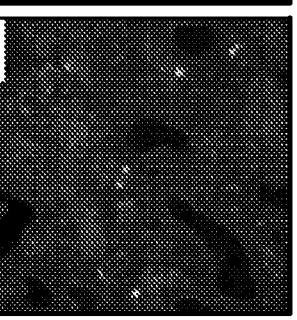
FIG. 41D
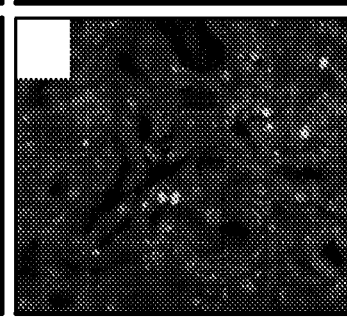
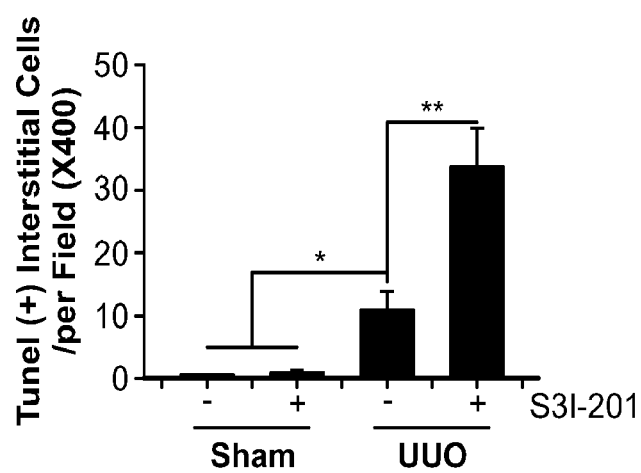
FIG. 41E Histone (Ser-10) Staining
FIG. 42A
FIG. 42B
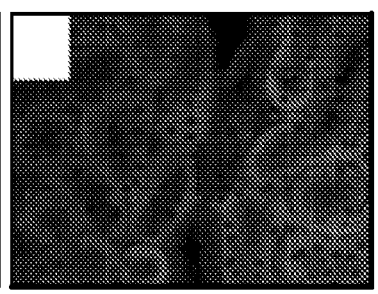
FIG. 42C
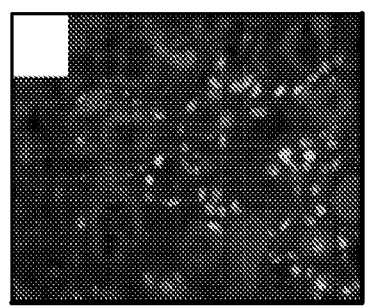
FIG. 42D
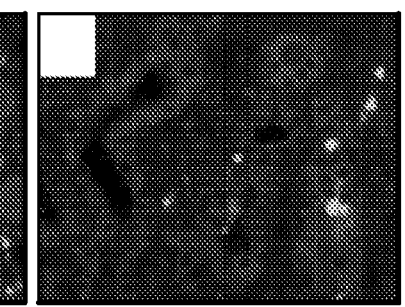
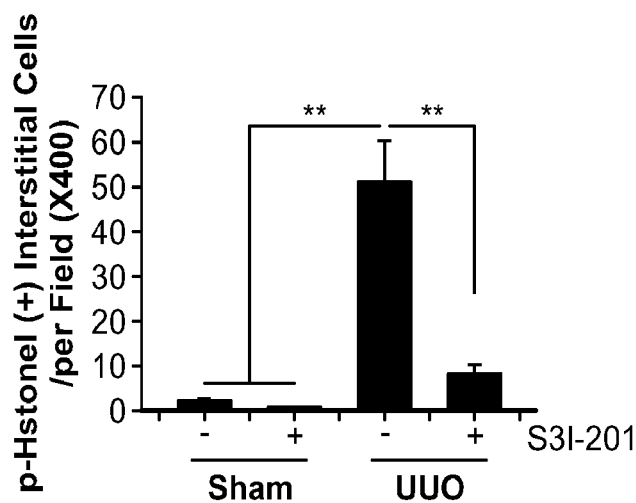
FIG. 42E

INHIBITION OF RENAL FIBROSIS

RELATED APPLICATIONS

This application is a national stage application, filed under 35 U.S.C. §371, of International Application No. PCT/US2012/038799 filed May 21, 2012, which claims priority to the U.S. Provisional Application No. 61/487,871 filed May 19, 2011, the contents of which are hereby incorporated by reference in their entirety.

FIELD OF THE INVENTION

The field of the invention pertains to kidney disease.

BACKGROUND OF THE INVENTION

Tubulointerstitial fibrosis is the final common pathway in late-stage renal disease. The pathogenesis of kidney fibrosis is characterized by overproduction and deposition of extracellular matrix (ECM), which ultimately leads to fibrotic lesions and tissue scarring. Renal interstitial fibroblasts are the principal effector cells that are responsible for ECM overproduction in the fibrotic kidney, and their activation is regarded as a key event in the pathogenesis of chronic renal fibrosis. Although the mechanism of myofibroblast activation and the fibrogenesis under various pathological conditions have not been completely understood, activation of multiple cytokines/growth factor receptors is involved in these processes.

SUMMARY OF THE INVENTION

The present invention is based part upon the surprising discovery that a suramin compound or a STAT3 selective inhibitor can prevent, inhibit, or treat chronic kidney disease. Provided herein are methods of treating, preventing, or alleviating a symptom of chronic kidney disease in a subject by administering to the subject a suramin compound or a selective inhibitor of signal transducer and activator of transcription 3 (STAT3). Preferably, the subject has been diagnosed a suffering from tubulointerstitial fibrosis and/or an obstructive nephropathy.

The invention also provides compositions and methods for treating, preventing or inhibiting renal fibrosis. The method includes the steps of identifying a subject with renal fibrosis or an obstructive nephropathy and administering to the subject a suramin compound and/or a composition that selectively inhibits signal transducer and activator of transcription 3 (STAT3). As used herein, the term "selective STAT3 inhibitor" or "a composition that selectively inhibits STAT3" denotes a natural or synthetic compound which is characterized by inhibitory activity of STAT3 that is considerably greater than the activity for other members of the STAT family of transcription factors. Other members of the family include STAT 1, 2, 4, 5a, 5b, and 6. For example, a selective STAT3 inhibitor, e.g., an antagonist, inhibits the expression, phosphorylation, or other activity of STAT3 at least 20%, 50%, 2-fold, 10-fold, 25-fold, or more compared to the level of inhibition of other family members.

Preferably, the selective STAT3 inhibitory compound comprises S3I-201. Also within the invention are pharmaceutical compositions containing suramin or a STAT3 inhibitory compound formulated for treatment of renal fibrosis or chronic kidney disease (CKD).

Suramin has a chemical formula of $C_{51}H_{34}N_6O_{23}S_6$ and a molecular weight of 1297.29. The structure of suramin is as follows:

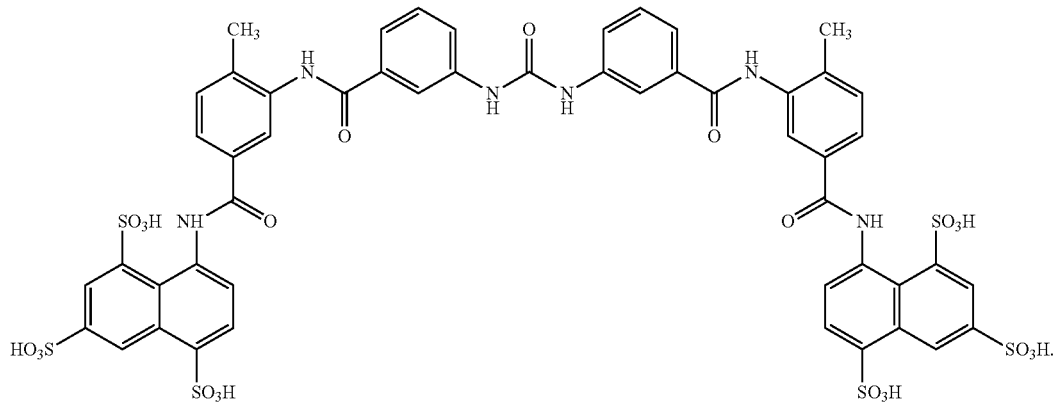 [SMILES: Cc1ccc(C(=O)Nc2ccc(S(=O)(=O)O)c3cc(S(=O)(=O)O)cc(S(=O)(=O)O)c23)cc1NC(=O)c1cccc(NC(=O)Nc2cccc(C(=O)Nc3cc(C(=O)Nc4ccc(S(=O)(=O)O)c5cc(S(=O)(=O)O)cc(S(=O)(=O)O)c45)ccc3C)c2)c1]

S3I-201 has a chemical formula of $C_{16}H_{15}NO_7S$ and a molecular weight of 365.36. The structure of S3I-201 is as follows:

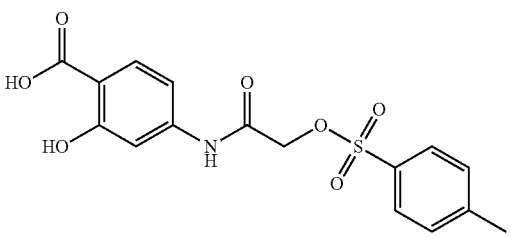 [SMILES: Cc1ccc(S(=O)(=O)OCC(=O)Nc2ccc(C(=O)O)c(O)c2)cc1]

The compound of the present invention can be administered prior to, at the time of, or after the onset of the chronic kidney disease or renal tissue injury. In one example, the compound is administered after establishment of tubulointerstitial fibrosis. For example, the compound is administered weekly or biweekly. One advantage of the invention is that the compound need not be administered daily. Preferably, the subject (to which a suramin compound is administered) has not been diagnosed with cancer or trypanosomiasis.

These compound offer advantages over other therapies, because they not only block development of renal fibrosis when given at an early time relative to an injury or insult but also inhibit progression of renal fibrosis after a significant degree of tubulointerstitial fibrosis has already occurred. Thus, although the methods and compositions are useful for acute injuries, they are particularly advantageous and suitable for treatment of chronic kidney disease.

All compounds of the invention are purified and/or isolated. Specifically, as used herein, an "isolated" or "purified" organic compound is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. Purified also defines a degree of sterility that is safe for administration to a human subject, e.g., lacking infectious or toxic agents.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible or predisposed to a particular adverse condition, disorder, or disease, and thus relates to the prevention of the occurrence of symptoms and/or their underlying cause.

The subject is preferably a mammal in need of such treatment, e.g., a subject that has been diagnosed with an obstructive nephropathy or a predisposition thereto. The mammal can be, e.g., any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

By the terms "effective amount" and "therapeutically effective amount" of a formulation or formulation component is meant a sufficient amount of the formulation or component to provide the desired effect. For example, by "an effective amount" is meant an amount of a compound, alone or in a combination, required to reduce or prevent renal fibrosis in a mammal. Ultimately, the attending physician or veterinarian decides the appropriate amount and dosage regimen.

Also included are derivatives of suramin and S3I-201, which have at least 50%-100% or more of the anti-fibrotic activity of suramin and S3I-201.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

Figure 1A:
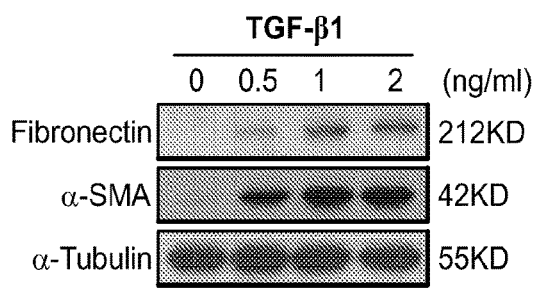
FIGS. 1A, C, and E are photographs and FIGS. 1B, D, and F are bar graphs showing the effect of suramin on TGF-$\beta$1-induced expression of $\alpha$-SMA and fibronectin. Serum-starved NRK-49F cells were incubated with various concentrations of TGF-$\beta$1 for 24 h (A), or 24 h (C, E) with 2 ng/ml TGF-$\beta$1 in the presence of suramin (0-100 µM). Cell lysates were prepared and subject to immunoblot analysis with antibodies to $\alpha$-SMA, fibronectin, p-Smad2, Smad2, p-Smad3 or Smad3 or $\alpha$-Tubulin. Representative immunoblots from three or more experiments are shown. Expression levels of the indicated proteins were quantified by densitometry and normalized with $\alpha$-Tubulin (B, D) or with total Smad2 or Smad3, respectively. Data are represented as the mean±S.E.M. Means with different superscript letters are significantly different from one another ($P<0.05$).
Figure 1B:
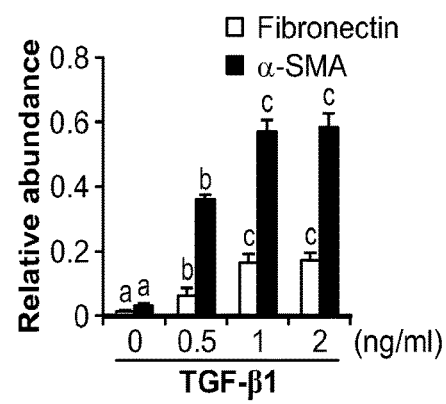
Figure 1C:
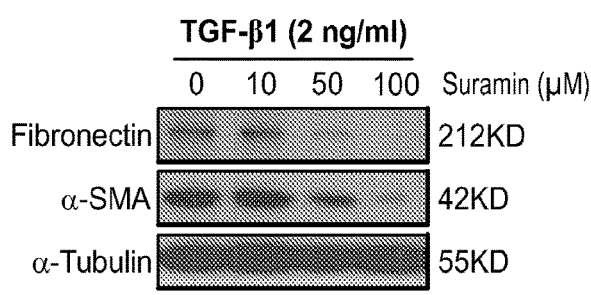
Figure 1D:
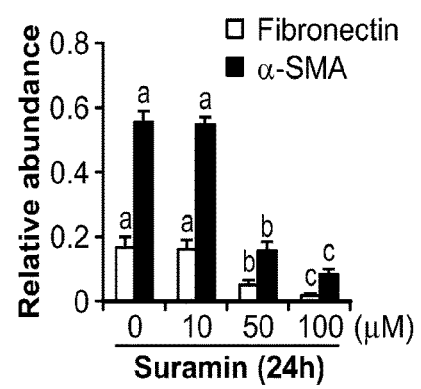

(A) Kidney tissue lysates were subjected to immunoblot analysis with specific antibodies against Smad2 and Smad3. Expression levels of Smad2 (B) and Smad3 (C) were quantified by densitometry and normalized with actin. Data are represented as the mean±S.E.M (n=6). Means with different superscript letters are significantly different from one another (P<0.05). Kidney tissue collected at day 7 was used for costaining with antibodies to p-Smad3 and α-SMA (D).

FIG. 6. Effect of suramin on phosphorylation of EGF receptor. Kidney tissue lysates were subjected to immunoblot analysis with specific antibodies against phospho-EGF receptor (p-EGFR) and EGF receptor (A). Expression levels of p-EGF receptor (B), EGF receptor (C), were quantified by densitometry and normalized with GAPDH. Data are represented as the mean±S.E.M (n=6). Means with different superscript letters are significantly different from one another (P<0.05). Kidney tissue collected at day 7 was used for costaining with antibodies to p-EGFR and α-SMA (D).

FIG. 7. Effect of suramin on phosphorylation of PDGF receptor. (A) Kidney tissue lysates were subjected to immunoblot analysis with specific antibodies against phospho-PDGF receptor-β (p-PDGFRβ), and PDGF receptor (A). Expression levels of p-PDGF receptor-β (B), PDGF receptor-β (C) were quantified by densitometry and normalized with GAPDH. Data are represented as the mean±S.E.M (n=6). Means with different superscript letters are significantly different from one another (P<0.05). Kidney tissue collected at day 7 was used for costaining with antibodies to p-PDGFRβ and α-SMA (D).

FIG. 8. Effect of suramin on phosphorylation of STAT3 and ERK1/2. Kidney tissue lysates were subjected to immunoblot analysis with specific antibodies against phospho-STAT3 (p-STAT3), STAT3, phospho-ERK1/2 (p-ERK1/2), and ERK1/2 (A). Expression levels of p-STAT3, STAT3, p-ERK1/2, and ERK1/2 were quantified by densitometry. Activated STAT3 (B) and ERK1/2 (C) were depicted with p-STAT3/STAT3, p-ERK/ERK ratios, respectively. Protein levels of STAT3 (D) and ERK1/2 (E) were normalized with GADPH. Data are represented as the mean±S.E.M (n=6). Means with different superscript letters are significantly different from one another (P<0.05).

FIG. 9. Effect of suramin on the expression of TNF-α, IL-1β, MCP-1 and ICAM-1. mRNA extracted from kidney tissues were subjected to quantitative real-time RT-PCR as described in "Materials and Methods". mRNA expression levels of TNF-α (A), IL-1β (B), ICAM-1 (C), MCP-1 (D) were indicated as fold induction over control (sham with vehicle). Data are represented as the mean±S.E.M (n=6). Means with different superscript letters are significantly different from one another (P<0.05).

FIG. 10. Effect of suramin on infiltration of leukocytes. Kidney sections were evaluated for infiltration of neutrophils and monocytes with naphthol AS-D chloroacetate esterase staining. Photomicrographs illustrate infiltration of neutrophils and monocytes (red color directed by arrows) in different groups: A, sham with vehicle; B, sham with suramin; C, UUO with vehicle; D, UUO with suramin. E, infiltrated neutrophils and monocytes were counted in three random fields of each sample, and 18 fields (1×200) were analyzed for each condition. Data are represented as the mean±S.E.M (n=6). Means with different superscript letters are significantly different from one another (P<0.05).

FIG. 11. Effect of suramin on renal function and blood pressure in 5/6 nephrectomy in rats. Rats received either vehicle or suramin from day 14 to week 4 after surgery (N=10). A parallel study was conducted in rats after sham operation (N=6). Rats were sacrificed on day 28. A, 24-hour urinary protein excretion; B, serum creatinine; C, mean artery pressure. Data are represented as the mean±S.E.M. Means with different superscript letters are significantly different from one another (P<0.05).

Figure 12A:
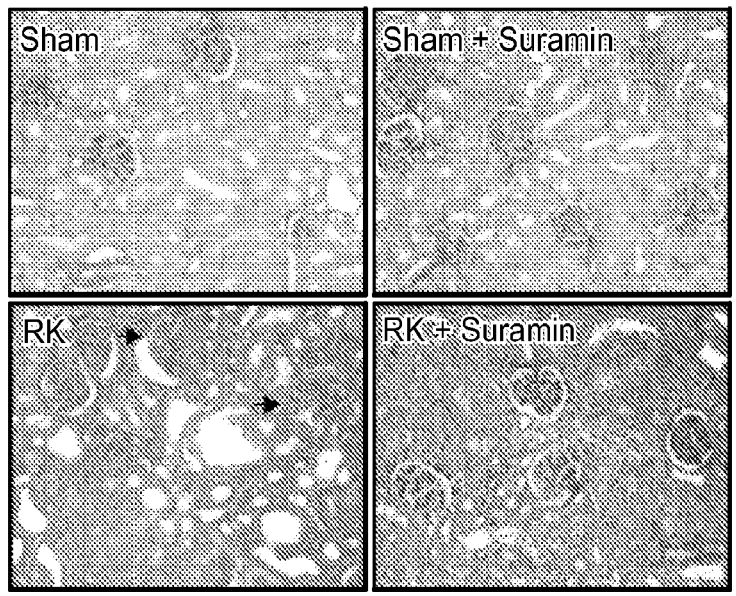
Figure 12B:
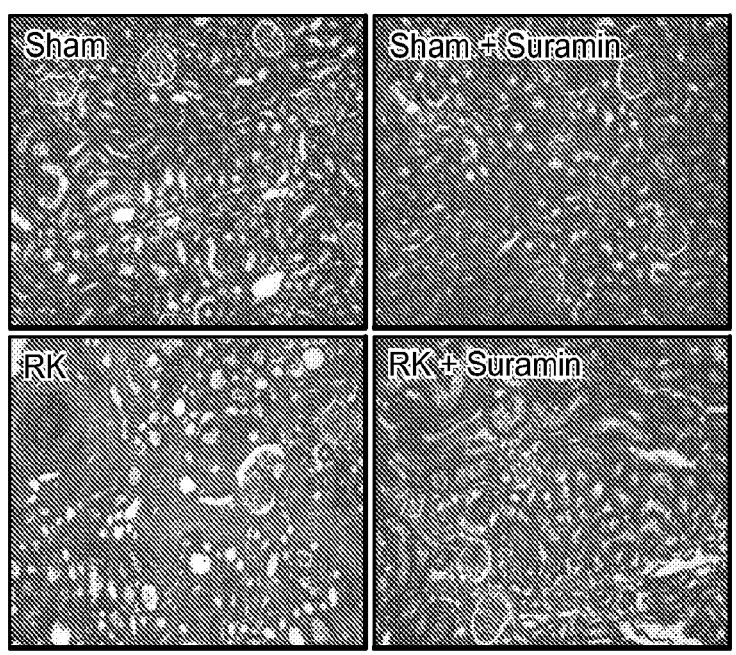

FIG. 12. Effect of suramin on renal histological damage and ECM protein deposition in 5/6 nephrectomy in rats. A, photomicrographs (100×) illustrating periodic acid-Schiff-stained sections of kidney tissue on week 4 after various treatments as indicated. Sclerotic glomerul were indicated with arrows. B, photomicrographs (100×) illustrating trichrome stained kidney tissue on week 4 after various treatments. RK, remnant kidney.

FIG. 13. Suramin inhibits the serum-stimulated activation of renal interstitial fibroblasts, but does not induce cell death. NRK-49F cells were normally cultured with 5% FBS and treated with indicated concentrations of suramin for 36 h (A, B). Cell lysates were subjected to immunoblot analysis using antibodies to α-SMA, Fibronectin, and α-Tubulin. Representative immunoblots from three or more experiments are shown (A). Expression levels of the indicated proteins were quantified by densitometry and normalized with α-tubulin (B). Data are represented as the mean±S.E.M. Means with different superscript letters are significantly different from one another (P<0.05). NRK-49F cells were cultured with 5% FBS in the presence or absence of suramin 100 µM for 36 h or $H_2O_2$ 250 µM for 2 h and cells were harvested for immunoblot analysis of cleaved PARP and cleaved caspase-3 (C).

Figure 14A:
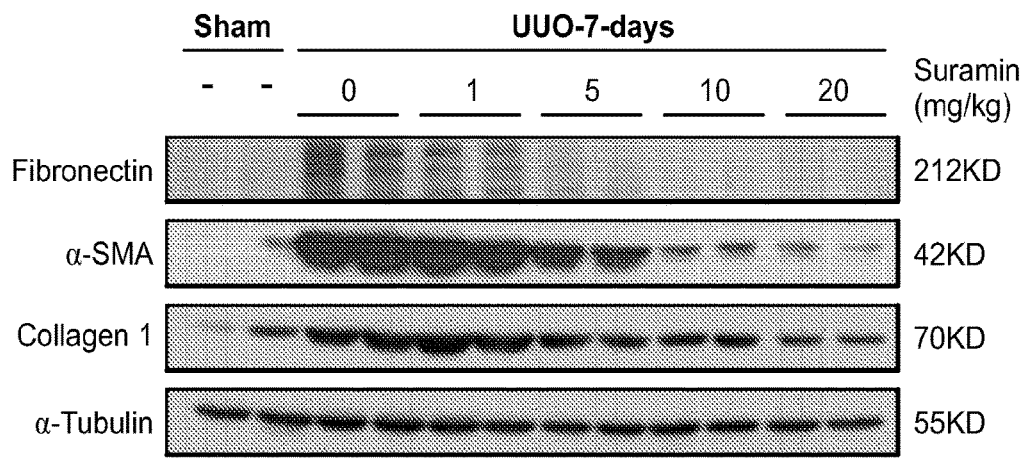
Figure 14B:
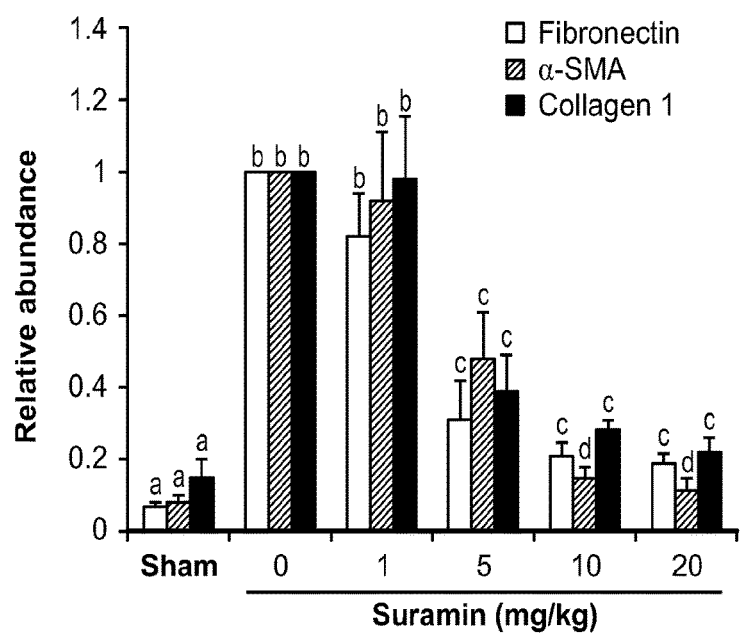
Figure 15A:
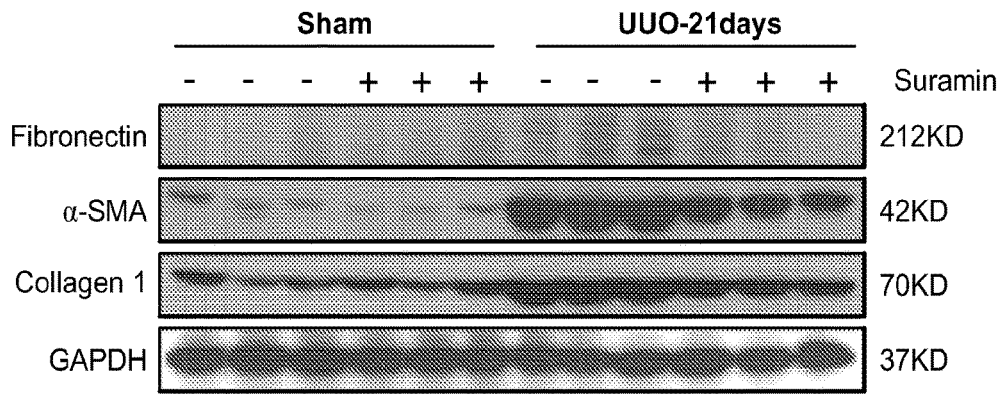
Figure 15B:
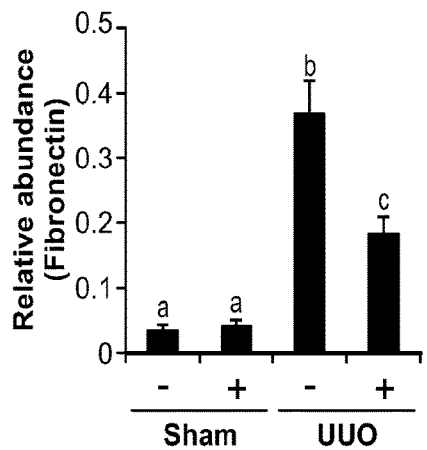
Figure 15C:
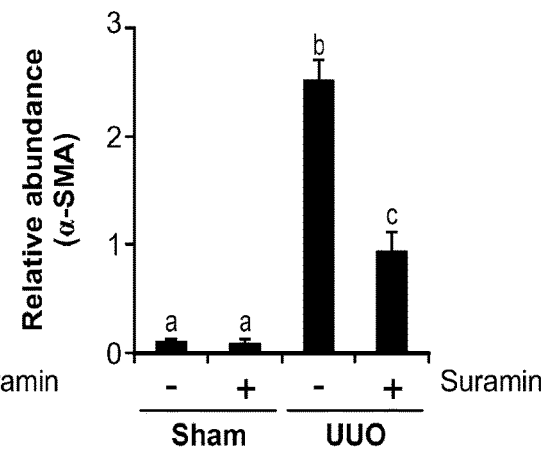
Figure 15D:
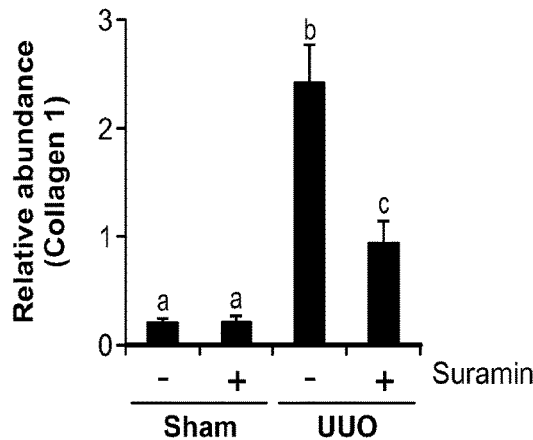
Figure 16A:
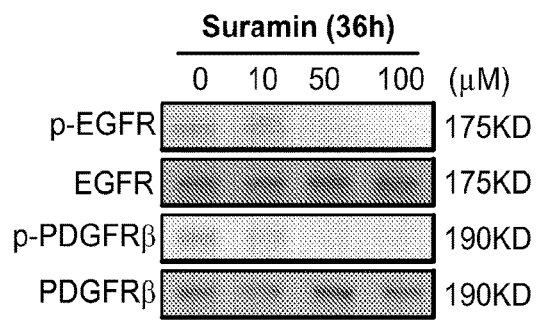
Figure 16B:
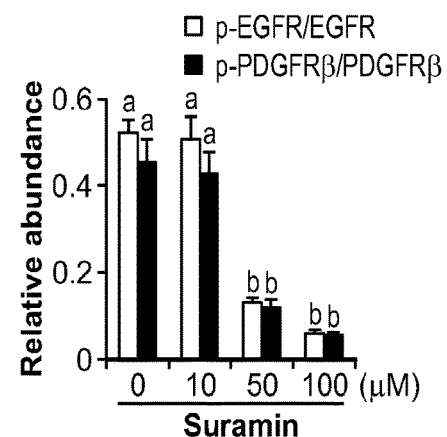
Figure 16C:
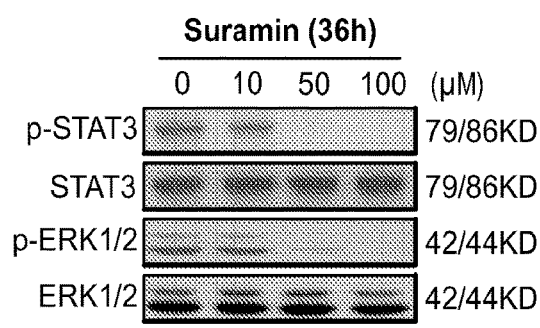
Figure 16D:
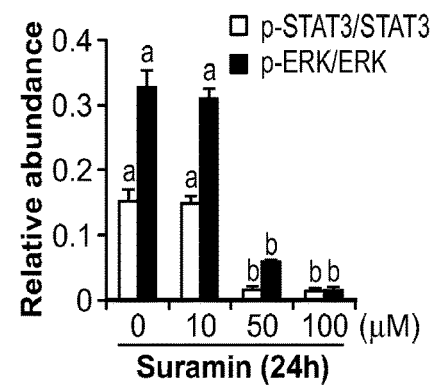

FIG. 14. Dose-dependent suppression of α-SMA, fibronectin and collagen I by suramin. Mice were subject to sham or ureter ligation followed by intraperitoneal injection of suramin at 1, 5, 10, or 20 mg/kg at a single dose. At day 7 after operation, kidneys were collected for protein analysis of α-SMA, fibronectin, collagen I or α-Tubulin (A). Expression levels of α-SMA, fibronectin, collagen type I in the kidney after treatment with those doses of suramin were quantified by densitometry and normalized with α-Tubulin (B). Data are represented as the mean±S.E.M (n=6). Means with different superscript letters are significantly different from one another for a particular protein (P<0.05).

FIG. 15. Long-term effect of suramin on expression of α-SMA, fibronectin and collagen I. Mice were subject to sham or ureter ligation followed by intraperitoneal injection of 20 mg/kg at a single dose. At day 21 after operation, kidneys were collected for protein analysis of α-SMA, fibronectin, collagen type I or GAPDH (A). Expression levels of fibronectin (B), α-SMA (C), collagen type I (D) were quantified by densitometry and normalized with GAPDH. Data are represented as the mean±S.E.M (n=6). Means with different superscript letters are significantly different from one another (P<0.05).

FIG. 16. Suramin inhibits phosphorylation of EGFR, PDGFRβ, STAT3 and ERK1/2 in cultured renal interstitial fibroblasts. NRK-49F cells were cultured with 5% FBS and treated with indicated concentrations of suramin for 36 h. Cell lysates were subjected to immunoblot analysis using antibodies to phospho-EGFR (p-EGFR), EGFR, phospho-PDGFRβ (p-PDGFRβ), and PDGFRβ (A) as well as those to phospho-STAT3 (p-STAT3), STAT3, phospho-ERK1/2 (p-ERK1/2) and ERK1/2 (C). Representative immunoblots from three experiments are shown (A, C). Expression levels of the indicated proteins were quantified by densitometry and normalized with EGFR, PDGFRβ, STAT3, ERK1/2 (B, D). Data are represented as the mean±S.E.M. Means with different superscript letters are significantly different from one another (P<0.05).

FIG. 17. Suramin administration blocks de novo expression of α-SMA and fibronectin and increased expression of type 1 collagen in the remnant kidney. Kidneys were collected for protein analysis of α-SMA, fibronectin, type 1 collagen or GADPH (A). Expression levels of fibronectin (B) and type I collagen (C) in the kidney after various treatments were quantified by densitometry and normalized with GADPH (B). Data are represented as the mean±S.E.M (n=6). Means with different superscript letters are significantly different from one another for a particular protein (P<0.05).

Figure 18:
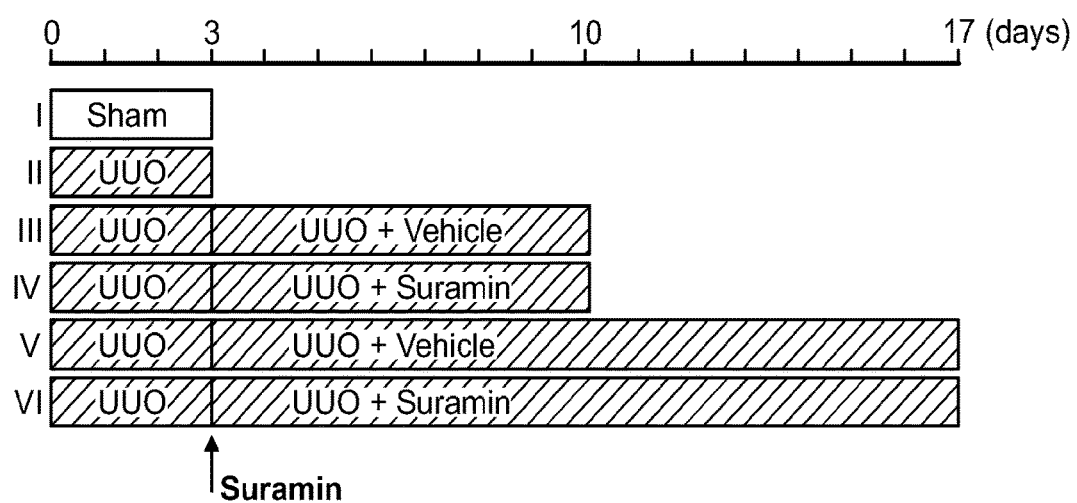

FIG. 18. Experimental design. Experiments were designed to evaluate the effect of suramin given at 3 days of obstruction on the progression of renal fibrosis.

FIG. 19. Time course of UUO-induced expression of type 1 collagen, fibronectin, α-SMA. The left ureter was ligated. At day 1, 3, 7, 14, the kidneys were taken for analyzing the expression of type 1 collagen, fibronectin, α-SMA and GADPH. Representative immunoblots from three or more experiments are shown (A). Expression levels of fibronectin (B), type 1 collagen (C), α-SMA (D) were quantified by densitometry and normalized with GADPH. Data are means±SEM (n=6). Means with different superscript letters are significantly different from one another (P<0.05).

FIG. 20. Effect of delayed suramin administration on UUO-induced deposition of ECM and expression of type 1 collagen and fibronectin. Mice received surgery and suramin treatment as described in protocol 1. (A) Photomicrographs illustrating Masson trichrome staining of kidney tissue after various treatments. (B) The graph shows the percentage of Masson trichrome-positive tubulointerstitial area (blue) relative to the whole area from 10 random cortical fields (200×) (means±SEM). (C) Kidney tissue lysates were subjected to immunoblot analysis with specific antibodies against type 1 collagen, fibronectin, or GADPH. Expression levels of fibronectin (D) and type collagen I (E) were quantified by densitometry and normalized with GADPH. Data are means±SEM (n=6). Means with different superscript letters are significantly different from one another (P<0.05).

Figure 21A:
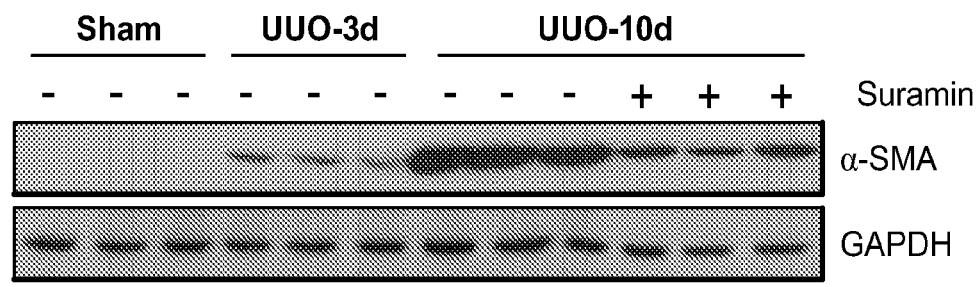
Figure 21B:
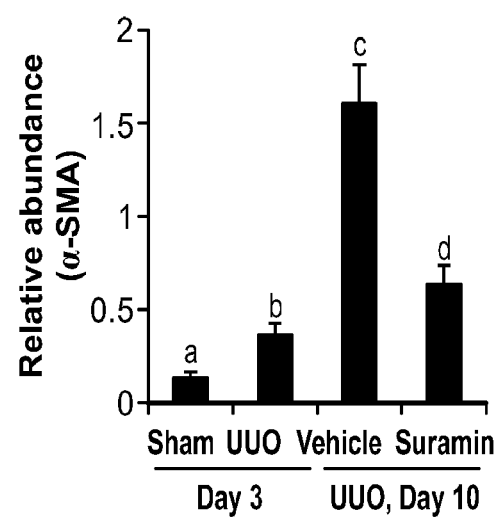
Figure 22A:
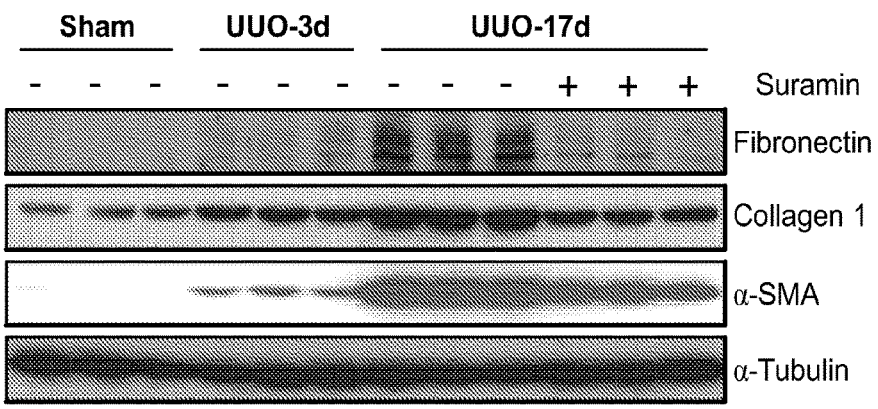
Figure 22B:
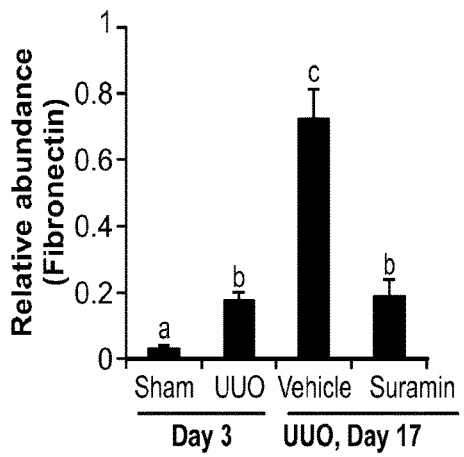
Figure 22C:
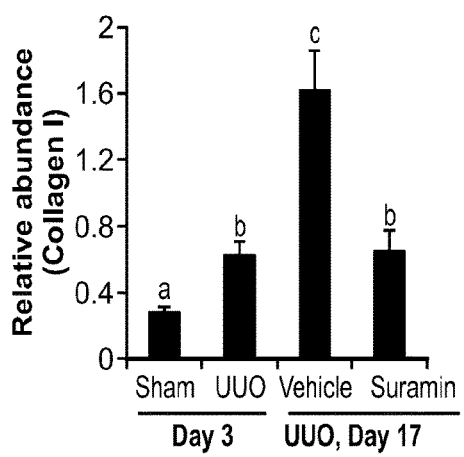
Figure 22D:
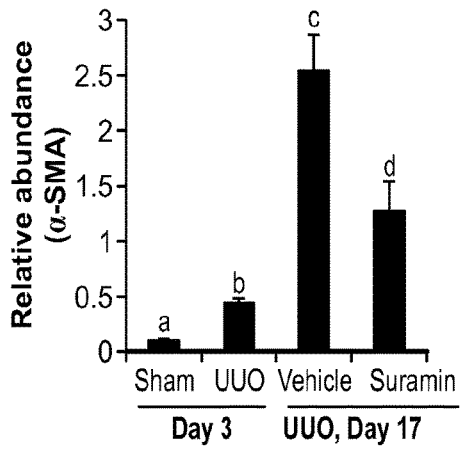

FIG. 21. Effect of delayed suramin administration on UUO-induced expression of α-SMA. Mice received surgery and suramin treatment as described in FIG. 1. (A) Kidney tissue lysates were subjected to immunoblot analysis with specific antibodies against α-SMA or GADPH. (B) Expression levels of α-SMA was quantified by densitometry and normalized with GADPH. Data are means±SEM (n=6). Means with different superscript letters are significantly different from one another (P<0.05).

FIG. 22. The long-term effect of delayed suramin administration on UUO-induced expression of type 1 collagen, fibronectin and α-SMA. Mice received surgery and suramin treatment as described in FIG. 18. Kidney tissue lysates were subjected to immunoblot analysis with specific antibodies against type 1 collagen, fibronectin, α-SMA or GADPH (A). Expression levels of fibronectin (B), type I collagen (C), and α-SMA (D) were quantified by densitometry and normalized with GADPH. Data are means±SEM (n=6). Means with different superscript letters are significantly different from one another (P<0.05).

Figure 23A:
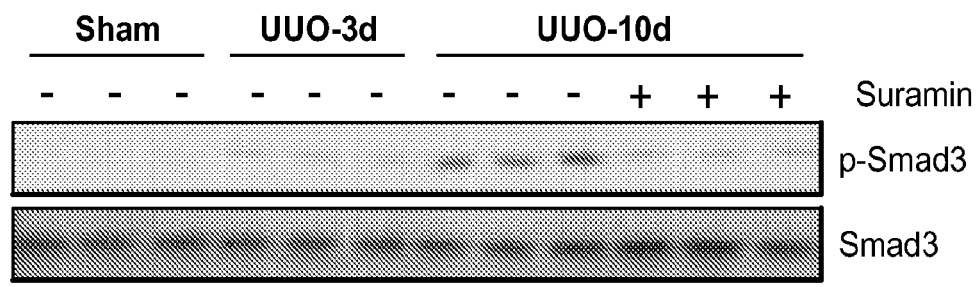
Figure 23B:
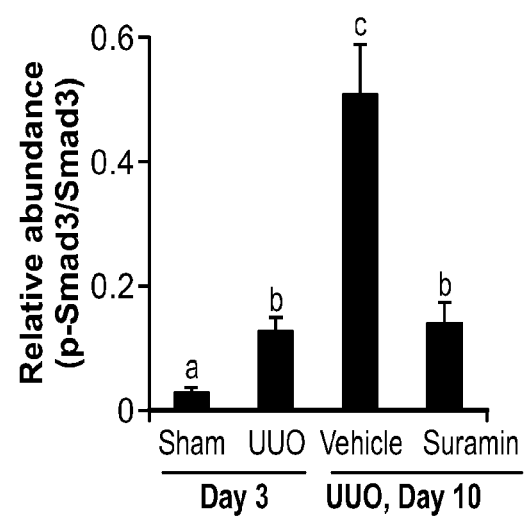

FIG. 23. Effect of delayed suramin administration UUO-induced phosphorylation of Smad3. Mice received surgery and suramin treatment as described in FIG. 1. (A) Kidney tissue lysates were subjected to immunoblot analysis with specific antibodies against phospho-Smad3 or Smad3. (B) Expression levels of p-Smad3 and Smad3 was quantified by densitometry and normalized with GADPH. Data are means±SEM (n=6).

FIG. 24. Effect of delayed suramin administration on UUO-induced phosphorylation of EGFR and PDGFR β. Mice received surgery and suramin treatment as described in FIG. 1. (A) Kidney tissue lysates were subjected to immunoblot analysis with specific antibodies against p-PDGFRβ, PDGFRβ, p-EGFR, EGFR, or GAPDH. Expression levels of p-PDGFRβ (B), p-EGFR (D) were quantified by densitometry and normalized with PDGFRβ or EGFR. Expression levels of PDGFRβ (C), EGFR (E) were quantified by densitometry and normalized with GADPH. Data are means±SEM (n=6). Means with different superscript letters are significantly different from one another (P<0.05).

FIG. 25. Effect of delayed suramin administration on UUO-induced phosphorylation of STAT3 and ERK1/2. Mice received surgery and suramin treatment as described in FIG. 18. (A) Kidney tissue lysates were subjected to immunoblot analysis with specific antibodies against p-STAT3, STAT3, p-ERK1/2, ERK1/2 or GAPDH. Expression levels of p-STAT3 (B), p-ERK1/2 (D) were quantified by densitometry and normalized with STAT3 and ERK1/2. Expression levels of STAT3 (C), ERK1/2 (E) were quantified by densitometry and normalized with GADPH. Data are means±SEM (n=6). Means with different superscript letters are significantly different from one another (P<0.05).

Figure 26A:
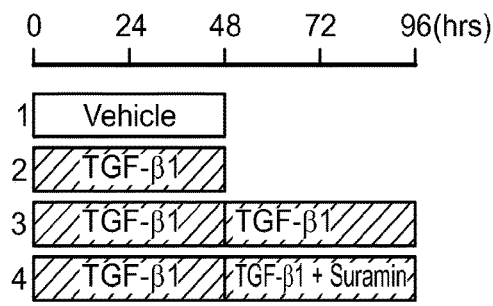
Figure 26B:
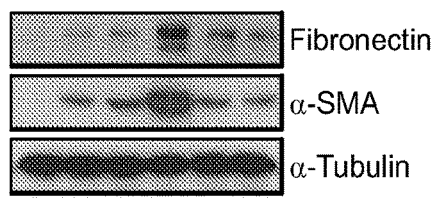
Figures 26C, 26D:
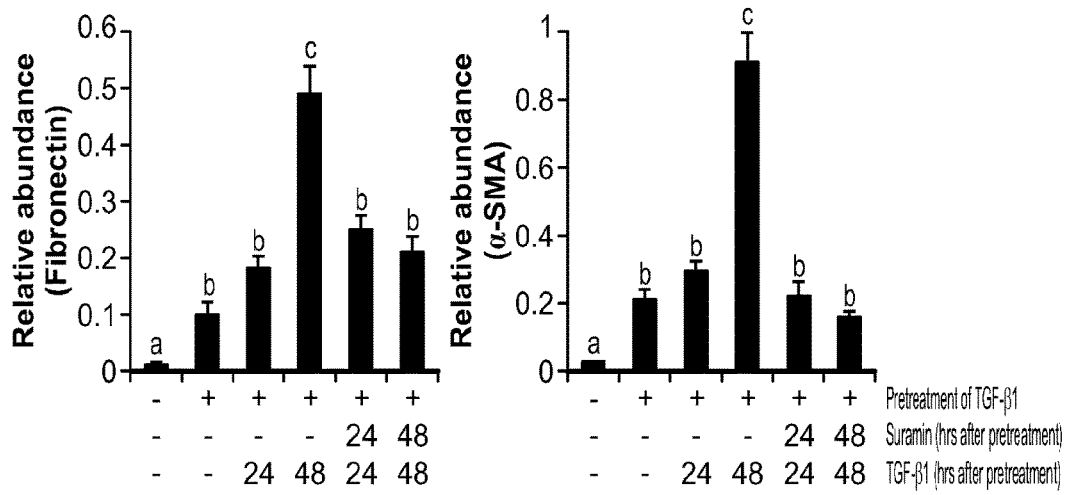

FIG. 26. Delayed administration of suramin inhibits TGF-β1-induced α-SMA and fibronectin expression in renal interstitial fibroblasts. (A) Diagram depicts treatment scheme with suramin, which were designed to mimic suramin treatment scheme illustrated in FIG. 18. (B) Immunoblot analysis shows that the levels of α-SMA and fibronectin protein in NRK-49F after various treatments as indicated. Expression levels of fibronectin (C) and α-SMA (D) were quantified by densitometry and normalized with α-Tubulin. Data are means±SEM (n=6). Means with different superscript letters are significantly different from one another (P<0.05).

FIG. 27. Effect of S3I-201 on the expression of α-SMA and fibronectin. Cultured NRK-49F cells were treated with S3I-201 for the indicated concentrations for 24 h (A) or 3 h (E) or exposed to 50 µM S3I-201 for the indicated time (C). Cell lysates were subjected to immunoblot analysis using antibodies to α-SMA, Fibronectin, and GAPDH. Representative immunoblots from three or more experiments are shown. Expression levels of the indicated proteins were quantified by densitometry and normalized with GADPH (B, D). Activated STAT3 was depicted with p-STAT3/STAT3 ratio (F). Data are means±SEM. Significant p-values reflecting differences are indicated over the bars (*P<0.05; **P<0.01).

Figure 28A:
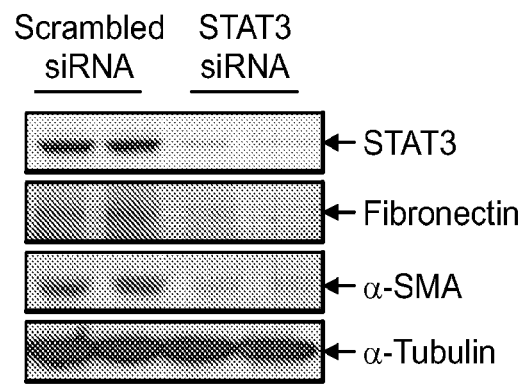
Figure 28B:
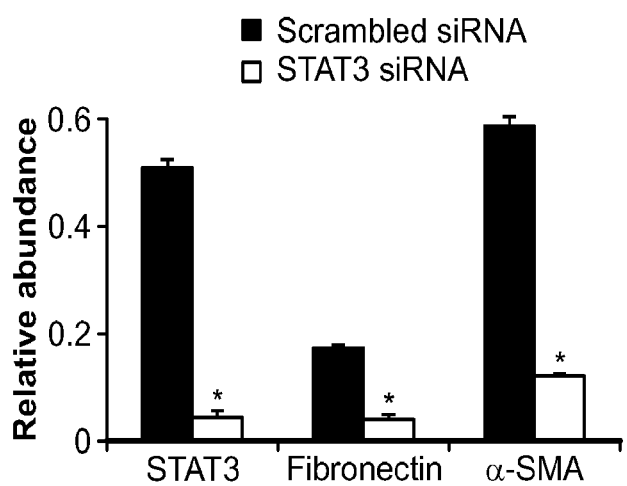

FIG. 28. Effect of STAT3 siRNA on the expression of α-SMA and fibronectin. Cultured NRK-49F cells were transfected with siRNA targeting STAT3 or scrambled siRNA. At 48 h after transfection, cell lysates were subjected to immunoblot analysis using antibodies to STAT3, α-SMA, Fibronectin, and α-Tubulin. Representative immunoblots from three or more experiments are shown (A). Expression levels of the indicated proteins were quantified by densitometry and normalized with α-Tubulin (B). Data are means±SEM. Significant p-values reflecting differences in the expression of individual proteins as indicated between cells treated with STAT3 siRNA and those treated with Scrambled siRNA (*P<0.05).

FIG. 29. Expression of p-STAT3 and STAT3 following UUO injury. The left ureter was ligated. (A, B, C). At day 1, 3, 7, 14, the kidneys were taken for analysis of expression of p-STAT3 and STAT3 and tubulin. Representative immunoblots from three or more experiments are shown. After urethra ligation, kidneys were taken at 1, 3, 7, and 14 days. Expression levels of p-STAT3 and STAT3, were quantified by densitometry and normalized with tubulin (B, C). Kidney tissue collected at day 7 was used for co-staining with antibodies to α-SMA and p-STAT3. Interstitial cells with positive staining for both α-SMA and p-STAT3, α-SMA or p-STAT3 alone were counted in 25 high power fields (HPF) and expressed as means±SE (D).

Figure 30A:
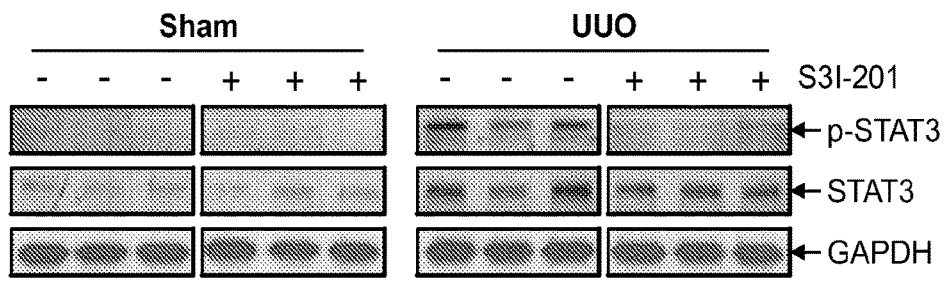
Figure 30B:
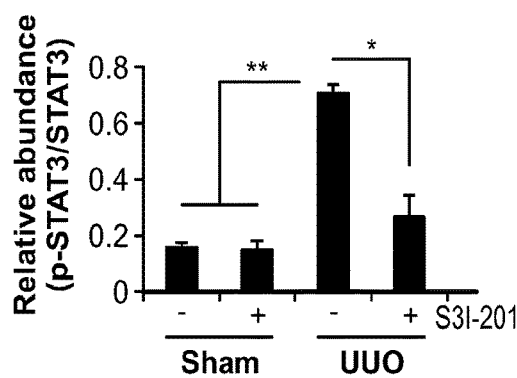
Figure 30C:
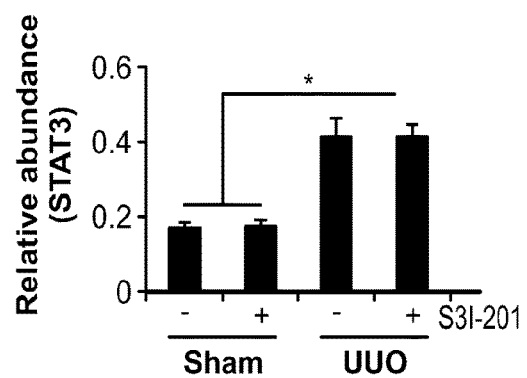

FIG. 30. Effect of S3I-201 on UUO-induced STAT3 activation. Kidney tissue lysates were subjected to immunoblot analysis with specific antibodies against p-STAT3 (Tyr705), STAT3 or GAPDH (A). Activated STAT3 was depicted with p-STAT3/STAT3 ratio (B). Protein expression levels of STAT3 were quantified by densitometry and normalized with GADPH (C). Data are means±SEM (n=6). Significant p-values reflecting differences are indicated over the bars (*P<0.05; **P<0.01).

FIG. 31. Effect of S3I-201 on the deposition of ECM in obstructive kidneys. Photomicrographs illustrating Sirius red staining of kidney tissue after various treatments: A, sham with vehicle; B, sham with S3I-201; C, UUO with vehicle; D, UUO with S3I-201. The graph shows the percentage of Sirius red-positive tubulointerstitial area (red) relative to the whole area from 10 random cortical fields (200×) (means±SEM) (E). Significant p-values reflecting differences are indicated over the bars (*P<0.05; **P<0.01).

FIG. 32. Effect of S3I-201 on UUO-induced α-SMA and collagen I expression. (A), kidney tissue lysates were subjected to immunoblot analysis with specific antibodies against α-SMA, collagen I or α-Tubulin. Expression levels of α-SMA (B) and collagen I (C) were quantified by densitometry and normalized with α-Tubulin. Data are means±SEM (n=6). (D) mRNA was extracted from kidney tissues of sham-operated or obstructed kidneys with/without S3I-201 administration and subjected to quantitative real-time RT-PCR. mRNA expression levels of collagen I were indicated as fold induction over control (sham-operated mice treated with vehicle). Significant p-values reflecting differences are indicated over the bars (*P<0.05; **P<0.01).

FIG. 33. Effect of S3I-201 on UUO-induced fibronectin expression. Photomicrographs illustrate fibronectin (green color) with immunofluorescent staining after various treatments: A, sham with vehicle; B, sham with S3I-201; C, UUO with vehicle; D, UUO with S3I-201. Kidney tissue lysates were subjected to immunoblot analysis with specific antibodies against fibronectin (E). Expression levels of fibronectin in different groups were quantified by densitometry and normalized with GAPDH (F). Data are means±SEM (n=6). Significant p-values reflecting differences are indicated over the bars (*P<0.05; **P<0.01).

FIG. 34. Effect of S3I-201 on mRNA and protein expression of TGF-β1 and mRNA expression of TGF-β receptors. mRNA was extracted from kidney tissues of sham-operated or obstructed kidneys with/without S3I-201 administration and subjected to quantitative real-time RT-PCR as described in "Materials and Methods". mRNA expression levels of TGF-β1 (A), TGF-β receptor type I (B), type II (C) and type III (D) were indicated as fold induction over control (sham-operated mice treated with vehicle). Protein expression levels of TGF-β1 in each group were measured by the ELISA (E). Data are mean±SEM (n=6). Significant p-values reflecting differences are indicated over the bars (*P<0.05; **P<0.01).

FIG. 35. Effect of S3I-201 on infiltration of leukocytes. Kidney sections were evaluated for infiltration of neutrophils and monocytes with naphthol AS-D chloroacetate esterase staining. Photomicrographs illustrate infiltration of neutrophiles and monocytes (red color directed by arrows) in different groups: A, sham with vehicle; B, sham with S3I-201; C, UUO with vehicle; D, UUO with S3I-201. E, infiltrated neutrophils and monocytes were counted in three random fields of each sample, and 18 fields (1×200) were analyzed for each condition. Data are mean±SEM (n=6). Significant p-values reflecting differences are indicated over the bars (*P<0.05).

FIG. 36. Effect of S3I-201 on the expression of TNF-α, MCP-1 and ICAM-1. mRNA extracted from kidney tissues were subjected to quantitative real-time RT-PCR as described in "Materials and Methods". mRNA expression levels of TNF-α (A), IL-1β (B), MCP-1 (C) and ICAM-1 (D) were indicated as fold induction over control (sham with vehicle). Protein expression levels of TNF-α (E) and IL-1β (F) in each group were measured by the ELISA. Data are means±SEM (n=6). Significant p-values reflecting differences are indicated over the bars (*P<0.05; **P<0.01).

Figure 37A:
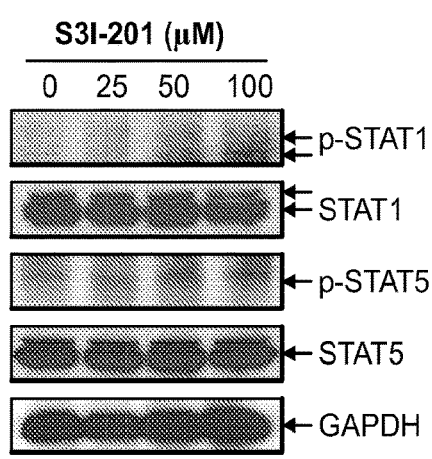
Figure 37B:
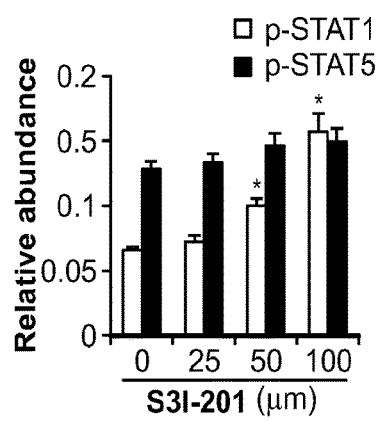
Figure 38A:
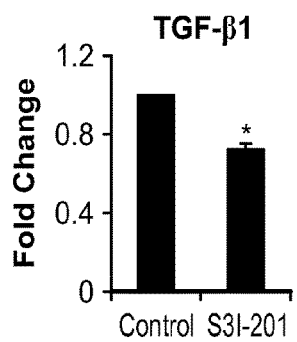
Figure 38B:
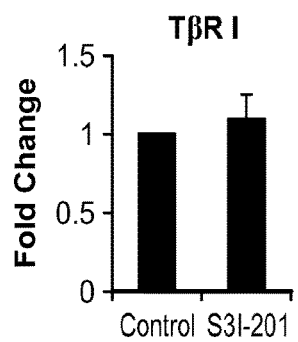
Figure 38C:
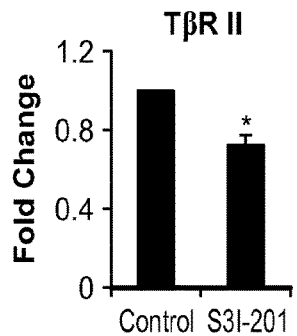
Figure 38D:
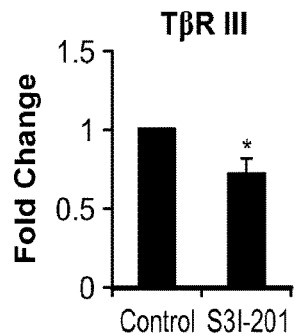
Figure 39A:
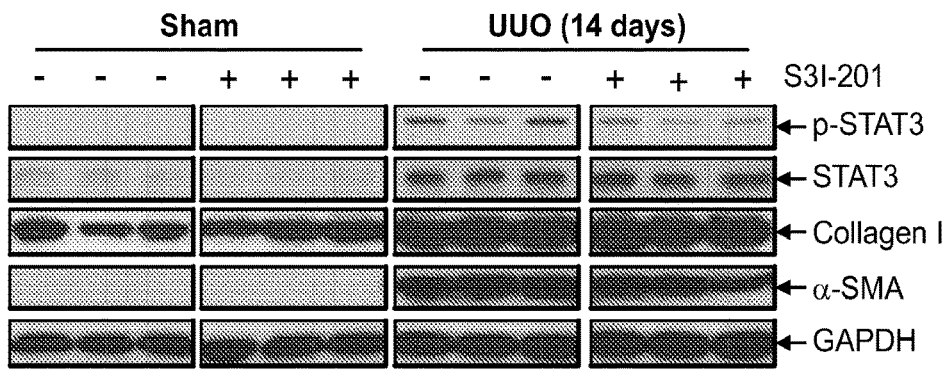
Figure 39B:
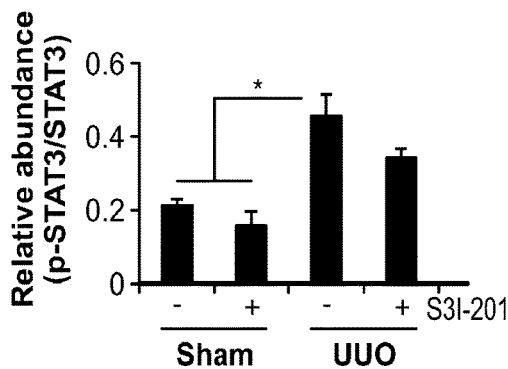
Figure 39C:
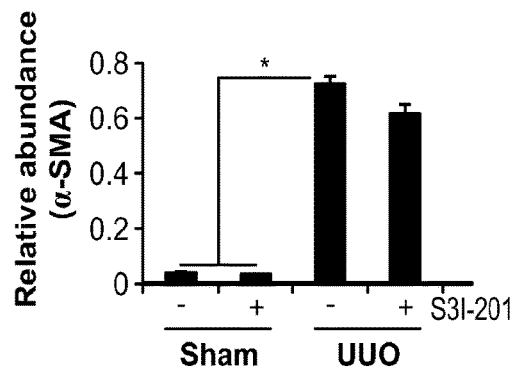
Figure 39D:
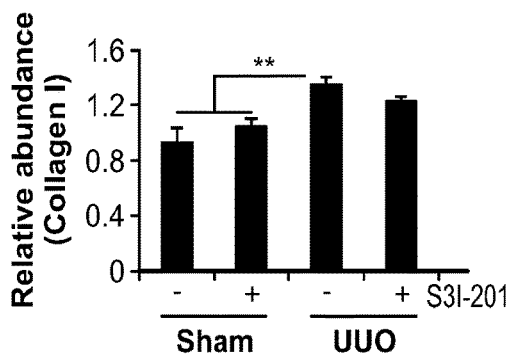

FIG. 37. Effect of STAT3 inhibition on the expression and phosphorylation of STAT1 and STAT5. Cultured NRK-49F cells were treated with S3I-201 for the indicated concentrations for 3 h (A). Cell lysates were subjected to immunoblot analysis using antibodies to p-STAT1, STAT1, p-STAT5 and STAT5. Representative immunoblots from three or more experiments are shown. Activated STAT was depicted with p-STAT/STAT ratio (B). Data are means±SEM. Significant p-values reflecting differences are indicated over the bars (*P<0.05).

FIG. 38. Effect of S3I-201 on the mRNA expression of TGF-β1, TβR1, TβR II and TβR III in cultured renal interstitial fibroblasts. NRK-49F cells were starved for 24 h and then incubated with 5% FBS in the absence or presence of 50 μM S3I-201 for 6 h. Cell were harvested and cell lysates were then analyzed by quantitative real-time RT-PCR as described in "Materials and Methods". mRNA expression levels of TGF-β1 (A), TGF-β receptor type I (B), type II (C) and type III (D) were indicated as fold induction over control (sham-operated mice treated with vehicle). Data are means±SEM (n=6). Significant p-values reflecting differences are indicated over the bars (*P<0.05; *P<0.01).

FIG. 39. Effect of S3I-201 on the phosphorylation of STAT3 and expression of collagen type I and α-SMA on day 14 after UUO injury. Tissues lysates from sham-operated or obstructed kidneys with/without S3I-201 administration for 14 days were subject to immunoblot with specific antibodies against p-STAT3, STAT3, α-SMA, collagen type I, or GADPH (A). Expression levels of the indicated proteins were quantified by densitometry and normalized with GADPH (B-D). Data are means±SEM (n=6). Significant p-values reflecting differences are indicated over the bars (*P<0.05; **P<0.01).

FIG. 40. Effect of S3I-201 on the expression of β-catenin and Snail on day 7 after UUO injury. Tissues lysates from sham-operated or obstructed kidneys with/without S3I-201 administration for 7 days were subject to immunoblot with specific antibodies against β-catenin, snail or α-Tubulin (A). Expression levels of the indicated proteins were quantified by densitometry and normalized with α-Tubulin (B, C). Data are means±SEM (n=6). Significant p-values reflecting differences are indicated over the bars (*P<0.05).

FIG. 41. Effect of S3I-201 on apoptosis after UUO injury. Mice were subjected to UUO injury and daily treated with S3I-201 (10 mg/kg) for 7 days. Representative photographs of the distribution of TUNEL-positive nuclei in the kidney of sham (A), Sham+DMSO (B), UUO+DMSO (C), and UUO+S3I-201 (D). Quantified results are shown in E. Data are shown as means±SEM. Significant p-values reflecting differences are indicated over the bars (*P<0.05; **P<0.01). Magnification=×200.

FIG. 42. Effect of S3I-201 on proliferation of interstitial cells after UUO injury. Mice were subject to UUO injury and daily treated with S3I-201 (10 mg/kg) for 7 days. Kidney sections were stained with an antibody to a proliferating maker, phospho-histone H3 (Ser 10). Representative photographs of the distribution of phospho-histone H3 (Ser 10) in the kidney of sham (A), Sham+DMSO (B), UUO+DMSO (C), and UUO+S3I-201 (D). Phospho-histone H3 (Ser 10) positive interstitial cells were counted and expressed as means±SEM (E). Significant p-values reflecting differences are indicated over the bars (*P<0.05; **P<0.01). Magnification=×200.

DETAILED DESCRIPTION

Chronic kidney disease (CKD) is the result of various insults to the kidney, affecting approximately 10% of the normal population. It is a progressive process marked by interstitial fibrosis. The primary aim of treatment in patients with CKD is to prevent and/or at least to slow progression of CKD. But available therapies are limited. The invention provides a solution to the limitations of earlier approaches to treatment.

The present invention is based part upon the surprising discovery that a suramin compound or a STAT3 selective inhibitor can prevent, inhibit or treat chronic kidney disease.

Compounds

In one aspect, the compound of the invention is a compound of formula (I):

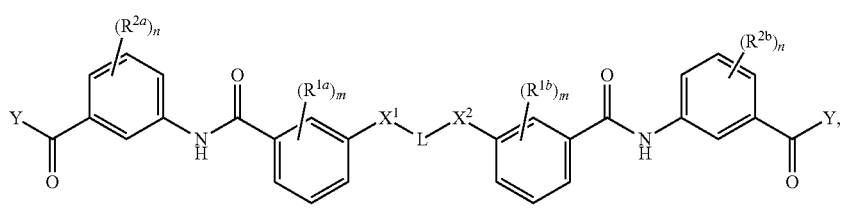

or a pharmaceutically acceptable salt, solvate, or prodrug thereof, wherein $X^1$ and $X^2$ are independently selected from a bond, NH, NH—CO, NH—CS;

L is selected from a bond, CO, CS, piperazinyl, and phenyl; wherein piperazinyl and phenyl are optionally substituted with one or more OH, $C_1$-$C_6$ alkyl, $C_1$-$C_6$ alkoxy, halogen, $NO_2$, $NH_2$, $CH_2F$, $CHF_2$, $CF_3$, $OCH_2F$, $OCHF_2$, and $OCF_3$;

$R^{1a}$, $R^{1b}$, $R^{2a}$, and $R^{2b}$ are independently selected from OH, $C_1$-$C_6$ alkyl, $C_1$-$C_6$ alkoxy, halogen, $NO_2$, $NH_2$, phenyl, $CH_2F$, $CHF_2$, $CF_3$, $OCH_2F$, $OCHF_2$, and $OCF_3$;

Y is selected from:

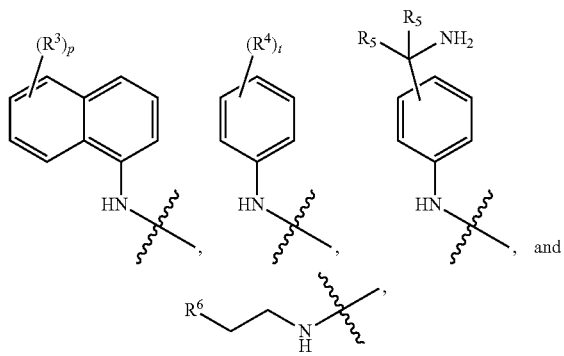

$R^3$, $R^4$, $R^5$, and $R^6$ are independently selected from $SO_3H$, $OPO_3H_2$, OH, $C_1$-$C_6$ alkyl, $C_1$-$C_6$ alkoxy, halogen, $NO_2$, $NH_2$, $CH_2F$, $CHF_2$, $CF_3$, $OCH_2F$, $OCHF_2$, and $OCF_3$;

m is selected 0, 1, 2, 3, and 4;

n is selected 0, 1, 2, 3, and 4;

p is selected from 0, 1, 2, 3, 4, 5, 6 and 7; and t is selected from 0, 1, 2, 3, 4, and 5.

In one aspect, the $X^1$-L-$X^2$ moiety is NH—CO—NH. In one aspect, $R^{2a}$ and $R^{2b}$ are each $C_1$-$C_6$ alkyl (e.g., methyl, ethyl, and propyl). In one aspect, Y is

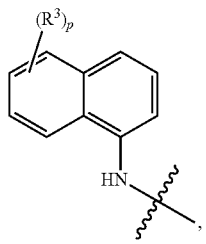

wherein $R^3$ is $SO_3H$ and p is 3. In one aspect, m is 0. In another aspect, n is 1.

In one aspect, the pharmaceutically acceptable salt is an alkali metal salt (e.g., sodium and potassium).

In one aspect, the compound of the invention is a compound of formula (II):

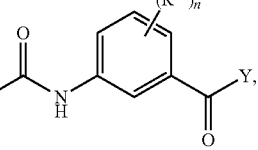

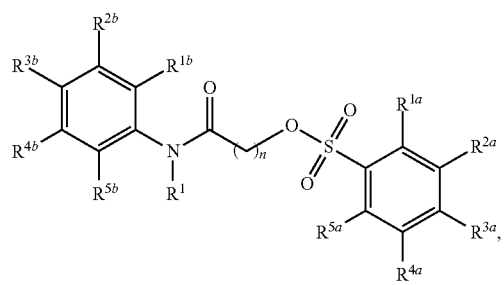

or a pharmaceutically acceptable salt, solvate, or prodrug thereof, wherein $R^1$ is selected from hydrogen and $C_1$-$C_6$ alkyl;

$R^{1a}$, $R^{2a}$, $R^{3a}$, $R^{4a}$, $R^{5a}$, $R^{1b}$, $R^{2b}$, $R^{3b}$, $R^{4b}$, and $R^{5b}$ are independently selected from hydrogen, $C_1$-$C_6$ alkyl, $C_1$-$C_6$ alkoxy, OH, halogen, CN, $NO_2$, $N_3$, $CH_2F$, $CHF_2$, $CF_3$, $OCH_2F$, $OCHF_2$, $OCF_3$, C(O)OH, and C(O)O($C_1$-$C_6$ alkyl); and n is selected from 1, 2, 3, 4, and 5.

In one aspect, the compound of the invention is a compound of formula (IIa):

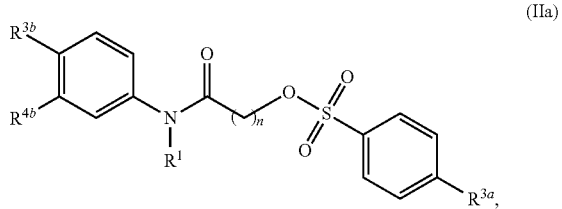

(IIa)

or a pharmaceutically acceptable salt, solvate, or prodrug thereof, wherein $R^1$, $R^{3a}$, $R^{3b}$, $R^{4b}$ and n are as defined in formula (II).

In one aspect, the compound of the invention is a compound of formula (IIb):

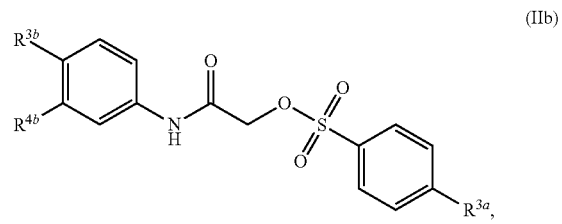

(IIb)

or a pharmaceutically acceptable salt, solvate, or prodrug thereof, wherein $R^{3a}$, $R^{3b}$ and $R^{4b}$ are as defined in formula (II).

In aspect, $R^1$ is hydrogen. In one aspect, $R^{3a}$ is $C_1$-$C_6$ alkyl (e.g., methyl, ethyl, and propyl). In one aspect, $R^{4b}$ is OH. In one aspect, $R^{3b}$ is C(O)OH. In one aspect, n is 1.

DEFINITIONS

"Pharmaceutically acceptable salt" of a compound means a salt that is pharmaceutically acceptable and that possesses the desired pharmacological activity of the parent compound.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.) mifepristone or its derivative can be delivered in prodrug form. Thus, the present invention is intended to cover prodrugs of mifepristone or its derivative, methods of delivering the same and compositions containing the same. "Prodrugs" are intended to include any covalently bonded carriers that release an active parent drug of the present invention in vivo when such prodrug is administered to a subject. Prodrugs the present invention are prepared by modifying functional groups present in the compound in such a way that the modifications are cleaved, either in routine manipulation or in vivo, to the parent compound. Prodrugs include mifepristone or its derivative wherein a hydroxy, amino, sulfhydryl, carboxy, or carbonyl group is bonded to any group that, may be cleaved in vivo to form a free hydroxyl, free amino, free sulfhydryl, free carboxy or free carbonyl group, respectively.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

As used herein, "alkyl" is intended to include both branched and straight-chain saturated aliphatic hydrocarbon groups having the specified number of carbon atoms. For example, $C_{1-6}$ alkyl is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, s-butyl, t-butyl, n-pentyl, s-pentyl, and n-hexyl. "Alkyl" further includes alkyl groups that have oxygen, nitrogen, sulfur or phosphorus atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), and more preferably four or fewer. Likewise, preferred cycloalkyls have from three to eight carbon atoms in their ring structure, and more preferably have five or six carbons in the ring structure.

The term "alkyl" also includes both "unsubstituted alkyls" and "substituted alkyls", the latter of which refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)).

The term "alkoxy" or "alkoxyl" includes substituted and unsubstituted alkyl, alkenyl, and alkynyl groups covalently linked to an oxygen atom. Examples of alkoxy groups (or alkoxyl radicals) include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, and trichloromethoxy.

As used herein, "halo" or "halogen" refers to fluoro, chloro, bromo and iodo.

Pharmaceutical Compositions

The present invention also provides pharmaceutical compositions comprising a compound of the present invention in combination with at least one pharmaceutically acceptable excipient or carrier.

A "pharmaceutical composition" is a formulation containing the compounds of the present invention in a form suitable for administration to a subject. In one embodiment, the pharmaceutical composition is in bulk or in unit dosage form. The unit dosage form is any of a variety of forms, including, for example, a cream, a droplet, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal, topical (e.g., eye drops or ear drops), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the invention can be administered to a subject in many of the well-known methods currently used for treatment of chronic kidney disease. For example, for treatment of retinal degenerative diseases, a compound of the invention may be applied orally. The dose chosen should be sufficient to constitute effective treatment but not so high as to cause unacceptable side effects. The state of the disease condition and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is a chronic kidney disease, including chronic kidney disease in Stage 1, 2, 3, 4, and 5. More preferably, the subject has renal fibrosis.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every day, every 2 days, every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

The pharmaceutical compositions can be administered by systemic, subscleral, transscleral, or intravitreal delivery such that the concentration of a suramin compound or a STAT3 inhibitor is sufficient to promote the survival or function of kidney.

The term systemic as used herein includes subcutaneous injection; intravenous, intramuscular, intraesternal injection; infusion; inhalation, transdermal administration, oral administration; and intra-operative instillation.

A systemic administration of the active compound may involve oral administration, in which pharmaceutical compositions containing active compounds are in the form of tablets, lozenges, aqueous or oily suspensions, viscous gels, chewable gums, dispersible powders or granules, emulsion, hard or soft capsules, or syrups or elixirs. Oral compositions generally include an inert diluent or an edible pharmaceutically acceptable carrier. They can be enclosed in gelatin capsules or compressed into tablets.

For oral use, an aqueous suspension is prepared by addition of water to dispersible powders and granules with a dispersing or wetting agent, suspending agent one or more preservatives, and other excipients. Suspending agents include, for example, sodium carboxymethylcellulose, methylcellulose and sodium alginate. Dispersing or wetting agents include naturally-occurring phosphatides, condensation products of an allylene oxide with fatty acids, condensation products of ethylene oxide with long chain aliphatic alcohols, condensation products of ethylene oxide with partial esters from fatty acids and a hexitol, and condensation products of ethylene oxide with partial esters derived from fatty acids and hexitol anydrides. Preservatives include, for example, ethyl, and n-propyl p-hydroxybenzoate. Other excipients include sweetening agents (e.g., sucrose, saccharin), flavoring agents and coloring agents. Those skilled in the art will recognize the many specific excipients and wetting agents encompassed by the general description above.

For oral application, tablets are prepared by mixing the active compound with nontoxic pharmaceutically acceptable excipients suitable for the manufacture of tablets, troches, or capsules. These excipients may be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil. Formulation for oral use may also be presented as chewable gums by embedding the active ingredient in gums so that the active ingredient is slowly released upon chewing.

Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For systemic administration such as injection and infusion, the pharmaceutical formulation is prepared in a sterile medium. The active ingredient, depending on the vehicle and concentration used, can either be suspended or dissolved in the vehicle. Adjuvants such as local anaesthetics, preservatives and buffering agents can also be dissolved in the vehicle. The sterile injectable preparation may be a sterile injectable solution or suspension in a non-toxic acceptable diluent or solvent. Among the acceptable vehicles and solvents that may be employed are sterile water, saline solution, or Ringer's solution.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.0001 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, improvement in visual function or hearing in a patient may be measured according to methods known to those skilled in the art. For example, improving visual function refers to improving a targeted function of the eye, selected by the artisan, and includes improving any to all of the following capabilities of the eye, retina and visual system: perception of brightness in the presence of light, perception of darkness in the absence of light, perceptions As used herein, the teen "dosage effective manner" refers to amount of an active compound to produce the desired biological effect in a subject or cell.

The pharmaceutical compositions can be included in a container, pack, or dispenser together with instructions for administration.

The compounds of the present invention are capable of further forming salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The compounds of the present invention can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., acetate, propionate or other ester.

The compounds of the present invention can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs in the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the invention, and the like, See Bundegaard, H., *Design of Prodrugs*, p 1-92, Elesevier, New York-Oxford (1985).

The compounds, or pharmaceutically acceptable salts, esters or prodrugs thereof, are administered orally, topically, systemically, subsclerally, transsclerally, or intravitreally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the retinal and/or auditory function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the invention can be found in *Remington: the Science and Practice of Pharmacy*, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

In the synthetic schemes described herein, compounds may be drawn with one particular configuration for simplicity. Such particular configurations are not to be construed as limiting the invention to one or another isomer, tautomer, regioisomer or stereoisomer, nor does it exclude mixtures of isomers, tautomers, regioisomers or stereoisomers.

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) High Throughput Screening, Marcel Dekker; and U.S. Pat. No. 5,763,263. High-throughput assays can use one or more different assay techniques including, but not limited to, those described below.

Mechanisms of Renal Fibrosis

Injury to the kidney is associated with release of cytokines/growth factors such as TGF-β, epidermal growth factor (EGF), and platelet derived growth factor (PDGF) by damaged or infiltrating cells. An increase in production of TGF-β is one of the most important mechanisms in the pathogenesis of renal fibrogenesis. TGF-β1 stimulates fibroblast cell activation and induces matrix expression through its interaction with TGF-β receptors, which are mainly composed of two protein families—type I (TβRI) and type II (TβRII) receptors. TGF-β1 binds to TβRII, which results in TβRI recruitment to form a heteromeric TGF-β receptor complex. The complex phosphorylates and activates Smad2 and Smad3, the two major Smads that mediate the profibrotic events. Other signaling pathways such as extracellular regulated kinase 1/2 (ERK1/2) can also be activated in response to TGF-β receptor activation, Activated ERK1/2 contributes to tubular cell apoptosis in the obstructive kidney. Since activation of TGF-β signaling is considered to be the major mechanism that directly promotes fibroblast activation and fibrosis progression, therapeutic intervention of this pathway could be considered as a strategy to halt or prevent renal fibrosis.

Activation of the EGF receptor and PDGF receptor are also involved in fibroblast activation and fibrogenesis after renal injury. Upon ligand engagement, EGF and PDGF receptors are dimerized and phosphorylated on tyrosine residues. As a result, intracellular signaling pathways including ERK1/2 and signal transducer and activator of transcription 3 are activated. STAT3 sequences are provided in Della Pietra et al., Gene, Volume 213, Issues 1-2, 15 Jun. 1998, Pages 119-124 or UniProtKB/Swiss-Prot P40763 (STAT3_HUMAN; version 136), each of which is hereby incorporated by reference. STAT3 was persistently activated after obstructive injury and involved in activation of renal interstitial fibroblasts, accumulation of inflammatory cells and expression of TGF-β and TβRII, and increase of some proinflammatory mediators such as tumor necrosis factor-α (TNF-α), interleukin-1β (IL-1β) and intercellular adhesion molecule-1 (ICAM-1). Importantly, the EGF receptor not only transduces the fibrotic signal from its ligands, but also has been regarded as a convergent pathway that integrates, directly or indirectly, the effects of many other fibrogenic factors. For example, angiotension II and endothelin induce transactivation of the EGF receptor and inactivation of the EGF receptor attenuates renal fibrosis induced by these substances. Therefore, both the EGF receptor and PDGF receptor are also potential targets for the prevention and treatment of renal fibrosis.

Currently, drug discovery efforts for fighting renal fibrosis are largely focused on compounds that are specific for a particular receptor or protein kinase. Given that renal fibrogenesis is associated with increased production of multiple cytokines/growth factors and subsequent activation of their receptors and signalings pathways, it is expected that inhibitors with broad specificity might offer improved therapeutic benefit in kidney fibrotic diseases.

Method of Treatment

Chronic kidney disease (CKD), also known as chronic renal disease, is a progressive loss in renal function over a period of months or years. Renal fibrosis, characterized by glomerulosclerosis and tubulointerstitial fibrosis, is the common manifestation of a wide variety of chronic kidney diseases (CKD). The pathogenesis of renal fibrosis is, in essence, a monotonous process that is characterized by an excessive accumulation and deposition of extracellular matrix (ECM) components. Renal fibrosis is a progressive process that ultimately leads to end-stage renal failure, a devastating disorder that requires dialysis or kidney transplantation. However, there is no specific treatment unequivocally shown to slow the worsening of chronic kidney disease.

The present invention provides a method for treating, preventing, or alleviating a symptom of CKD by administering to the subject a suramin compound of formula (I) or a selective STAT3 inhibitor of formula (II), or a pharmaceutically acceptable salt, prodrug, metabolite, solvate, and polymorph thereof, optionally in a therapeutically effective amount.

Also provided are methods for treating, preventing, or inhibiting renal fibrosis. The methods comprise identifying a subject with an obstructive nephropathy and administering the subject a suramin compound, e.g., a compound of formula (I), or a selective STAT3 inhibitor, e.g., a compound of formula (II), or a pharmaceutically acceptable salt, prodrug, metabolite, solvate, and polymorph thereof, optionally, in a therapeutically effective amount. As used herein, the term "selective STAT3 inhibitor" or "a composition that selectively inhibits STAT3" denotes a natural or synthetic compound which acts selectively to inhibit the expression, phosphorylation, or activity of STAT3, i.e., a STAT3 antagonist. Other STAT3 inhibitors include antisense molecules (e.g., as described in Wang et al., Nature Medicine 10:1 48-54 (2004), hereby incorporated by reference), anti-Stat3 antibodies, dominant negative mutants of Stat3, e.g., Stat3.beta. (Nakajima K et al. EMBO J. 15, 3651-3658 (1996), incorporated herein by reference), and phosphotyrosyl peptides that complex with Stat3 monomers and prevent the formation of dimers, e.g., PY*LKTK (where Y* represents phosphotyrosine) (SEQ ID NO: 1) (e.g., as described in Turkson et al., J. Biol. Chem. 276, 45443-45455 (2001), incorporated herein by reference in its entirety).

Preferably, the STAT3 inhibitor used in any method of the present invention is S3I-201.

In a preferred embodiment, the subject has not been diagnosed with cancer. More preferably, the subject has renal fibrosis. Alternatively, the subject has renal fibrosis characterized by tubulointerstitial fibrosis.

A subject (patient) may be a human being or a non-human animal, such as dogs, cats, rats, mice, but is preferably a human. Usually the individual has suffered or is in risk of developing CKD that results in some degree of kidney function loss and/or has a condition that will result in CKD. Preferably, the subject has suffered or is in risk of developing a CKD (such as a subject having diseases and conditions that can damage the kidneys). Diseases and conditions that can damage the kidneys and lead to CKD include, but are not limited to, autoimmune disorders (such as systemic lupus erythematosus and scleroderma); birth defects of the kidneys (such as polycystic kidney disease); certain toxic chemicals; glomerulonephritis; injury or trauma; kidney stones and infection; problems with the arteries leading to or inside the kidneys; reflux nephropathy (in which the kidneys are damaged by the backward flow of urine into the kidneys). A healthy subject does not have a condition that will result in CKD and/or has not suffered CKD.

The compound or the pharmaceutical composition of the present invention may be administered prior to, concurrently, or after the onset of physical or histological symptoms of CKD, such as the time of renal tissue injury, or the establishment of tubulointerstitial fibrosis.

The "therapeutic effective amount" used herein refers to that amount of the therapeutic agent sufficient to result in amelioration of one or more symptoms of the disorder, or prevent advancement of the disorder, or cause regression of the disorder without undesirable side effects, such as toxicity, irritation or allergic response. Although individual needs may vary, the determination of optimal ranges for effective amounts of formulations is within the skill of the art. Human doses can readily be extrapolated from animal studies (Katocs et al., Chapter 27 In: Remington's Pharmaceutical Sciences, 18th Ed., Gennaro, ed., Mack Publishing Co., Easton, Pa., 1990). Generally, the dosage required to provide an effective amount of a formulation, which can be adjusted by one skilled in the art, will vary depending on several factors, including the age, health, physical condition, weight, type and extent of the disease or disorder of the recipient, frequency of treatment, the nature of concurrent therapy, if required, and the nature and scope of the desired effect(s) (Nies et al., Chapter 3 In: Goodman & Gilman's The Pharmacological Basis of Therapeutics, 9th Ed., Hardman et al., eds., McGraw-Hill, New York, N.Y., 1996).

For example, with respect to the treatment of CKD or renal fibrosis, a therapeutically effective amount means an amount effective to treat CKD or renal fibrosis, which is an amount effective to reverse, halt, or delay the progress of CKD or renal fibrosis, or to confer protection of kidney from subsequent damage. In one embodiment, a therapeutically effective amount will refer to the amount of a therapeutic agent that decreases the amount of deposition of extracellular matrix in the obstructed kidney by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. The detection of an alteration can be carried out in vitro e.g., using a biological sample or in vivo. A biological sample may be any tissue or fluid from a subject that is suitable for detecting the deposition of extracellular matrix. Examples of useful samples include, but are not limited to, biopsied retinal tissues.

In a further embodiment, a therapeutically effective amount will refer to the amount of a therapeutic agent that improves a patient's kidney function by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. Kidney function may be assessed by any method known in the art, such as by measuring blood urea nitrogen, blood Creatinine levels, Creatinine clearance, or urine Creatinine levels.

In an additional embodiment, a therapeutically effective amount will refer to the amount of a therapeutic agent that decrease the expression or biological function of α-smooth muscle actin (αSMA), type-I collagen, TGF-beta signal pathway components (such as TGF-β1, Smad3, Type II TGF-β receptor), EGFR, PDGFR, STAT3 by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The methods for detecting the expression or biological function of these molecules can be carried out in vivo. For example, imaging techniques (e.g., magnetic resonance imaging, computed axial tomography, single photon emission computed tomography, positron emission tomography, X-ray, ultrasound) may be used in combination with detectably labeled antibodies, ligands, enzymes substrates, etc., to determine the level or function of at least one factor in the TGF-β signaling pathway or signaling pathway related to retinal fibrosis in a subject. Examples of detectable labels include, but are not limited to, radioactive, fluorescent, paramagnetic, and superparamagnetic labels. Any suitable in vivo imaging techniques known in the art may be used in the present invention. Examples of imaging techniques are disclosed in U.S. Pat. Nos. 6,737,247, 6,676,926, 6,083,486, 5,989,520, 5,958,371, 5,780,010, 5,690,907, 5,620,675, 5,525,338, 5,482,698, and 5,223,242.

The detection can also be carried out in vitro, e.g., using a biological sample. A biological sample may be any tissue or fluid from a subject that is suitable for detecting the level or function of at least one factor in the TGF-β signaling pathway or signaling pathway related to retinal fibrosis. Examples of useful samples include, but are not limited to, biopsied kidney tissues, blood, plasma, serous fluid, saliva, urine, and lymph.

Functions that may be measured include, but are not limited to, ligand binding capacity of the receptors, kinase activity of the receptors, phosphorylation of the protein.

The levels of factors in the TGF-β signaling pathway or signaling pathway related to retinal fibrosis. may be measured at the protein or RNA (e.g., mRNA) levels.

Any method known in the art for quantitating specific proteins in a biological sample may be used in the present methods. Examples include, but are not limited to, immunoassays, Western blotting, immunoprecipitation, immunohistochemistry, gel electrophoresis, capillary electrophoresis, column chromatography, ligand binding assays, and enzymatic assays. See, e.g., Harlow et al., Antibodies: A Laboratory Manual, Cold Spring Harbor Laboratory, Cold Spring Harbor, N.Y., (1988); Ausubel et al., Current Protocols in Molecular Biology, John Wiley & Sons, New York 3rd Edition, (1995).

Kit

Also provided herein are kits that further include instructions for administering a composition of the invention to a subject. The kits may also contain detection reagents that specifically test the kidney functions and/or the detection reagents that specifically test the expression or biological function of proteins and/or kinases. The kit may contain in separate containers a protein kinase inhibitor, control formulations (positive and/or negative), and/or a detectable label such as fluorescein, green fluorescent protein, rhodamine, cyanine dyes, Alexa dyes, luciferase, radiolabels, among others. Instructions (e.g., written, tape, VCR, CD-ROM, etc.) for carrying out the assay may be included in the kit.

EXAMPLES

Example 1

Suramin Inhibits Renal Fibrosis in Chronic Experimental Kidney Disease

CKD is the result of various insults to the kidney, affecting approximately 10% of the normal population. Unchecked progression of CKD invariably leads to ESRD and the requirement for renal replacement therapy (dialysis or transplantation). Given the high prevalence of CKD and cost of replacement therapies for ESRD, any treatment that halts or slows the progression of renal fibrosis has the potential to provide an immense medical, social and economical benefit. However prior to the invention, no effective treatments to block renal fibrosis progression had been identified.

The therapeutic application of suramin in obstructive nephropathy was also assessed in this study. The study demonstrated that treatment of cultured renal interstitial fibroblasts with suramin inhibited serum- and transforming growth factor-β1 (TGF-β1)-induced activation of renal interstitial fibroblasts as evidenced by a dose and time-dependent blockade of α-smooth muscle actin (αSMA) and fibronectin. In a mouse model of obstructive nephropathy induced by unilateral urethral obstruction (UUO), administration of a single dose of suramin immediately after UUO injury abolished expression of fibronectin, largely suppressed expression of a-SMA and type I collagen and reduced the deposition of extracellular matrix in the obstructed kidney. Suramin also repressed gene expression of multiple cytokines including TGF-β1 and decreased leukocyte infiltration to the interstitium. Furthermore, suramin suppressed gene expression of Type II TGF-β receptor, blocked phosphorylation of epidermal growth factor and platelet derived growth factor receptors, and inactivated several signaling pathways (Smad2/3, STAT3 and ERK1/2) associated with the progression of renal fibrosis. Therefore, these findings indicate that suramin is a potent anti-fibrotic agent with clinical application for treating patients with CKD.

Suramin is also capable of halting or slowing the progression of renal fibrosis in established tubulointerstitial fibrosis. Studies were carried out to evaluate of delayed administration of suramin on the progression of tubulointerstial fibrosis. Mice were given a single dose of suramin at 20 mg/kg starting at day 3 of obstruction and kidneys were harvested after an additional 7 or 14 days of obstruction. Suramin completely blocked further increase in expression of type 1 collagen and fibronectin and largely suppressed expression of α-SMA in both treatment groups. UUO injury induces phosphorylation of Smad-3, a key mediator of TGF-β signaling, epidermal growth factor receptor, and platelet derived growth factor receptor after 3 days and further increased at 10 days after UUO injury. When suramin was administered at 3 days after obstruction, phosphorylation of these molecules was not further increased in the obstructed kidney. Suramin treatment also inhibited phosphorylation of STAT3 (signal transducer and activator of transcription 3) and extracellular regulated kinase 1 and 2, two signaling pathways associated with renal fibrogenesis. Furthermore, delayed application of suramin suppressed TGFβ1 induced expression of α-SMA and fibronectin in cultured renal interstitial fibroblasts. These results indicate that administration of suramin is effective in attenuating the progression of renal fibrosis after injury and indicate that suramin is useful as an anti-fibrotic treatment in patients with chronic kidney disease.

Tubulointerstitial fibrosis is the final common pathway in late-stage renal disease. The pathogenesis of kidney fibrosis is characterized by overproduction and deposition of extracellular matrix (ECM), which ultimately leads to fibrotic lesions and tissue scarring. Chronic fibrotic kidney disease may progress to the need for renal replacement therapy in end stage of renal disease (ESRD). Given the high prevalence of CKD and cost of replacement therapies for ESRD, any treatment that halts or slows the progression of renal fibrosis has the potential to provide an immense medical, social and economical benefit. Currently, angiotensin-converting enzyme inhibitors (ACEI) and angiotensin II receptor type 1 blockers (ARB) are clinically used to combat renal fibrosis. These drugs, however, are not able to completely stop the progression of renal fibrosis; in some conditions, like aristocholic acid-induced renal fibrosis in rats, they are not effective at all. Since renal fibrogenesis is a complex process that is involved in the activation of multiple cellular and molecular mediators, the incomplete anti-fibrotic effect of ACEI and ARB may be due to their limited targets. As such, an agent that inhibits multiple pro-fibrotic signaling pathways might offer improved therapeutic benefit in fibrotic kidney disease.

Furthermore, the effect of suramin on renal fibroblast activation in normally cultured rat kidney fibroblasts (NRK-49F) and its therapeutic potential in obstructive nephropathy were assessed. In addition, the mechanism by which suramin inhibits renal fibroblast activation and fibrogenesis was also investigated. Current studies demonstrated that suramin treatment completely blocks activation of renal interstitial fibroblasts in vitro and in vivo in a mouse model of obstructed kidneys. Suramin also attenuates renal interstitial matrix deposition and inflammatory responses. Furthermore, delayed administration of a single dose of suramin after UUO injury, inhibits further increase of renal fibrosis as indicated by reduced deposition of extracellular matrix components and expression of type I collagen and fibronectin. These results indicate that suramin treatment not only blocks development of renal fibrosis when given at the early time, but also attenuates the progression of renal fibrosis after a significant degree of tubulointerstitial fibrosis has occurred. There, suramin is an effective anti-fibrotic agent against renal fibrosis and may have potential clinical applications as novel antifibrotic agents for patients with CKD In a rat model of remnant kidney disease, suramin prevented progressive renal injury as demonstrated by inhibiting the rise of 24 hour-proteinuria and serum creatinine, preserving renal tissue architecture and preventing the glomerular and tubulointerstitial damage. Collectively, these findings indicate that suramin is a potent anti-fibrotic agent and may have therapeutic potential in treating patients with fibrotic kidney diseases.

Suramin therefore offers superior advantages over existing therapies. Current drugs including inhibitors of renin/angiotensin system, are not able to completely block the progression. Suramin, on the other hand, was able to halt progressive renal fibrosis in a mouse model and suramin inhibited the progression of renal fibrosis and prevented renal function impairment in a rat model of remnant kidney disease. Thus, suramin is useful for treating patients with CKD.

Materials and Methods

Chemicals and Antibodies. Antibodies to p-STAT3, STAT3, p-Smad2, Smad2, p-Smad3, Smad3, p-ERK1/2, ERK1/2 p-EGF receptor, PDGFβ receptor, cleaved caspase-3, cleaved PARP were purchased from Cell Signaling Technology (Danvers, Mass.). Antibodies to fibronectin, collagen 1 (A2), GAPDH, EGF receptor, p-PDGFβ receptor were purchased from Santa Cruz Biotechnology, Inc. (Santa Cruz, Calif.). Primers were synthesized from Invitrogen (Carlsbad, Calif.). Suramin, antibodies to α-SMA and α-Tubulin, the naphthol AS-D chloroacetate esterase kit, and all other chemicals were from Sigma (St. Louis, Mo.).

Cell Culture and Treatments. NRK-49F cells were cultured in Dulbecco's modified eagle's medium (DMEM) (Sigma-Aldrich, St. Louis, Mo.) containing 5% fetal bovine serum (FBS), 0.5% penicillin and streptomycin in an atmosphere of 5% $CO_2$ and 95% air at 37° C. To determine the effects of suramin on fibroblast activation, suramin was directly added to subconfluent NRK-49F cells and then incubated for the indicated time as described in Figure legends. For TGF-β1 treatment, NRK-49F were starved for 24 h by incubation with 0.5% FBS containing DMEM and then exposed to TGF-β1 (0.5-2 ng/ml) for 24 h.

UUO and Remnant Kidney Models and Suramin Treatment. The UUO model was established in male C57 back mice that weighed 20-25 g (Jackson Laboratory, Bar Harbor, Me.) as described in our previous study. Briefly, the abdominal cavity was exposed via a midline incision and the left ureter was isolated and ligated. The contralateral kidney was used as controls. To examine the efficacy of suramin in renal fibrosis after UUO injury, a single dose of various concentrations of suramin (1, 5, 10, 20 mg/kg) in 50 μl of PBS were intraperitoneally administered immediately after ureteral ligation. The animals were sacrificed and the kidneys were removed at day 7 for protein and mRNA analysis and histological examination. For the time course study, a single dose of suramin (20 mg/kg) was injected and the mice were sacrificed on day 7, or 21 to collect kidneys. Six mice were used in each group. Data from mice treated with suramin (20 mg/kg) for 7 days were shown unless specifically indicated.

The remnant kidney model was created in male Sprague-Dawley rats that weighed 180 to 200 g (Charles River Laboratories, Wilmington, Mass.). 5/6 of normal renal mass was surgically ablated according to our previous protocols. Briefly, 20 animals underwent subtotal nephrectomy involving right subcapsular nephrectomy and infarction of approximately two-thirds of the left kidney by ligation of the posterior and one or two anterior extrarenal branches of the renal artery. In addition, 12 rats underwent a sham operation (laparotomy and manipulation of the renal pedicles). On the second week after surgery, rats were randomly divided into suramin treatment and non-treatment groups. Suramin was given at 10 mg/kg once per week for two weeks. 24-hour urine samples were collected in metabolic cages at day 0 and weekly for the determination of urinary levels of protein. Blood was taken weekly for the measurement of serum creatinine. At 28 days after surgery, mean blood pressure was measured, and then all animals were sacrificed and kidneys were collected for further analysis.

Assessment of Renal Function and Measurement of Blood Pressure. Urinary protein concentrations were determined by using the colorimetric Lowry assay. Serum creatinine was analyzed using a creatinine kit (Sigma). Mean blood pressure was determined via a catheter inserted into the femoral artery attached to the Transonic Systems pressure transducer (Transonic Systems Inc. Ithaca, N.Y.) in anesthetized rats at the end of experiment.

Immunoblot Analysis. Immunoblot analysis of NRK-49F cells and tissue samples were conducted as described previously. The densitometry analysis of immunoblot results was conducted by using NIH Image software (National Institutes of Health, Bethesda, Md.).

Immunofluorescent and Immunohistochemical Staining Immunofluorescent and immunohistochemical staining was performed according to the procedure described in our previous studies. For assessment of renal fibrosis, masson trichrome staining was performed according to the protocol provided by the manufacture (Sigma, St. Louis, Mo.). The collagen tissue area (blue color) was quantitatively measured using Image Pro-Plus software (Media-Cybernetics, Silver Spring, Md., USA) by drawing a line around the perimeter of positive staining area, and the average ratio to each microscopic field (400×) was calculated and graphed.

Quantitative Real-Time PCR. The procedure for quantitative qRT-PCR and the primers used for all measurements have been described previously. Briefly, total RNA from mouse kidney tissue was extracted using RNeasy Kit (QIAGEN, Valencia, Calif.). RNA (1 µg) was reverse transcribed using the AMV First Strand cDNA synthesis kit (Roche Diagnostics Corporation, Indianapolis, Ind.) and random oligodeoxynucleotide primers. Then, real time qRT-PCR amplifications were performed. Relative mRNA abundance was determined from the nanogram ratios of specific mRNA to 18S ribosomal RNA measured in the same samples, and fold change was calculated relative to the group of sham-operated mice with vehicle treatment. Template-free reactions for each pair of primers were also included as controls.

Statistical Analysis. All the experiments were conducted at least three times. Data depicted in graphs represent the means±SEM for each group. Inter-group comparisons were made using one-way analysis of variance (ANOVA). Multiple means were compared using Tukey's test. The differences between two groups were determined by Student t-test. Statistical significant difference between mean values was marked in each graph. P<0.05 is considered significant.

Figure 1E:
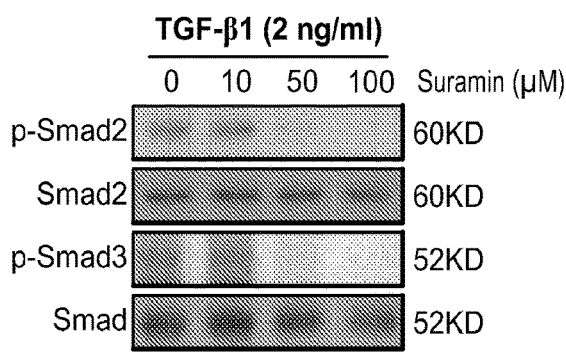
Figure 1F:
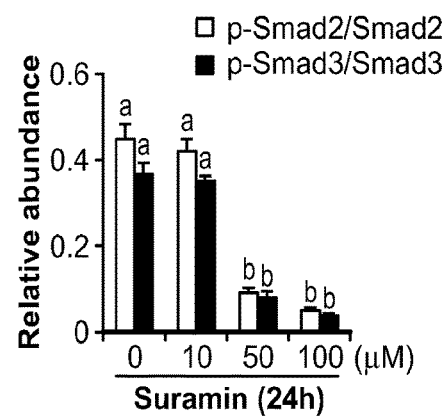

Suramin Blocks TGF-$\beta_1$ and Serum-Induced Expression of α-SMA and Fibronectin in Cultured NRK-49F As TGF-β is a major cytokine that induces transformation of quiescent renal fibroblasts to myofibroblasts through activation of Smad2/3, the effect of suramin on TGF-β1-induced activation of renal fibroblasts and phosphorylation of Smad2 and Smad3 was first examined. FIG. 1A showed the basal level of α-SMA in serum-starved NRK-49F, which did not express fibronectin under starved condition. TGF-β1 treatment dose-dependently increased expression of α-SMA and fibronectin with the maximum induction observed at 2 ng/ml of TGF-β1. In the presence of suramin, TGF-β1-induced fibronectin expression was abolished and α-SMA expression was suppressed to the basal level (compared FIG. 1A, line 1 with 1B, line 4). Suramin treatment also abolished TGF-β1 induced phosphorylation of Smad2 and Smad3 (FIG. 1E, F).

Multiple growth factors are produced and released to the interstitium to stimulate activation of renal fibroblasts during the course of chronic kidney injury. Whether suramin had the potential to inhibit serum-induced activation of renal fibroblasts was next assessed. Upon incubation with 5% FBS, both α-SMA and fibronectin expression was increased in cultured NRK-49F cells. Presence of suramin inhibited their expression in a dose-dependent manner with complete blockade at 100 µM (FIG. 13A,B). Of note, 100 µM suramin did not induce cleavage of poly (ADP-ribose) polymerase (PARP) and caspase-3, two hallmarks of apoptosis, suggesting that it does not cause apoptosis at this concentration. As a positive control, exposure of NRK-49F to 250 µM hydrogen peroxide resulted in cleavage of these two proteins (FIG. 13C).

Collectively, these data indicate that suramin is a potent agent in blocking activation of cultured renal interstitial fibroblasts.

Suramin Inhibits Expression of α-SMA and Fibronectin in the Obstructive Kidney.

Figure 2A:
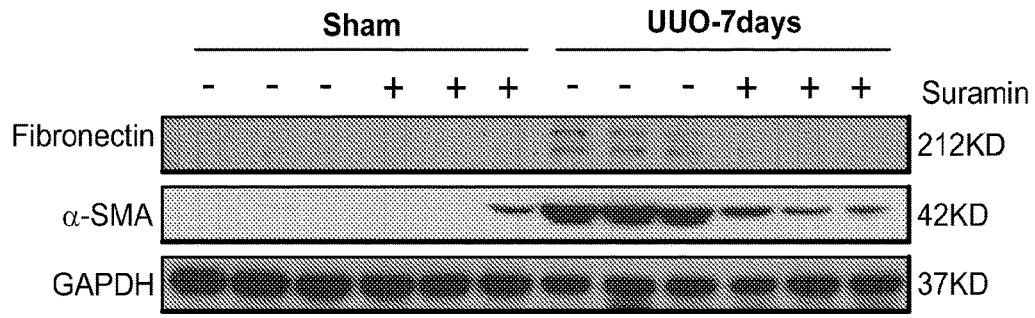
FIG. 2. Effect of suramin on UUO-induced $\alpha$-SMA and fibronectin expression (A) Kidney tissue lysates were subjected to immunoblot analysis with specific antibodies against $\alpha$-SMA, fibronectin or GAPDH. Expression levels of $\alpha$-SMA (B) and fibronectin (C) were quantified by densitometry and normalized with GAPDH. Data are represented as the mean±S.E.M (n=6). Means with different superscript letters are significantly different from one another ($P<0.05$).
Figure 2B:
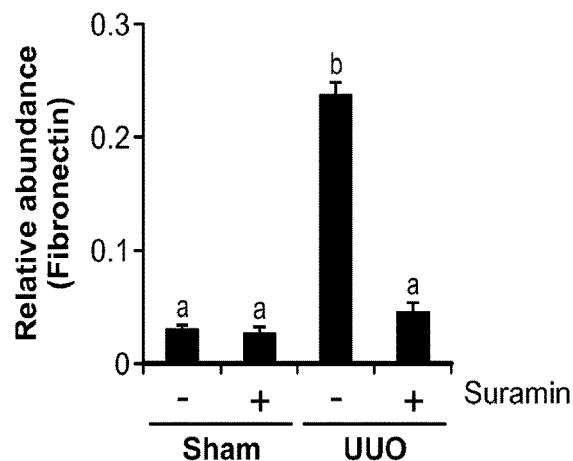
Figure 2C:
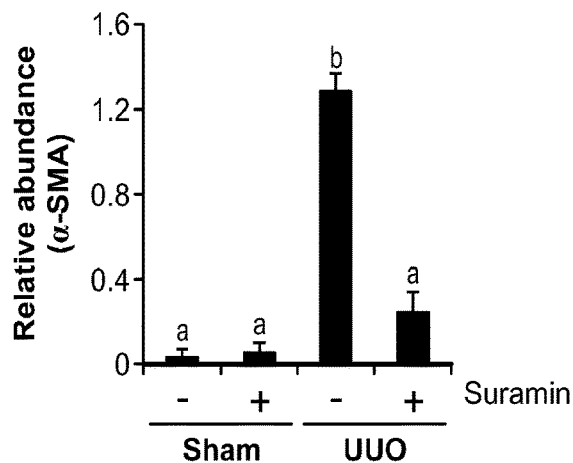

To investigate the ability of suramin in suppressing myofibroblast activation in vivo, the effect of suramin on expression of α-SMA and fibronectin in obstructive nephropathy was examined. Obstructive nephropathy is a model of predominantly tubulointerstitial lesions that are characterized by accumulation and activation of myofibroblasts. As suramin has a half life for at least 21 days, mice were given a single dose of suramin immediately after surgery, and kidneys were collected on day 7 and 21 after the treatment. Western blot analysis of whole kidney lysates indicated increased expression of α-SMA and fibronectin on day 7 that was persistent at day 21 after unilateral urethral obstruction (UUO) injury (FIG. 2, FIG. 15). Suramin administration reduced expression of α-SMA and fibronectin in dose- and time-dependent manners. A slight reduction of their expression was seen when 1 mg/kg was administered, and further inhibition was observed at 5 mg/kg. Administration of suramin 10 mg/kg resulted in complete blockade of fibronectin expression and significant, but incomplete, suppression of α-SMA expression. Increasing the dose of suramin to 20 mg/kg did not further reduce α-SMA expression (FIG. 14). Administration of 20 mg/kg also suppressed expression of α-SMA and fibronectin by approximately 50% at 21 days after UUO injury (FIG. 15). These data, together with FIG. 1, suggest that suramin has a potent capability to inhibit activation of renal interstitial fibroblasts both in vitro and in vivo. A partial suppression of expression of these proteins at 21 days after treatment with suramin might be due to its long half life.

Figure 3A:
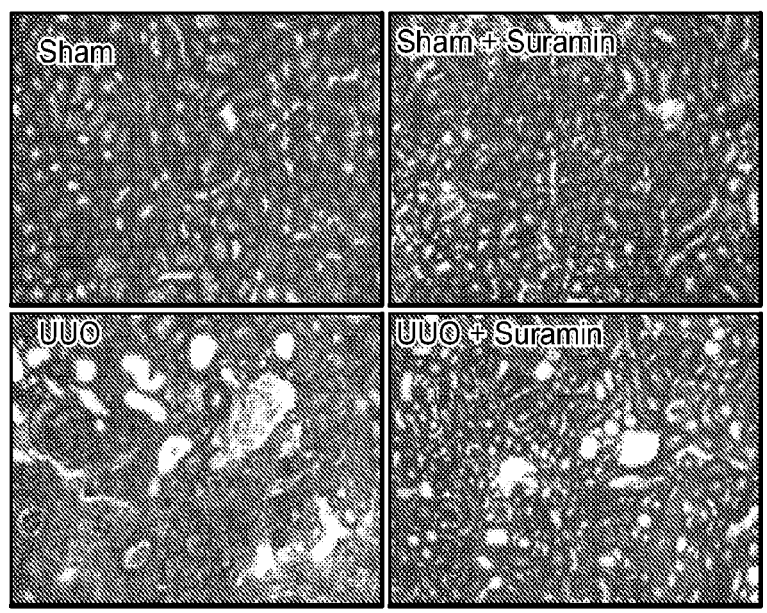
FIG. 3. Effect of suramin on the deposition of ECM and expression of collagen I in obstructive kidneys. (A) Photomicrographs illustrating masson trichrome staining of kidney tissue after various treatments. (B) Kidney tissue lysates were subject to immunoblot analysis with specific antibodies against collagen I, or GAPDH. (C) Expression levels of collagen I were quantified by densitometry and normalized with GAPDH. Data are represented as the mean±S.E.M (n=6). Means with different superscript letters are significantly different from one another ($P<0.05$).
Figure 3B:
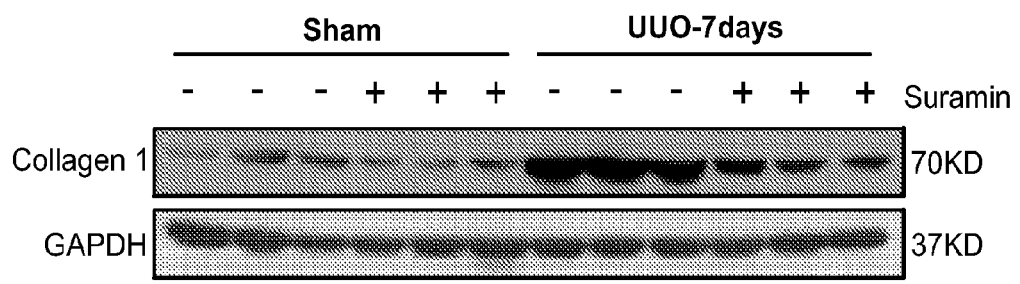
Figure 3C:
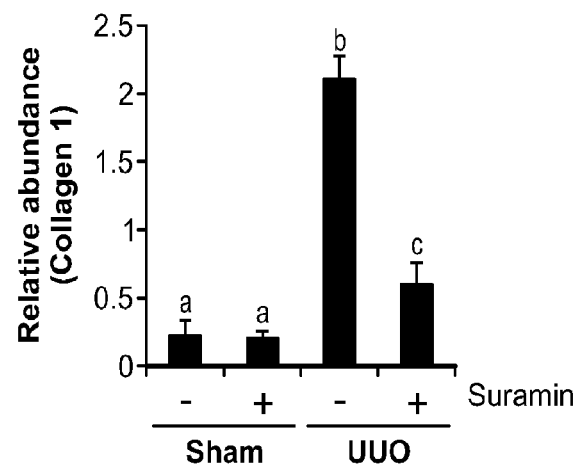

Suramin Attenuates the Progression of Renal Fibrosis and Expression of Collagen 1 After Obstructive Injury Since the major feature of renal fibrosis is increased levels of ECM, the effect of suramin on the expression of interstitial collagen fibrils by using masson trichrome staining was evaluated. As shown in FIG. 3A, kidneys with ureteral obstruction for 7 days displayed severe morphological lesions characterized by tubular dilation with epithelial atrophy, interstitial expansion with collagen accumulation and deposition as evidenced by an increase in trichrome-positive areas within the tubulointerstitium after UUO injury. By contrast, kidneys from animals injected with suramin exhibited an obvious attenuation of these morphological lesions with less fibrosis in the interstitium. As collagen 1 is a major component of the interstitial matrix, expression of collagen 1 was also measured. Collagen 1 expression was upregulated at day 7 after injury, and suramin treatment reduced its expression in a dose-dependent manner with the observed effect at 5 mg/kg. Suramin, at a dose of 10 mg/kg, resulted a greater inhibition, and 20 mg/kg of suramin reduced its expression to the basal level (FIG. 3B, D and FIG. 14). This dose of suramin also partially suppressed collagen 1 expression on day 21 (FIG. 15). These data showed an efficacy of suramin in inhibiting accumulation of ECM proteins after obstructive injury.

Figure 4A:
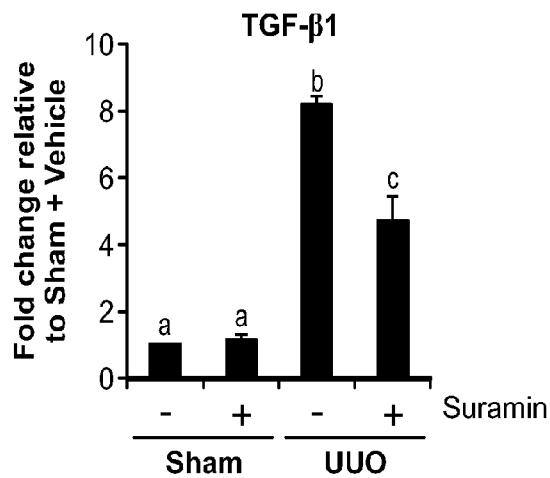
FIG. 4. Effect of suramin on mRNA expression of TGF-$\beta$1 and TGF-$\beta$ receptors. mRNA was extracted from sham-operated or obstructed kidneys of mice administered with/without suramin and subjected to quantitative real-time RT-PCR as described in "Materials and Methods". mRNA expression levels of TGF-$\beta$1 (A), TGF-$\beta$ receptor type I (B), and type II (C) were indicated as fold induction over control (sham-operated mice treated with vehicle). Data are represented as the mean±S.E.M (n=6). Means with different superscript letters are significantly different from one another ($P<0.05$).
Figure 4B:
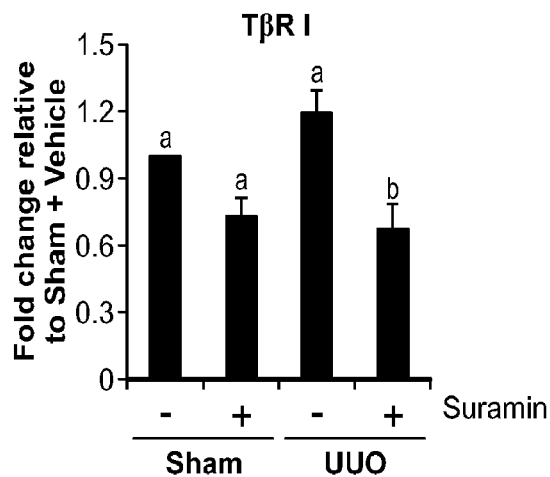
Figure 4C:
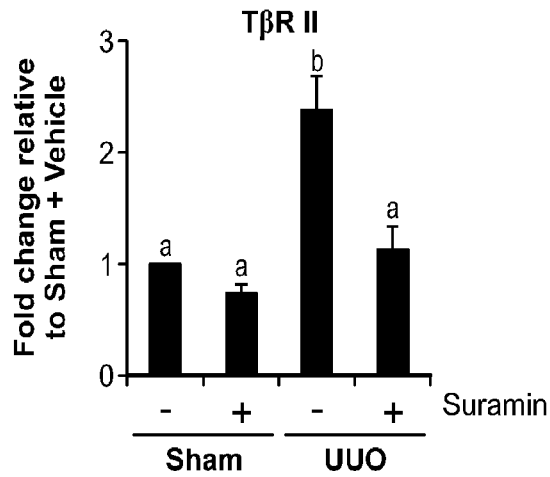

Suramin Inhibits Expression of TGF-β1 and TGF-β Receptor II and Phosphorylation of Smad2/3 in the Obstructive Kidney TGF-β signaling pathway is associated with almost all forms of kidney diseases characterized by interstitial fibrosis, and an increase in the expression of TGF-β and/or its receptors have been considered as a major mechanism of renal fibrosis. The level of expression of TGF-β1 and its type I and II receptors in the obstructed kidneys was measured by quantitative real-time PCR. As shown in FIG. 4, ureteral obstruction markedly induced the expression of TGF-β1 and its type II receptor, and administration of suramin reduced their expression to 45% and 94%, respectively. Although UUO injury did not significantly increased expression of the TGF-β1 type I receptor, suramin treatment suppressed its basal expression in the obstructive kidney.

Figure 5A:
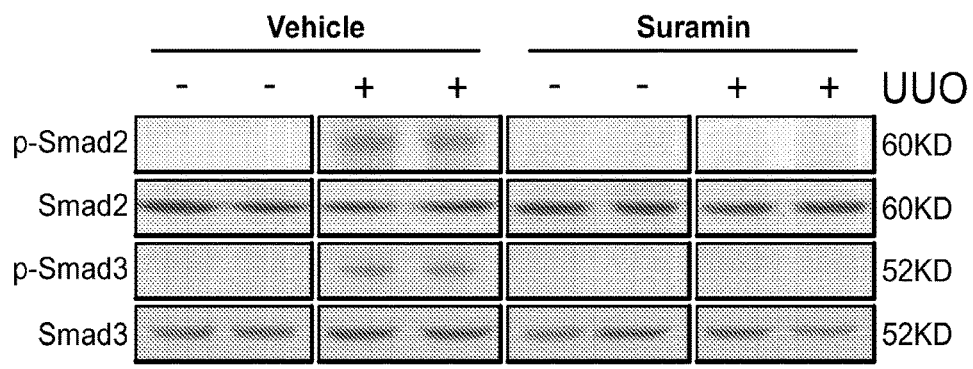
FIG. 5. Effect of suramin on phosphorylation of Smad2 and Smad3.
Figure 5B:
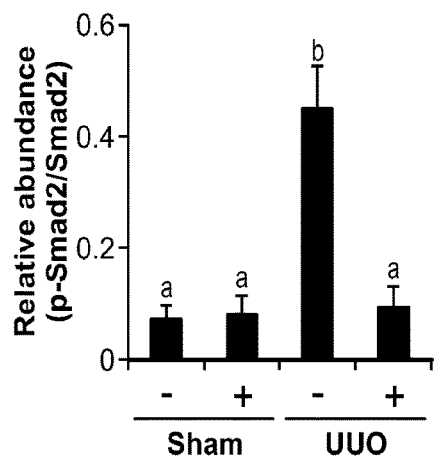
Figure 5C:
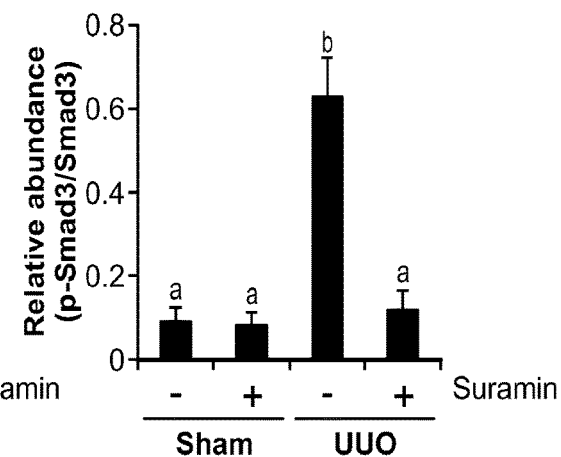
Figure 5D:
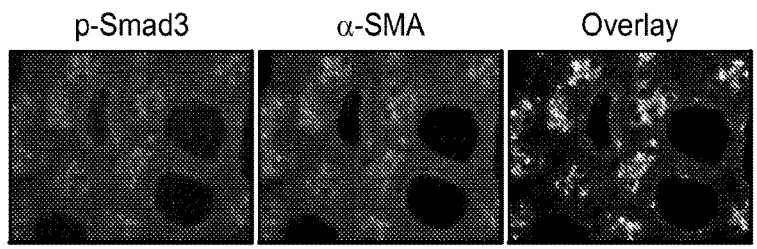
Figure 6A:
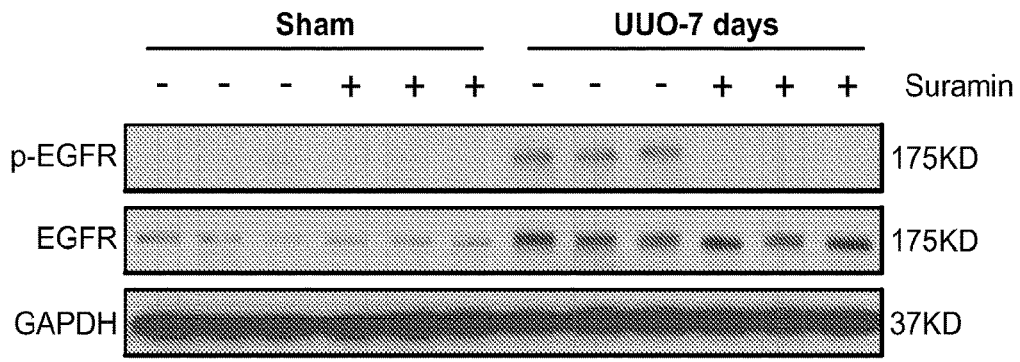
Figure 6B:
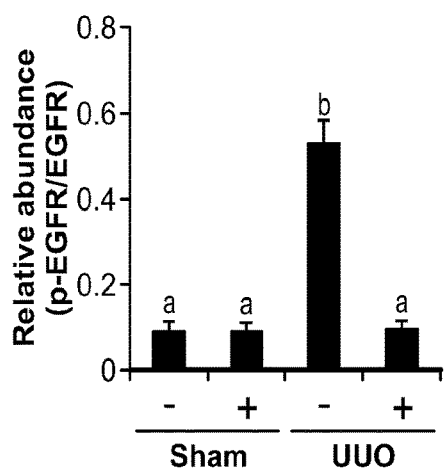
Figure 6C:
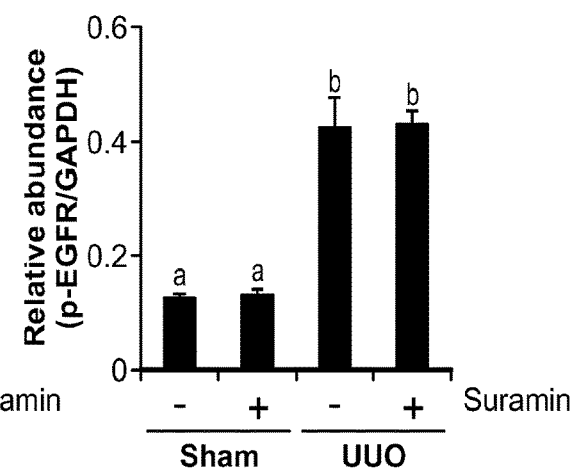
Figure 6D:
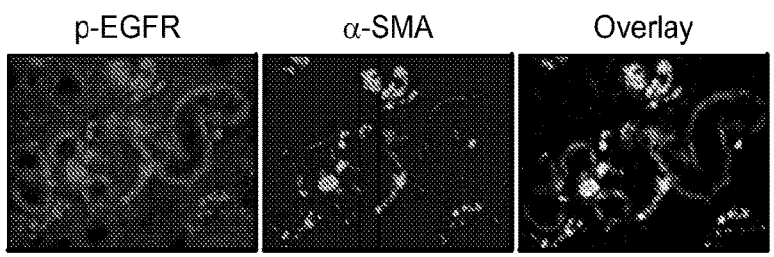

The TGF-β receptor activation triggers phosphorylation and activation of downstream signaling mediators like Smad2 and Smad3. Phosphorylated Smad2/3 subsequently translocates into the nucleus, where it controls the transcription of TGF-β-response genes required for development of fibrosis. Western blot analysis of kidney lysates indicates that UUO injury-induced phosphorylation of Smad2 and Smad3 was abolished upon administration of suramin. Expression of total Smad2 and Smad3 was not affected by UUO injury and suramin (FIG. 5A, B, C). Immunostaining showed that phosphorylated Smad3 is mainly expressed in the interstitial cells as indicated by its co-localization with α-SMA and was also observed, to a lesser degree, in renal tubular cells (FIG. 5D). Taken together, suramin is a potent inhibitor for TGF-β1 signaling.

Figure 7A:
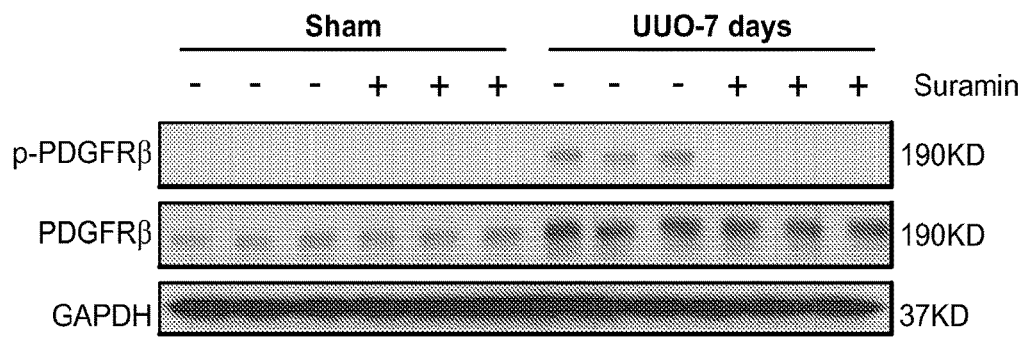
Figure 7B:
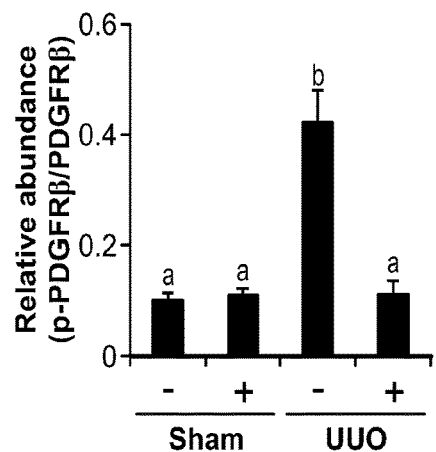
Figure 7C:
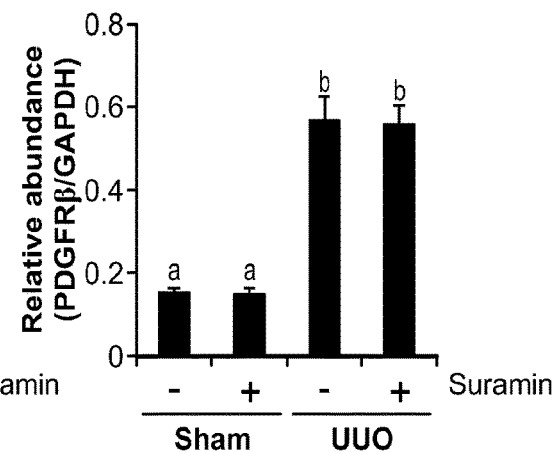
Figure 7D:
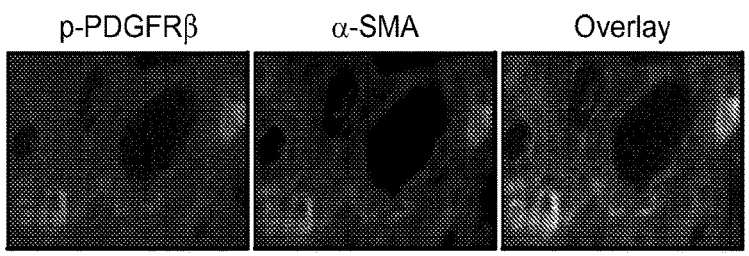

Suramin Suppresses EGF Receptor and PDGF Receptor Phosphorylation in the Obstructive Kidney In addition to TGF-β signaling, activation of EGF and PDGF receptors also contributes to the development/progression of renal interstitial fibrosis. The effect of suramin on the activation of these two receptors was further examined. As shown in FIGS. 6 and 7, increased EGF receptor and PDGF receptor phosphorylation (activation) was detected in the obstructive kidney and suramin treatment abolished this response. UUO injury also increased expression levels of total EGF and PDGF receptors, however, suramin did not have an inhibitory effect on their expression. Phosphorylated EGF receptor was localized in both tubular and interstitial cells. In the latter, the phosphorylated EGF receptor was co-localized with α-SMA (FIG. 6D), suggesting its expression in renal interstitial fibroblasts. As expected, the PDGF receptor was primarily localized in renal interstitial fibroblasts as indicated by its co-localization with α-SMA (FIG. 7D).

Figure 8A:
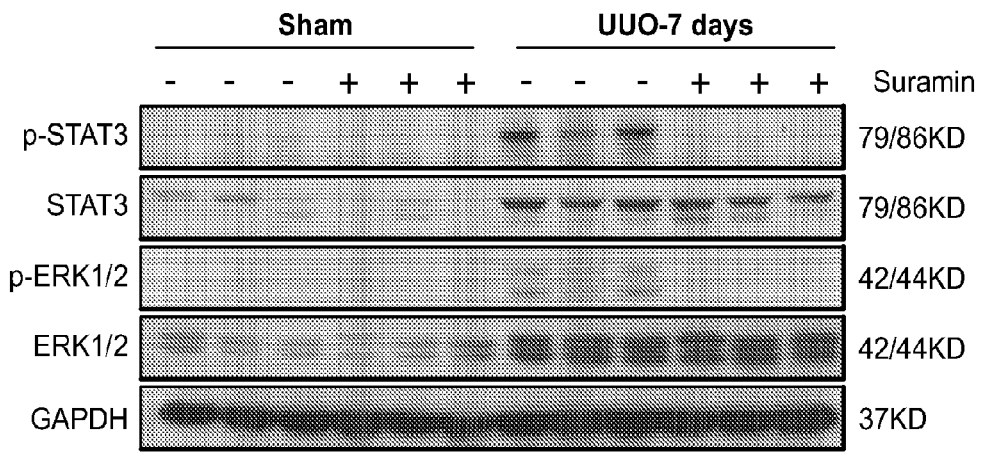
Figure 8B:
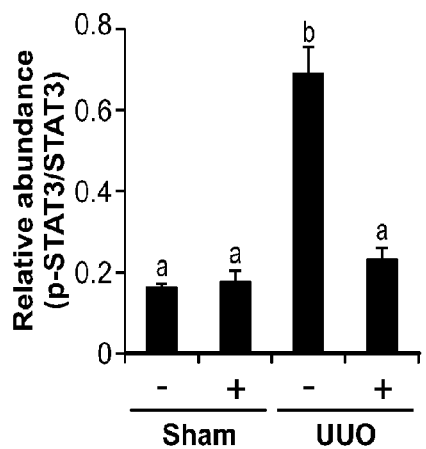
Figure 8C:
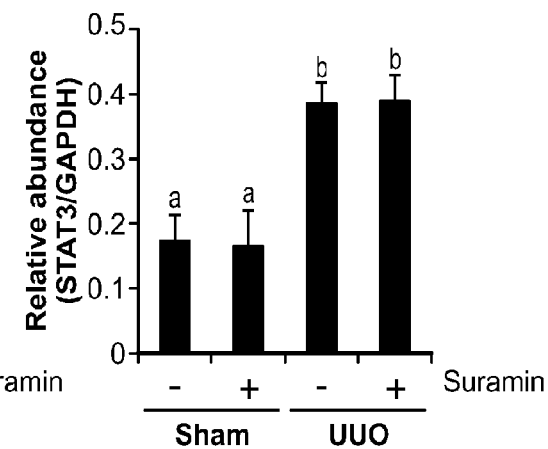
Figure 8D:
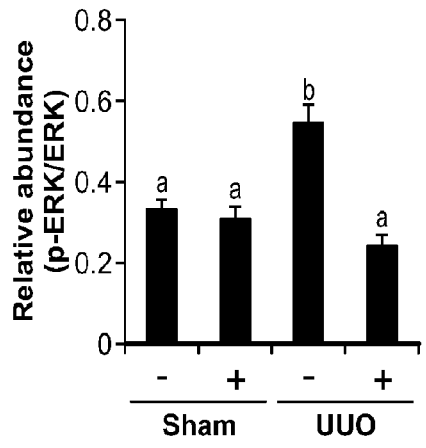
Figure 8E:
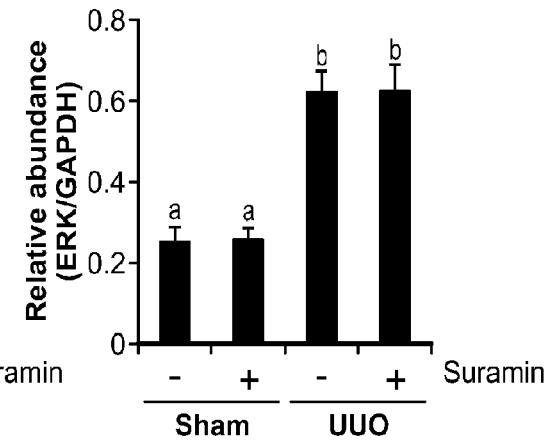
Figure 9A:
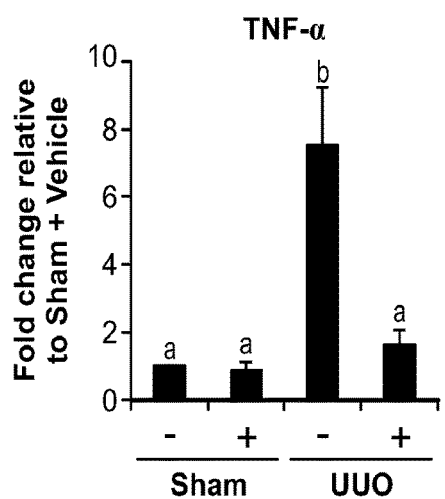
Figure 9B:
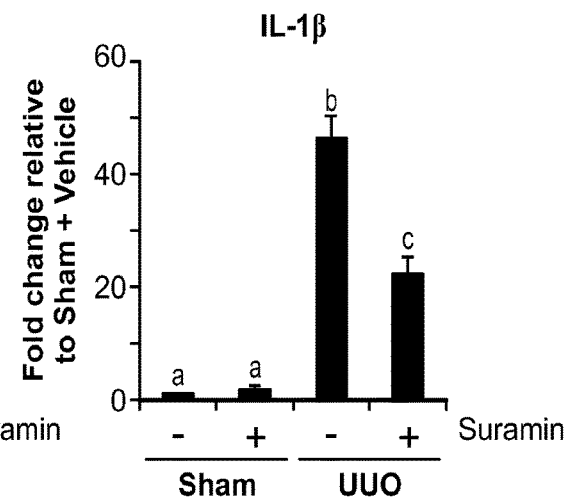
Figure 9C:
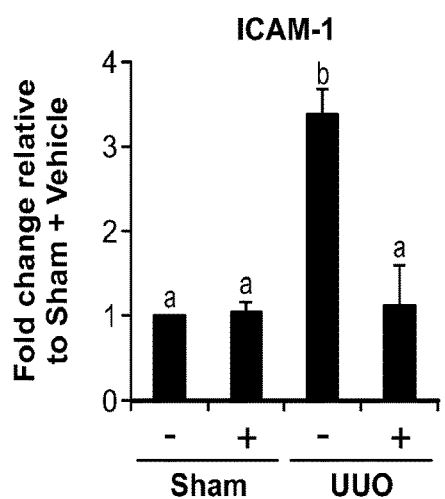
Figure 9D:
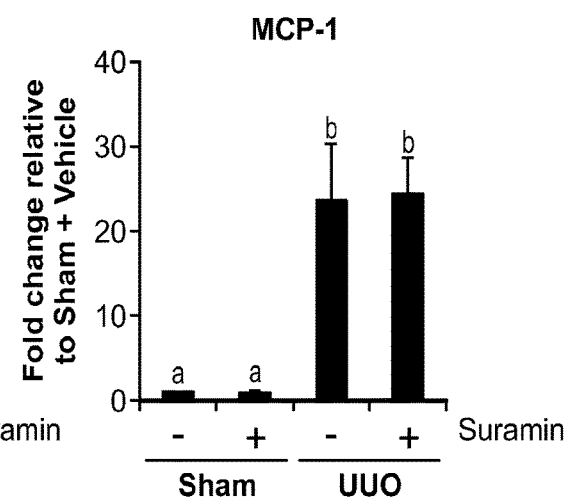
Figure 10A:
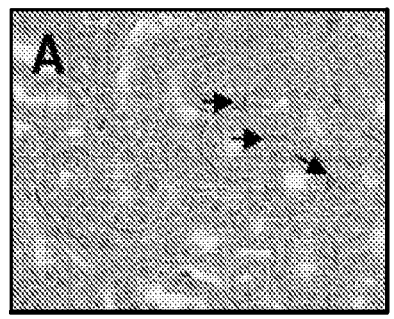
Figure 10B:
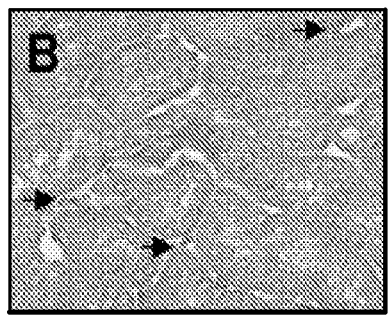
Figure 10C:
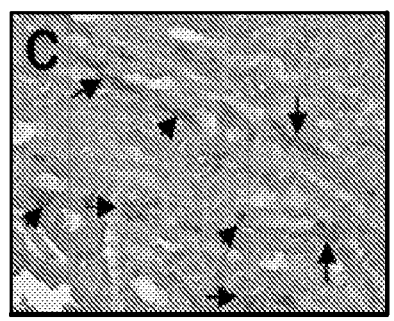
Figure 10D:
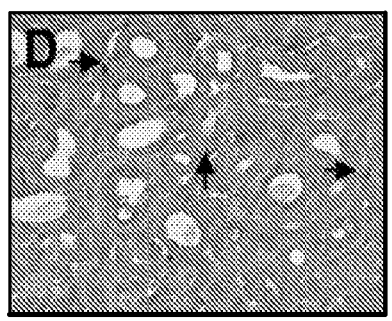
Figure 10E:
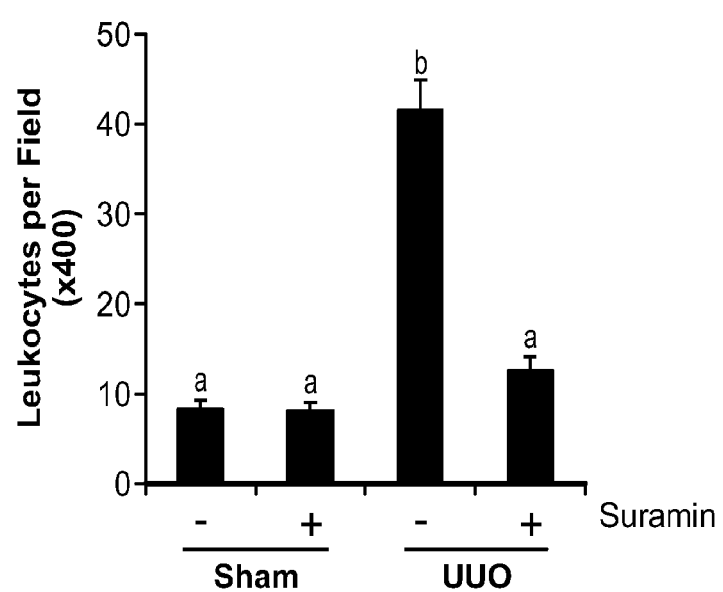

Suramin Inhibits Phosphorylation of STAT3 and ERK1/2 in the Kidney Following Obstructive Injury As a consequence of cytokine/growth factor receptor activation, some intracellular signaling pathways associated with renal fibrosis are activated. Studies from our laboratory and others have shown that STAT3 and ERK1/2 signaling pathways are activated in the obstructive kidney and they are associated with progression of renal fibrosis in the murine model of UUO. We thus sought to determine whether suramin is able to suppress the phosphorylation of these two signaling molecules. As shown in FIG. 8A, phosphorylation of STAT3 and ERK1/2 was barely detected in the sham-treated kidney, but a dramatic increase in activation of those molecules was observed in the obstructive kidney. Suramin treatment abolished phosphorylation of STAT3 and ERK1/2. The expression level of total STAT3 and ERK1/2 was also remarkably increased in UUO injury when compared to normal kidneys. However, suramin did not affect this response.

Suramin Inhibits Phosphorylation of STAT3, ERK1/2, EGFR, PDGFR in Cultured Renal Interstitial Fibroblasts To specifically understand the effect of suramin on phosphorylation of STAT3, ERK1/2, EGFR, PDGFR in renal interstitial fibroblasts, NRK-49F cells were exposed to suramin at different doses. As shown in FIG. 16, phosphorylation of all these kinases was detected in normally cultured NRK-49F cells exposed to serum (5% FBS) and suramin treatment inhibited their phosphorylation in a dose-dependent manner with a complete inhibition at a dose of 100 μM.

Suramin Inhibits Expression of Cytokines in the Kidney Following Obstructive Injury Pro-inflammatory cytokines such as TNF-α, ICAM-1 and MCP-1 are upregulated in the fibrotic kidney22 and contributes to the progression of renal fibrosis. To determine the effect of suramin on expression of these cytokines, we measured their expression levels in the fibrotic kidney of animals treated or untreated with suramin using quantitative real-time PCR. FIG. 9 shows that all these cytokines were increased after obstructive injury; suramin treatment decreased expression levels of TNF-α, IL-1β, ICAM-1, but not MCP-1. These data indicate that suramin selectively regulates expression of proinflammatory factors in the kidney.

Suramin Inhibits Leukocyte Infiltration in the Kidney Following Obstructive Injury We also examined the effect of suramin on leukocyte infiltration in the kidney following obstructive injury. Staining of kidney sections with naphthol-AS-D-chloroacetate esterase showed an increase of neutrophil infiltration in the interstitium and monocytes after obstructive injury. Suramin treatment reduced leukocyte infiltration to basal levels (FIG. 10).

Figure 11A:
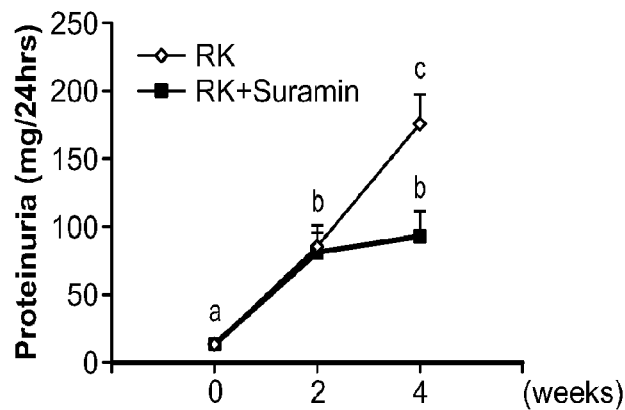
Figure 11B:
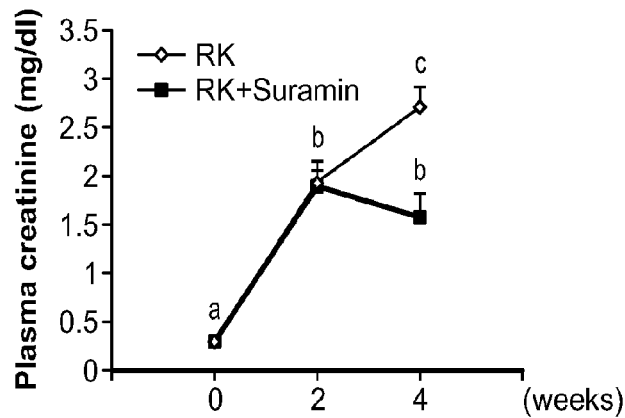
Figure 11C:
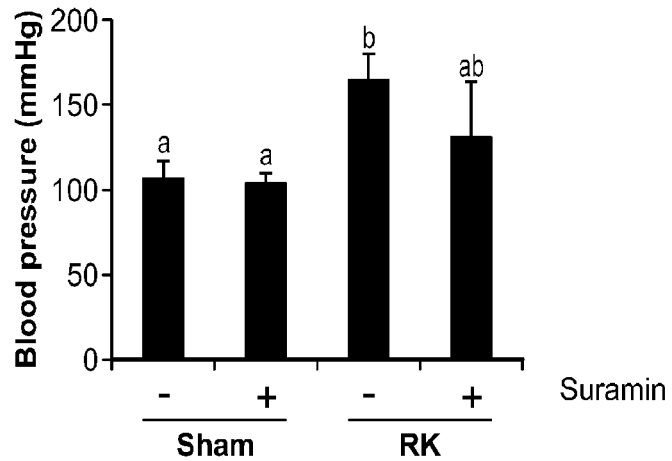

Administration of Suramin Prevents a Rise of Serum Creatinine and Proteinuria and Attenuates the Fibrotic Lesions Following Renal Ablation We further examined the therapeutic potential of suramin in a rat model of remnant kidney disease following 5/6 nephrectomy. Two weeks after surgery, rats developed progressive renal injury as evidenced by the significant increase in 24-hour proteinuria, serum creatinine, and mean blood pressure (FIG. 11A-C). Suramin administration significantly reduced proteinuria and serum creatinine. Hypertension, however, was not significantly affected by suramin. Histological analysis showed the remnant kidney without suramin treatment developed severe tubulointerstitial damage (as shown by tubular atrophy and dilatation and interstitial fibrosis) and glumerular damage (as displayed by severe focal and segmental glomerulosclerosis). In contrast, administration of suramin preserved kidney architecture and prevented the glomerular and tubulointerstitial damage that follows 5/6 nephrectomy. There were no obvious pathological changes in the kidney of both sham and suramin alone-treated animals (FIG. 12). In addition, immunoblot analysis of kidney tissue indicated that suramin administration abolished the de novo expression of α-SMA and fibronectin and increased expression of type 1 collagen in the remnant kidney (FIG. 17). Therefore, suramin is effective in preventing the renal injury progression in rats with remnant kidney independent of changes in blood pressure.

Suramin Inhibits Renal Fibrosis

Suramin is an FDA approved drug for treating trypanosomiaisis and selected malignancies and metastatic diseases and has a broad inhibitory effect on the activation of growth factor/cytokine receptors. Given the fact that numerous cytokines and growth factors are involved in activation of renal interstitial fibroblasts and progression of tubulointerstitial scarring, inhibition of a single receptor/signaling pathway may not completely block these processes. In this study, we examined the effect of suramin on the activation of renal interstitial fibroblasts and the progression of renal fibrosis. We demonstrated that suramin treatment blocks activation of renal interstitial fibroblasts in vitro and in vivo in animal models of chronic kidney disease. Suramin also reduces renal interstitial matrix deposition and inflammatory responses after UUO injury. Further, suramin inhibited the progression of renal fibrosis and prevented renal function impairment in a rat model of remnant kidney disease. These findings indicate that suramin is an effective agent against renal fibrogenesis.

A key investigation was that administration of a single dose of suramin effectively inhibited activation of renal fibroblasts and attenuated the development of renal fibrosis at 7 and 21 days after UUO injury. This is in contrast to most inhibitors, which need daily administration to achieve their inhibitory effects. Such a long-term effect of suramin may be due to its accumulation in the kidney and long half-life in the body. Suramin was reported to be mostly accumulated in the kidney after injection and has a half-life of 21 days. The actual concentration of suramin in the kidney may be higher than in the blood and that a low dose would result in a therapeutic effect. Indeed, we observed that suramin at 5 mg/kg, a dose that is 6-fold lower than the dose used for treating patients with tumors (usually 30 mg/kg), decreased expression of α-SMA and fibronectin, and suppressed expression of collagen 1 and deposition of ECM. At 10 mg/kg, suramin also prevented the rise of 24-hour proteinuria and serum creatinine, blocked activation of renal interstitial fibroblasts, and attenuated renal fibrosis and glomerular damage in the remnant kidney disease. However, suramin administration did not significantly lower blood pressure in this hypertensive kidney disease model, suggesting that it exerts those renoprotective effects through a mechanism independent of changes in blood pressure.

The anti-fibrotic actions of suramin may be through multiple mechanisms. As the up-regulation of both TGF-β1 and its receptors is an early event preceding the onset of significant renal fibrosis, we first examined the effect of suramin on their expression and activation of TGF-β1 signaling in the model of UUO. Our studies clearly indicated that suramin treatment suppressed the expression of both TGF-β1 and TβRII and blocked phosphorylation of Smad2 and Smad3. Smad2 and Smad3 are two key downstream signaling mediators of TGF-β pathways, and their phosphorylation reflects activation of TGF-β receptors. As such, our results reveal that suramin not only inhibited expression of TGF-β1 and TβRII but also blocked their interaction in the obstructive kidneys. In support of this, we demonstrated that suramin blocked exogenous TGF-β-induced activation of renal fibroblasts and phosphorylation of Smad2 and Smad3 in cultured NRK-49F. As Smad2/Smad3 plays a critical role in transducing TGF-β signaling to induce expression of numerous profibrotic genes, the inhibition of renal fibrosis by suramin may be mediated, in part, by the suppression of TGF-β1 axis in the obstructed kidneys.

Inactivation of growth factor receptors may also be associated with the anti-fibrotic actions of suramin. EGF and PDGF receptors are implicated in the pathogenesis of renal fibrosis. In this study, we demonstrated that suramin administration abolished phosphorylation of both EGF and PDGF receptors in the obstructive kidney as well as in the cultured renal interstitial fibroblasts. This action of suramin is important because activation of the EGF receptor not only mediates fibrogenesis stimulated by its ligands but also mediates the fibrogenic effects of many metabolic, hormonal, and hemodynamic factors in chronic kidney disease (CKD) through a mechanism of transactivation. For example, angiotensin II-induced renal fibrosis was blocked by overexpression of a dominant negative isoform of EGFR in mice; endothelin-induced renal vascular and glomerular fibrosis was attenuated by EGF receptor inhibitors. Moreover, tubulo-interstitial lesions after ischemic renal injury can also be reduced by functional inactivation of the EGF receptor. Although the PDGF receptor cannot transduce the fibrotic signal from other substances, it is a major growth factor receptor expressed in the fibroblast and critically involved in the progression of renal interstitial fibrosis. Furthermore, PDGF is able to stimulate protein synthesis and secretion of TGF-β1 in human renal proximal tubular cells. Therefore, inhibition of these two receptors by suramin may have an additive or synergic therapeutic effect with inhibition of TGF-β1-smad signaling in attenuation of progression of renal fibrosis. The anti-fibrotic effect of suramin may not be limited to its inhibition on those receptors. Suramin is also a potent inhibitor for purinergic receptors and SIP receptors. The development of renal fibrosis after UUO injury and of hepatic fibrosis after bile duct ligation is associated with P2X7 and S1P receptors. Therapeutic intervention optionally includes inhibition of these two receptors in the kidney.

Inflammation is an important mechanism in initiation and maintenance of renal damage, and decreased inflammatory response results in attenuation of renal fibrosis. The data indicate that suramin treatment suppresses expression of multiple cytokines, including TNFα, IL-β1 and ICAM-1 and leukocyte infiltration, indicating that inhibition of the inflammatory response is also one of the mechanisms by which suramin attenuates renal fibrosis. TGF-β1 and other growth factors can activate injured tubular cells and immune system cells to produce inflammatory cytokines and unleash an inflammatory response, which in turn activates tubule cells, fibroblasts, and myofibroblasts to produce ECM, and amplifies fibrosis and tubular damage. Therefore, the beneficial effect of suramin may be mediated primarily by its ability to block activation of TGF-β and/or growth factor receptors and consequent inactivation of the STAT3 signaling pathway. This hypothesis is supported by our recent observations that the pharmacologic blockade of STAT3 signaling inhibited expression of all those inflammatory mediators and by our present data showing that suramin abolished phosphorylation of Smad2/3, EGF and PDGF receptors, and STAT3.

STAT3 and ERK1/2 are two pathways that are activated by different receptors and are involved in numerous events related to renal fibrosis. In particular, STAT3 is a transcriptional factor that can directly bind to the promoter region of TGF-β1 and induces activation of its promoter activity in vitro. Our recent studies showed that UUO injury led to the activation of STAT3 and administration of S31-201, a selective inhibitor, decreased activation of renal interstitial fibroblasts and reduction of expression of both TGF-β1 and TGF type II receptor as well as TNF-α, IL-β and ICAM1 and leukocyte infiltration. Thus, inactivation or inhibition of STAT3 mediates the anti-fibrotic action of suramin. Suramin was found to abolish phosphorylation of STAT3 in the obstructive kidney and in cultured renal interstitial fibroblasts. Optionally, a STAT3 inhibitor is co-administered or administered in conjunction with suramin. In an alternative approach, a STAT3 inhibitor is administered alone (see Example 3). In addition, we found that suramin also abolished renal ERK1/2 phosphorylation after UUO injury. As ERK1/2 activation has been reported to contribute to tubular apoptosis in the murine model of UUO, inactivation of the ERK1/2 pathway by suramin may reduce tubular atrophy, a degenerative response after tubular death. Therefore, inhibition of the STAT3 and ERK1/2 signaling pathways may be involved in the anti-fibrotic effect of suramin in obstructive nephropathy.

It has been documented that suramin administration in humans causes some non-specific adverse effects when cytotoxic doses of suramin (yielding >200 μM plasma concentrations) were used. The most common side effects of suramin are polyneuropathy, allergic skin rash, anemia, fatigue and nausea/vomiting. However, recent studies showed that administration of a low dose of suramin (10 mg/kg, twice/per week) that yields 10-20 μM plasma concentrations enhances the anti-tumor effect of some anticancer drugs and is well tolerated by patients. Since effective doses of suramin in our studies were 5-10 mg/kg, suramin attenuates renal fibrosis without causing obvious adverse effects. Nonetheless, treatment of chronic fibrotic kidney disease needs a long duration of drug administration.

In summary, we demonstrate for the first time that suramin inhibits activation of renal fibroblasts and prevents development and progression of renal interstitial fibrosis and glomerulosclerosis in animal models of chronic kidney disease. These anti-fibrotic effects of suramin are associated with inactivation of multiple cytokine/growth factor receptors and signaling pathways as well as inhibition of inflammatory responses. As suramin inhibits renal fibrosis at low doses that have been safely used in human diseases, it hold a therapeutic potential for treatment of patients with CKD.

Example 2

Delayed Administration of Suramin Attenuates the Progression of Renal Fibrosis in Obstructive Nephropathy In Example 1, suramin treatment was shown to prevent the onset of renal fibrosis in a model of obstructive nephropathy induced by unilateral ureteral obstruction (UUO). In this study, we further assessed the effect of delayed administration of suramin on the progression of tubulointerstitial fibrosis. Mice were given a single dose of suramin at 20 mg/kg starting at day 3 of obstruction and kidneys were harvested after an additional 7 or 14 days of obstruction. Suramin completely blocked further increase in expression of type 1 collagen and fibronectin and largely suppressed expression of α-smooth muscle actin (α-SMA) in both treatment groups. UUO injury induces phosphorylation of Smad-3, a key mediator of transforming growth factor-β (TGF-β) signaling, epidermal growth factor receptor, and platelet derived growth factor receptor after 3 days and further increased at 10 days after UUO injury. When suramin was administered at 3 days after obstruction, phosphorylation of these molecules was not further increased in the obstructed kidney. Suramin treatment also inhibited phosphorylation of STAT3 (signal transducer and activator of transcription 3) and extracellular regulated kinase 1 and 2, two signaling pathways associated with renal fibrogenesis. Furthermore, delayed application of suramin suppress TGF-β1 induced expression of α-SMA and fibronectin in cultured renal interstitial fibroblasts. These results indicate that administration of suramin is effective in attenuating the progression of renal fibrosis after injury and suggest the potential clinical application of suramin as an anti-fibrotic treatment in patients with chronic kidney disease.

Materials and Methods

Animals and the UUO Model. The UUO model used was described above. The abdominal cavity was exposed via a midline incision and the left ureter was isolated and ligated. Sham-operated animal received the same surgical procedures but without ureter ligation. To establish the time course of renal fibrogenesis in this model, four groups of mice (n=5) were killed at days 1, 3, 7, and 14, respectively, after left ureter ligation. To examine the effect of suramin on the progression of renal fibrosis, Suramin was administered on day 3 after obstruction: Groups I and II were sham-operated or UUO mice killed at 3 days after surgery; Groups III and IV were mice that underwent UUO injury and were given either vehicle or suramin from day 3 to day 10 (1 week); and Groups V and VI were mice that underwent UUO injury and given either vehicle or suramin from day 3 to day 17 (two weeks). A single dose of suramin (20 mg/kg) was administered by intraperitoneal injection. Control mice were injected with the equal volume of vehicle (0.9% saline). At the end of the experiments, mice were killed and the kidneys were removed. One part of the kidneys was fixed in 10% phosphate-buffered formalin for histological studies. Another part was snap-frozen in liquid nitrogen and stored at −80° C. for protein extractions.

UUO Injury Induces Expression of Collagen 1, Fibronectin and α-SMA in a Time Dependent Manner Renal fibrosis is characterized by overproduction of ECM proteins that include type 1 collagen and fibronectin and by activation of renal interstitial fibroblasts. As the first step toward understanding the effect of delayed administration of suramin on renal fibrosis, we examined expression of type 1 collagen and fibronectin over time after obstructive injury. As shown in FIG. 19, basal levels of fibronectin were not detected in the sham-operated animals. After ureteral obstruction, fibronectin was detectable on day 3, but significantly increased on day 7 and further elevated on day 14. In contrast, an abundance of type 1 collagen was expressed in the sham-operated kidneys and its expression was increased on day 3 and further elevated on day 7 and 14 after obstruction. To confirm the above observation, we also examined interstitial ECM deposition by Masson trichrome staining. An increase in Masson trichrome positive staining was observed within the tubulointerstitial area on day 3 after UUO injury and these areas were expanded over time from 7-14 days (FIG. 20A).

Figure 19A:
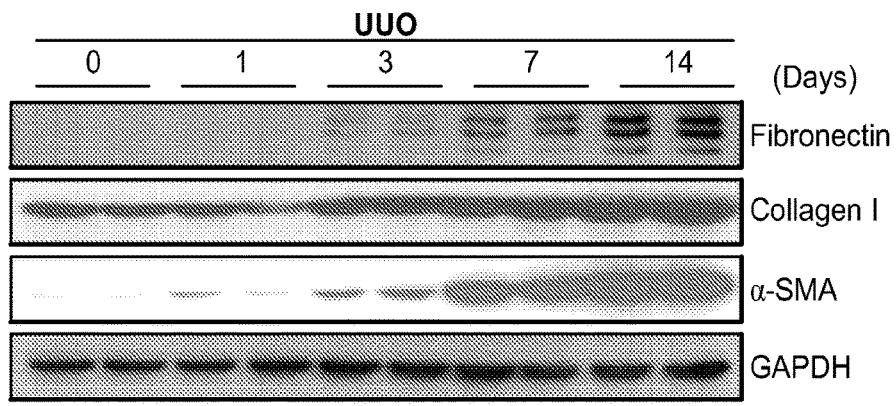
Figure 19B:
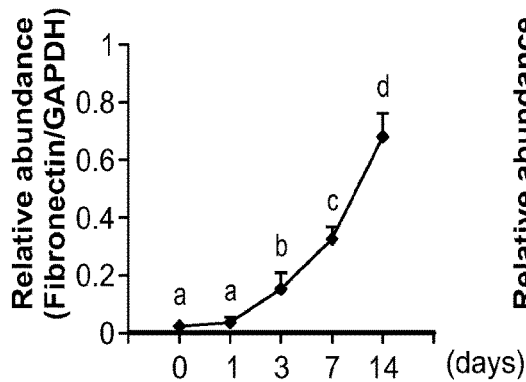
Figure 19C:
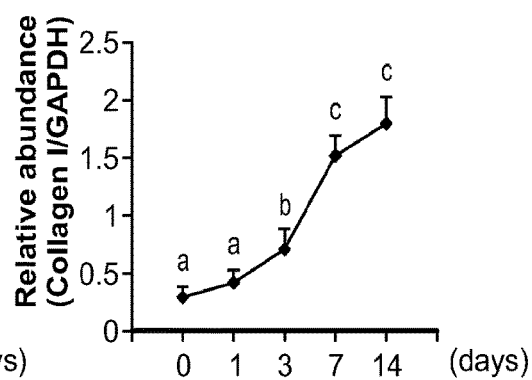
Figure 19D:
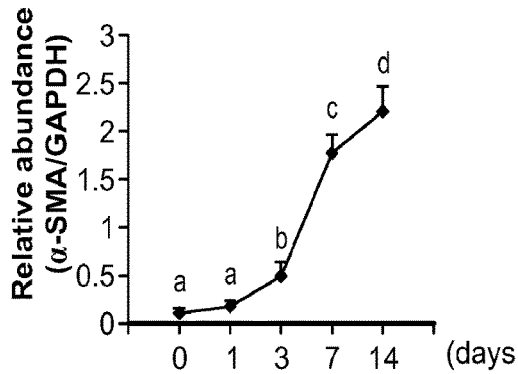

Myofibroblasts are the principal cells known to be responsible for accumulation and deposition of the interstitial matrix and characterized by expression of α-smooth muscle actin (α-SMA). We also examined its kinetic expression after UUO injury. As shown in FIGS. 19A and D, α-SMA was barely detected in the sham-operated kidney. Obstructive injury induced increase in expression of α-SMA on day 3, and further increased on day 7 and day 14 after obstruction. Quantitative determination of Western blot analysis showed that induction of α-SMA expression level was increased up to 5-fold at day 3 after obstructive injury and about 30- and 48-fold increase of α-SMA expression was observed on day 7 and day 14, respectively.

Effect of Delayed Administration of Suramin (Starting 3 Days after Obstruction) on the Progression of Renal Fibrosis To compare the therapeutic effect of suramin on the progression of renal fibrosis, we decided to start suramin treatment at day 3 after UUO injury. After treatment with suramin for 7 and 14 days, mice were sacrificed, respectively and kidneys were removed to assess the deposition of extracellular matrix (ECM) by Masson trichrome staining and expression of type I collagen and fibronectin by immunoblot analysis.

An increase in Masson trichrome-positive areas was observed within the tubulointerstitium 3 days after the onset of obstruction and further increased at 10 days of obstruction. The obstructed kidneys of mice treated with suramin starting at day 3 after UUO showed a decrease in Masson trichrome-positive areas. Semiquantitative analysis revealed a 2.2-fold increase in Masson trichrome-positive areas in the obstructed kidney on day 10 compared with that on day 3. In the obstructed kidney treated with suramin, Masson trichrome-positive areas were reduced on day 10 to a level similar to that in the kidney at 3 days of obstruction (FIG. 20A, B). Similar results were also obtained in the kidney treated for 14 days staring from day 3 and ending at day 17 after onset of obstruction. Consistent with these results, immunoblot analysis showed that administration of suramin at day 3 of obstruction also reduced collagen 1 and fibronectin expression to the starting levels in both 7- or 14-day treatment groups (FIGS. 20 and 22). Suramin treatment in those two groups also reduced α-SMA expression (FIGS. 21 and 22). These data suggest that suramin is a potent inhibitor that blocks the progression of renal fibrosis after injury.

Effect of Delayed Administration of Suramin on UUO-Induced Phosphorylation of Smad-3

To examine the mechanism involved in the anti-fibrotic effect of suramin when administered after UUO induction, we first analyzed the effect of suramin on the activation of smad-3, a key mediator of TGFβ signaling. FIG. 23 shows that after UUO injury, the phosphorylation level of smad-3 was increased at day 3 and further increased at day 10. Treatment with suramin at 3 days after UUO injury largely blocked Smad3 phosphorylation. These data indicate that suramin is able to inhibit the activation of TGF-β signaling when given after obstruction.

Figure 24A:
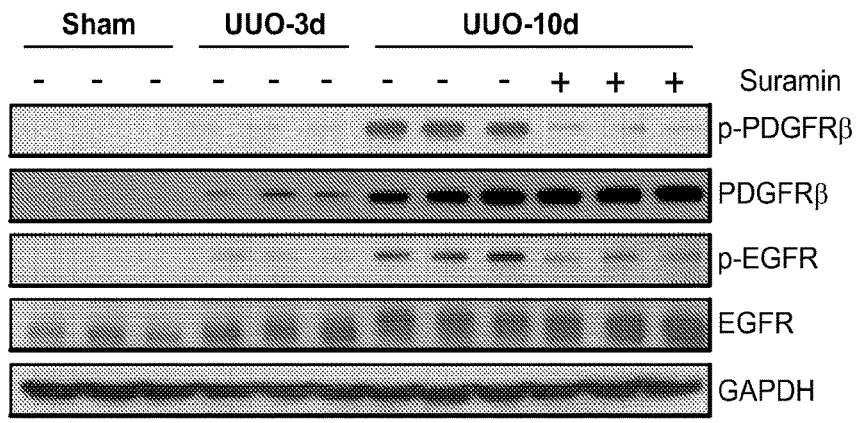
Figure 24B:
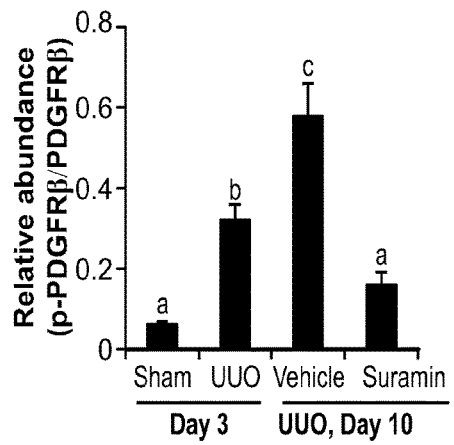
Figure 24C:
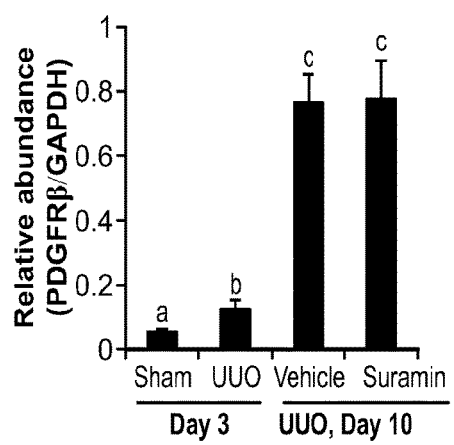
Figure 24D:
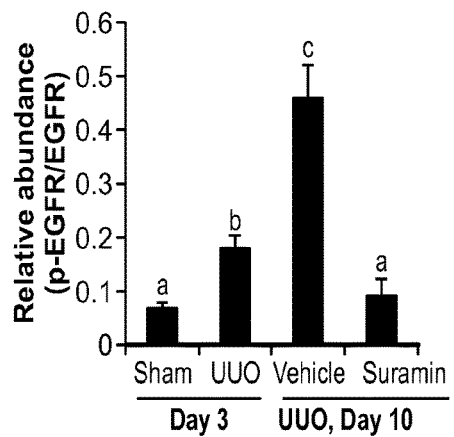
Figure 24E:
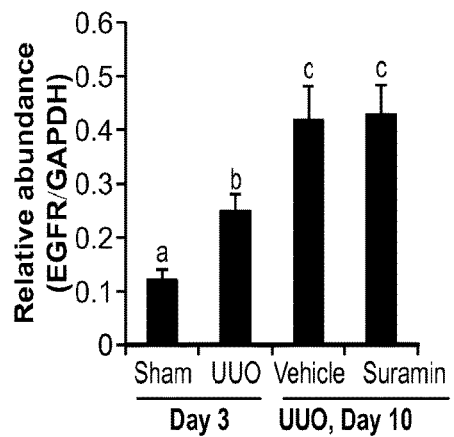

Effect of Delayed Administration of Suramin on Phosphorylation of EGFR and PDGFR in the Obstructed Kidney Since activation of EGFR and PDGFR also contributes to renal fibrosis, we further examined the effect of suramin on the phosphorylation of EGFR and PDGFR. At day 10 after surgery, the obstructed kidney showed a significant increase in the phosphorylation of EGFR and PDGFR compared to the obstructed kidney at day 3. Administration of suramin at day 3 of obstruction resulted in a significant reduction of EGFR and PDGFR phosphorylation (FIG. 24A, B, D). Although UUO injury also induced an increase in expression of total EGFR and PDGFR, these expression levels were not affected by suramin (FIG. 24A, C, E). These data suggest that delayed administration of suramin blocks UUO injury-induced phosphorylation of both EGFR and PDGFR in the obstructive kidney.

Figure 25A:
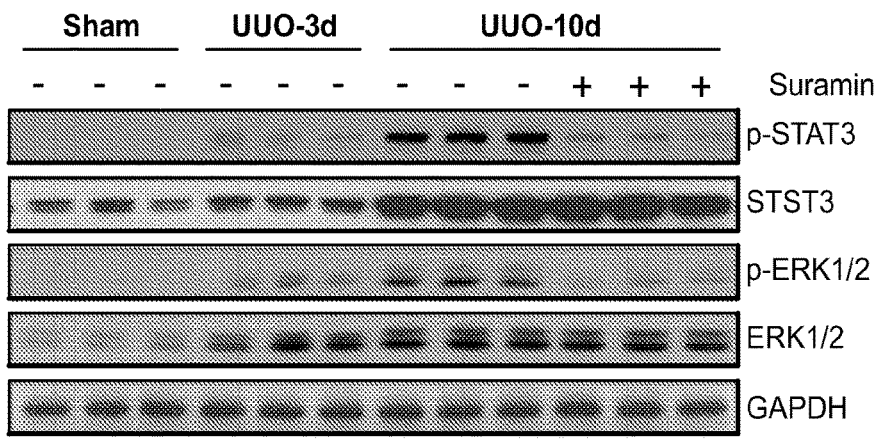
Figure 25B:
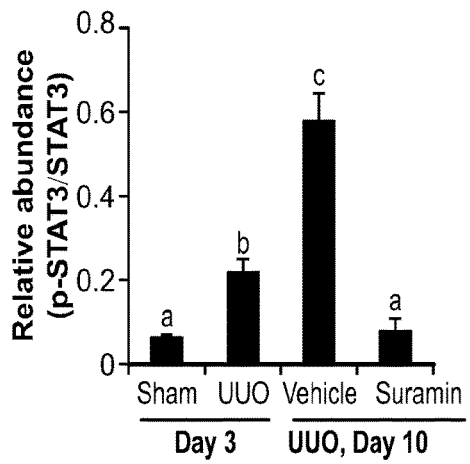
Figure 25C:
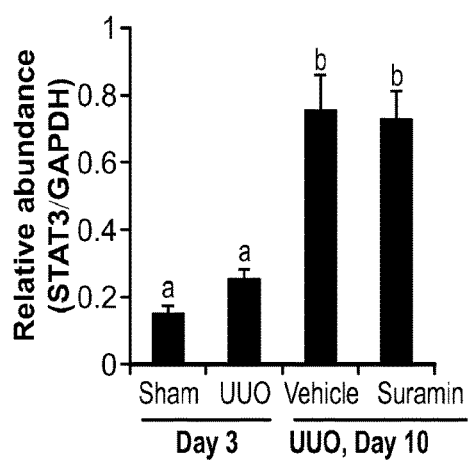
Figure 25D:
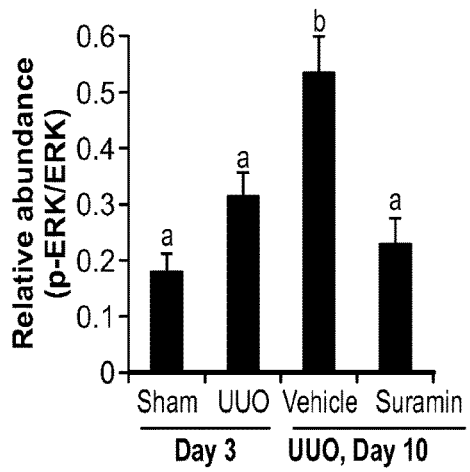
Figure 25E:
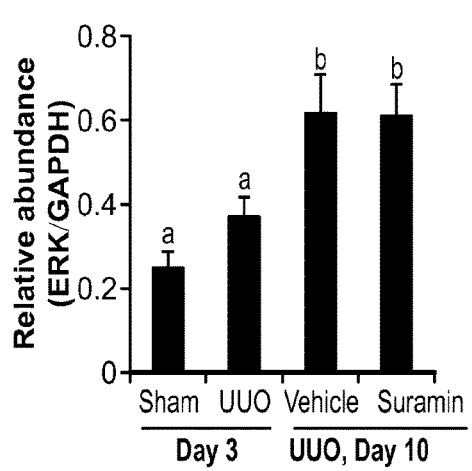

Effect of Delayed Administration of Suramin on Phosphorylation of STAT3 and ERK1/2 in the Obstructive Kidney Activation of STAT3 and ERK1/2 is associated with renal fibrosis and is downstream of multiple membrane receptors including EGFR and PDGFR. We thus analyzed their phosphorylation state by immunoblot analysis in kidney tissue. As shown in FIG. 25, UUO injury induces phosphorylation of both STAT3 and ERK1/2 after 3 days and further increased at 10 days after UUO injury. When suramin was administered at 3 days after obstruction, their phosphorylation was not further increased (FIG. 25A, B, D). Although UUO injury also increased total protein levels of these two molecules, suramin treatment did not alter their expression levels. These data indicate that suramin is able to suppress the activation of these cellular signaling pathways after UUO injury.

Delayed Treatment with Suramin Inhibits Expression of Fibronectin and α-SMA in Cultured Renal Interstitial Fibroblasts To demonstrate the inhibitory effect of suramin on activation of renal interstitial fibroblasts in vitro, we designed a treatment scheme to mimic in vivo situations as described in this study (FIG. 26A). NRK-49F were pretreated with TGF-β1 for 24 and 48 h, and then exposed to suramin (100 μM) for additional 24 and 48 h in the continuous presence of TGF-β1. At 48 h after pretreatment with TGF-β1, expression of α-SMA and fibronectin was induced, which is similar to the in-vivo situation. TGF-β1 further increased expression of these two proteins in the absence of suramin, however, delayed treatment with suramin suppressed further increase of these two proteins. These data indicate that delayed administration of suramin is effective in suppressing activation of renal interstitial fibroblasts induced by TGF-β1.

Suramin Inhibits Progression of Renal Fibrosis

Suramin is effective in preventing the onset of renal fibrosis in a model of obstructive nephropathy when given immediately after surgical ligation of the ureter. The data described herein demonstrate that delayed administration of a single dose of suramin after UUO injury, inhibits further increase of renal fibrosis as indicated by reduced deposition of ECM components and expression of type I collagen and fibronectin. Collectively, these results indicate that suramin treatment not only blocks development of renal fibrosis when given at the early time, but also attenuates the progression of renal fibrosis after a significant degree of tubulointerstitial fibrosis has occurred.

The mechanism by which delayed administration of suramin attenuates renal fibrosis is not fully understood. As α-smooth muscle actin (α-SMA)-positive myofibroblasts are the principal effector cells responsible for ECM overproduction in the fibrotic kidney, we examined the effect of suramin on their activation in vivo and in vitro. Our data show that suramin administrated at day 3 after UUO injury largely reduced expression of α-SMA in vivo and suramin treatment also inhibited TGF-β1 induced expression of α-SMA in cultured NRK-49F cells, suggesting that blockade of renal fibroblast activation may be a critical step for suramin to inhibit the deposition of ECM proteins and the progression of renal fibrosis. However, since our studies showed that suramin inhibits the expression of ECM proteins to a greater degree than inhibition of α-SMA expression, suramin may also inhibit the production and deposition of ECM proteins through a mechanism independent of renal fibroblast activation. Further studies need to examine the effect of suramin on the expression of ECM proteins in different renal cell types.

Progression of renal fibrosis is a complicated process with a variety of cellular and molecular mediators interacting in concert. Studies have shown that activation of EGFR and PDGR as well as TGF-β signaling play a prominent role in this process. As such, we examined the effect of delayed suramin treatment on activation of these signaling pathways. Our data clearly show that starting suramin treatment at day 3 after injury inhibited the phosphorylation of Smad-3 to the level at the initial time of injury. Also, suramin equally inhibits phosphorylation of EGFR, PDGFR, STAT3 and ERK1/2 in UUO injured animals. Therefore, the inhibition of those receptors and signaling pathways may account, at least in part for the anti-fibrotic effect of suramin observed after UUO injury. Nevertheless, suramin is an inhibitor with broad specificity and also inhibit other membrane receptors such as purinergic receptor $P2X_7$ and sphingosine-1-phosphate (S1P) receptors. Blockade of these receptors by suramin may contribute to its anti-fibrotic effects.

The incidence and prevalence of CKD is increasing worldwide. Unchecked progression of CKD invariably leads to ESRD and the requirement for renal replacement therapy (dialysis or transplantation). The primary aims of treatment in patients with CKD are both to prevent, or at least slow, progression of CKD. But available therapies are limited and include inhibitors of renin/angiotensin system. However, these drugs are not able to completely block the progression. Here we have shown that suramin is able to halt progressive renal fibrosis in a mouse model when given early after UUO injury. Suramin inhibited the progression of renal fibrosis and prevented renal function impairment in a rat model of remnant kidney disease. Suramin is therefore useful for treating patients with CKD.

In summary, our data demonstrate that suramin is effective in blocking subsequent renal fibrosis after the emergence of established fibrosis. The anti-fibrotic effect of suramin is associated with inhibition of several cellular signaling pathways associated with renal fibrosis. As ESRD is preceded, in nearly all cases, by the progressive development of renal fibrosis, delayed administration of suramin may have therapeutic potential by halting or at least slowing the development of fibrosis.

Example 3

S3I-201, a Novel STAT3 Inhibitor, Inhibits Renal Interstitial Fibroblast Activation and Attenuates Renal Interstitial Fibrosis in Obstructive Nephropathy Chronic kidney disease is characterized by accumulation of interstitial myofibroblasts and production of excessive amounts of extracellular matrix proteins. In this study, we examined the effect of S3I-201, a novel inhibitor of STAT3, on the activation of renal interstitial fibroblasts and the progression of renal fibrosis. In cultured rat renal interstitial fibroblasts, S3I-201 treatment inhibited the activation of renal interstitial fibroblasts as evidenced by dose- and time-dependent blocking of α-smooth muscle actin and fibronectin expression. In a mouse model of renal interstitial fibrosis induced by unilateral ureteral obstruction, STAT3 was activated, and administration of S3I-201 inhibited STAT3 activation and attenuated extracellular matrix protein deposition after obstructive injury. S3I-201 was effective in reducing infiltration of inflammatory cells and suppressing obstructive injury-induced protein expression of fibronectin, α-smooth muscle actin and collagen type 1, as well as gene expression of multiple cytokines. Furthermore, S3I-201 inhibited proliferation and induced apoptosis preferentially in renal interstitial fibroblasts in the obstructed kidney. These results indicate that increased STAT3 activity mediates activation of renal interstitial fibroblasts and the progression of renal fibrosis and that inhibition of STAT3 signaling with S3I-201 is useful for treatment of fibrotic kidney diseases.

STAT3 Inhibitors

The primary aims of treatment in patients with CKD are both to prevent, or at least slow, progression of CKD. Studies were carried out to evaluate the effect of S3I-201, a novel STAT3 (signal transducer and activator of transcription) inhibitor, on renal fibroblast activation in normally cultured rat kidney fibroblasts. We also assessed its therapeutic potential in obstructive nephropathy. Treatment of cultured renal interstitial fibroblasts with S3I-201 inhibited serum-induced activation of renal interstitial fibroblasts as evidenced by a dose and time-dependent blockade of αSMA and fibronectin. In a mouse model of obstructive nephropathy induced by unilateral urethral obstruction (UUO), administration of S3I-201 after UUO injury abolished expression of fibronectin, largely suppressed expression of a-SMA and type I collagen and reduced the deposition of extracellular matrix in the obstructed kidney. S3I-201 also repressed gene expression of multiple cytokines including TGF-β1 and decreased leukocyte infiltration to the interstitium. Furthermore, S3I-201 suppressed gene expression of Type II TGF-β receptor. Therefore, these findings indicate that S3I-201 is a potent anti-fibrotic agent with clinical applications for treating patients with CKD.

Any treatment that halts or slows the progression of renal fibrosis has the potential to provide an immense medical, social and economical benefit. Currently, angiotensin-converting enzyme inhibitors (ACEI) and angiotensin II receptor type 1 blockers (ARB) are clinically used to combat renal fibrosis. These drugs, however, are not able to completely stop the progression of renal fibrosis; in some conditions, like aristocholic acid-induced renal fibrosis in rats, they are not effective at all. Since renal fibrogenesis is a complex process that is involved in the activation of multiple cellular and molecular mediators, the incomplete anti-fibrotic effect of ACEI and ARB may be due to their inhibition of unimportant targets or pathways associated with renal fibrogenesis. As such, it is necessary to search for novel agents that target a critical pro-fibrotic signaling molecule/pathway.

STAT3 is a transcriptional factor that can be induced by multiple growth factors and cytokines such as TGF-β1, platelet-derived growth factor, and IL-6 that contribute to the development of renal fibrosis. Increased expression of activated STAT3 was detected in several kidney diseases associated with progressive fibrosis, including glomerulonephritis and diabetic nephropathy. STAT3 acts as a common mediator in chronic renal damage.

The incidence and prevalence of CKD is increasing worldwide. Unchecked progression of CKD invariably leads to ESRD and the requirement for renal replacement therapy (dialysis or transplantation). Current drugs including inhibitors of renin/angiotensin system, are not able to completely block the progression. We found that S3I-201 is able to halt progressive renal fibrosis. Thus, this inhibitor is useful for treating patients with CKD. S3I-201 is able to halt the progression of renal fibrosis in animal models when given either prior to the injury or in the established renal fibrosis, S3I-201 or other STAT3 inhibitors may therefore has the potential to develop as anti-fibrotic drug to treat chronic kidney diseases and other diseases associated with fibrosis.

S3I-201

S3I-201 is a selective inhibitor of STAT3 that has been synthesized and used to treat tumors. S3I-201 preferentially inhibits STAT3 DNA-binding activity and diminishes STAT3 tyrosine phosphorylation. In this study, we evaluated the therapeutic effect of S3I-201 on activation of renal interstitial fibroblasts in vitro using rat NRK-49F, a rat renal interstitial fibroblast line, and the progression of renal fibrosis in a murine model of the fibrotic kidney induced by UUO injury. Furthermore, we investigated the effect of S3I-201 on expression of some cytokines associated with the development of progressive renal fibrosis.

Materials and Methods

Chemicals and antibodies. S3I-201 was purchased from Calbiochem (La Jolla, Calif.). Antibodies to p-STAT3, p-STAT1, p-STAT3, p-STAT5, and β-catenin were purchased from Cell Signaling Technology (Dancers, Mass.). Anti-fibronectin was purchased from BD transduction Laboratory (Lexington, Ky.). Primers were synthesized from Invitrogen (Carlsbad, Calif.). STAT3 siRNA and silencer negative control siRNA were purchased from Invitrogen. Antibodies to α-SMA) and α-tubulin, the naphthol AS-D choroacetate esterase kit, and all other chemicals and blocks were from Sigma (St. Louis, Mo.).

Cell culture and treatments. NRK-49F cells were cultured in Dulbecco's modified eagle's medium (DMEM) (Sigma-Aldrich, St. Louis, Mo.) containing 10% fetal bovine serum (FBS), 0.5% penicillin and streptomycin in an atmosphere of 5% $CO_2$ and 95% air at 37° C.

Transfection of siRNA into cells. The siRNA oligonucleotides targeted specifically to STAT3 (200 pmol) were transfected into NRK-49F cells ($1\times10^6$) using the Amaxa Cell Line Nucleofector Kit T (Lonza Cologne AG, Cologne, Germany) and the Amaxa Nucleofector device according to the manufacturer's instructions (Gaithersburg, Md.).

Unilateral urethral obstruction (UUO) model and S3I-201 treatment. The UUO model was established in male C57 black mice that weighed 20-25 g (Jackson Laboratory, Bar Harbor, Me.) as described previously. The contralateral kidneys were used as controls. To examine the efficacy of S3I-201 in renal fibrosis after UUO injury, S3I-201 (10 mg/kg) in 50 μl of dimethyl sulfoxide (DMSO) was intraperitoneally administered to mice immediately after ureter ligation and then given daily for 6 or 13 days. Mice were randomized into 4 groups with 6-7 mice in each group as follows: (1) sham injury with DMSO as vehicle; (2) sham injury with S3I-201; (3) UUO injury with DMSO; (4) UUO injury with S3I-201.

Western blot analysis and Sirius red and immunofluorescent staining were carried out according to standard methods.

Quantitative real-time PCR. Real time qRT-PCR amplifications were performed in 20 μl reactions. The amplification protocol was as follows: denaturation for 10 minutes and enzyme activation at 95° C., 40 cycles of 95° C.×10 sec, 59° C.×30 sec, and 72° C.×20 sec, followed by one step annealing at 72° C. for 5 minutes. Relative mRNA abundance was determined from the ratios of specific mRNA to 18S ribosomal RNA measured in the same samples, and fold change was calculated relative to the group of sham-operated mice with vehicle treatment.

ELISA. Protein levels of TGF-β1, TNF-α, and IL-1β in kidney homogenates were determined using specific sandwich enzyme immunometric assay kits, ELISA Ready-SET-Go (eBioscience, Inc. San Diego, Calif.) as described previously. The results were normalized by total protein content in kidney homogenates.

In situ TUNEL assays. Terminal deoxynucleotidyl transferase biotin-dUTP nick end-labeling (TUNEL) staining was used to detect DNA strand breaks using a detection kit, according to the instructions provided by the manufacturer. The number of TUNEL-positive nuclei per field was evaluated in five fields per section and five sections per kidney.

Statistical analysis. All the experiments were conducted at least three times. Data depicted in graphs represent the means±SEM for each group. Multiple means were compared using Tukey's test. The differences between two groups were determined by Student t-test. Statistical significant difference between mean values was marked in each graph. $P<0.05$ is considered significance.

S3I-201 Decreases Expression of α-SMA and Fibronectin in Cultured Renal Interstitial Fibroblasts Myofibroblasts are active fibroblasts characterized by expression of α-SMA and fibronectin. To understand whether STAT3 activation is required for activation of renal interstitial fibroblasts, we examined the effect of S3I-201 on expression of α-SMA and fibronectin in NRK-49F. As shown in FIG. 27A-D, both α-SMA and fibronectin were highly expressed in NRK-49F cells, indicating that the cultured renal interstitial fibroblasts are phenotypically myofibroblasts. Incubation of cells with S3I-201 dramatically decreased the expression of α-SMA and fibronectin in a dose- and time-dependent manner, suggesting that STAT3 mediates activation of renal interstitial fibroblasts.

Figure 27A:
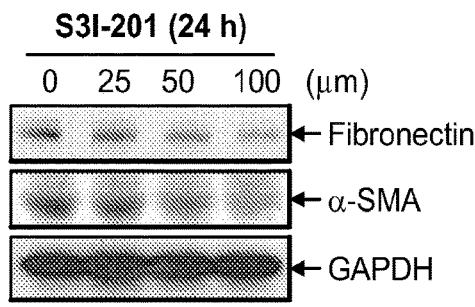
Figure 27B:
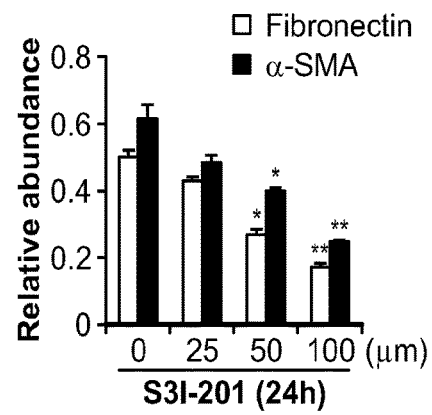
Figure 27C:
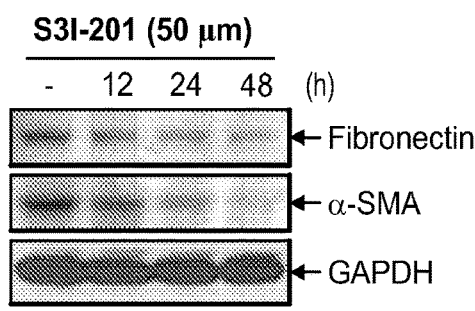
Figure 27D:
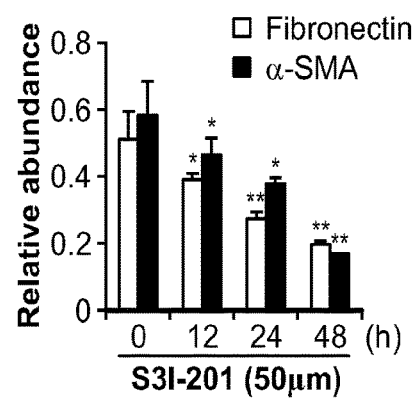
Figure 27E:
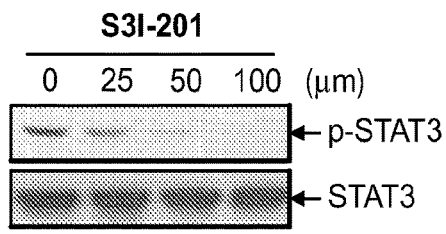
Figure 27F:
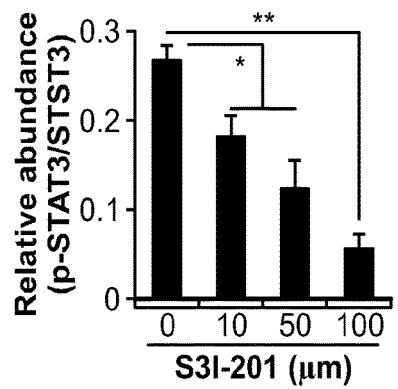

STATs are activated by tyrosine phosphorylation. p-STAT3 and p-STAT5, but not p-STAT1 were constitutively expressed in cultured NRK-49F cells. Treatment with S3I-201 dose-dependently inhibited the expression of p-STAT3 with a complete inhibition at 100 μM (FIG. 27E, F). S3I-201 treatment did not affect STAT5 phosphorylation but increased expression of p-STAT1 in a dose dependent fashion (FIG. 37). These data indicate that S3I-201 is a highly selective inhibitor of STAT3 and is able to block expression of the constitutively activated STAT3 in renal interstitial fibroblasts. Furthermore, STAT3 may negatively regulate STAT1 activation. Since recent studies have documented that both STAT1 and STAT5 play a role in suppression of tissue fibrosis, in contrast to STAT3, increased expression of p-STAT1 and preservation of p-STAT5 may be beneficial to the alleviation of renal fibrosis after injury.

Down-Regulation of STAT3 by siRNA Inhibits Expression of α-SMA and Fibronectin in Cultured Renal Interstitial Fibroblasts To confirm the role of STAT3 in mediating α-SMA and fibronectin expression in NRK-49F cells, siRNA targeting STAT3 was transfected to NRK-49F by electroporation to down-regulate STAT3 and expression of α-SMA and fibronectin was examined by immunoblot analysis, FIG. 28 demonstrates that knock down of STAT3 decreased expression of α-SMA and fibronectin in NRK-49F (FIG. 28). These data support our conclusions that STAT3 is critically involved in activation of cultured renal interstitial fibroblasts.

STAT3 Phosphorylation and Expression in the Obstructive Kidney

Figure 29A:
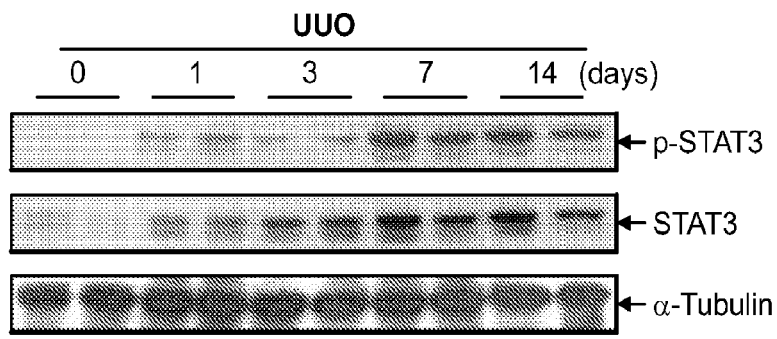
Figure 29B:
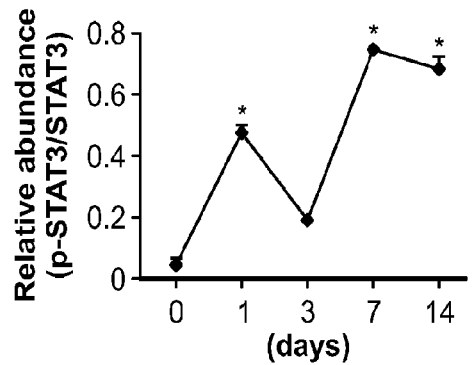
Figure 29C:
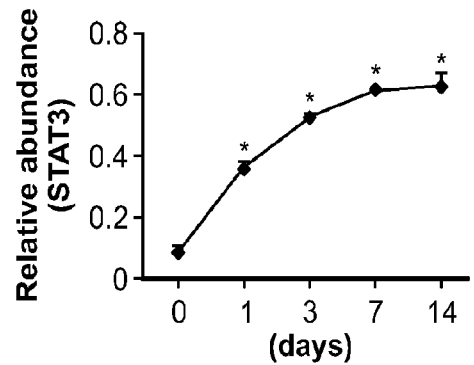

Based on the above observation, we hypothesized that STAT3 plays an essential role in mediating the development of renal interstitial fibrosis in vivo. To test this hypothesis, we first examined the activation and expression of STAT3 in obstructive nephropathy, a model of predominantly tubulointerstitial lesions that are characterized by accumulation and activation of myofibroblasts. As shown in FIGS. 29A and B, the basal level of STAT3, but not p-STAT3, was observed in sham-operated kidneys. UUO injury caused STAT3 tyrosine phosphorylation, which evolves in two waves: the first on day 1, and the second on day 7. STAT3 tyrosine phosphorylation then remained elevated until at least 14 days after UUO injury. Whereas p-STAT3 expression declined on day 3 after UUO injury, total STAT3 expression was still up-regulated at this point. On day 7, expression of STAT3 reached its maximum and kept this level until at least 14 days after UUO injury.

Figure 29D:
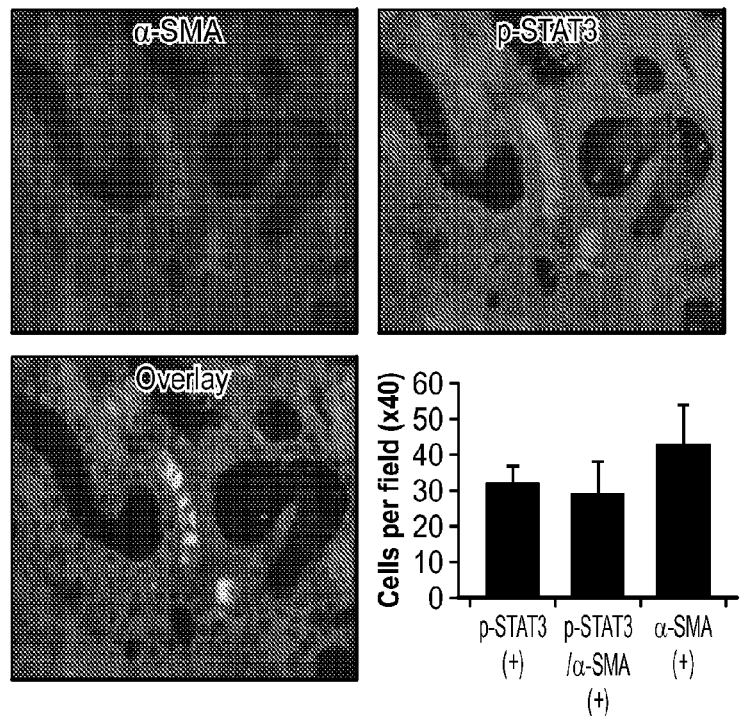

Previous work indicates that p-STAT3 is preferentially expressed in myofibroblasts in rat kidneys subjected to UUO injury. To determine whether this is also the case in the mouse model of UUO, we performed double immunostaining for α-SMA and p-STAT3 in kidney tissue after UUO injury. Most of the cells localized to the interstitium stained for both α-SMA and p-STAT3, and a small number of cells stained only for α-SMA. Cells stained only for p-STAT3 were observed only occasionally (FIG. 29D). Therefore, these data illustrate that STAT3 is preferentially activated in renal interstitial fibroblasts after UUO injury.

S3I-201 Inhibits STAT3 Phosphorylation in the Obstructive Kidney

As an initial step towards understanding the role of STAT3 in renal fibrosis, we examined the effect of S3I-201 on the expression of p-STAT3 in the kidney following obstructive injury. Contralateral kidneys were used as controls. As shown in FIG. 30, daily administration of S3I-201 at 10 mg/kg largely suppressed STAT3 phosphorylation on day 7 and a small inhibition on day 14 after UUO (FIG. 39). Total STAT3 expression was not affected by this treatment at both time points. These data indicate that UUO injury induces both activation of STAT3 and up-regulation of STAT3 protein, and that S3I-201 is an effective inhibitor of STAT3 activation without changing STAT3 protein levels. Furthermore, S3I-201 is more effective in inhibiting STAT3 activation in the early phase of obstructive nephropathy. The reason for the different effect of this inhibitor at the early and later time points is currently unknown, but may be associated with change in the signal responsible for STAT3 activation due to increased injury over time. Further studies are needed to address the mechanism that regulates STAT3 activation at different phases.

S3I-201 Attenuates Deposition of ECM Components

An increase in ECM is the major feature of renal fibrosis. To determine whether STAT3 activation is involved in the regulation of renal interstitial ECM deposition after obstructive injury, we evaluated the effect of S3I-201 on expression of interstitial collagen fibrils by Sirius red staining. An increase in Sirius red-positive areas was observed within the tubulointerstitium after UUO injury. S3I-201 treatment significantly reduced such areas (FIG. 31C, D). A semi-quantitative analysis of Sirius red-positive areas reveals a 9.5-fold increase in the obstructive kidney compared with sham-operated kidneys. Treatment with S3I-201 decreased the expression of ECM components by approximately 60% (FIG. 31E).

Figure 32A:
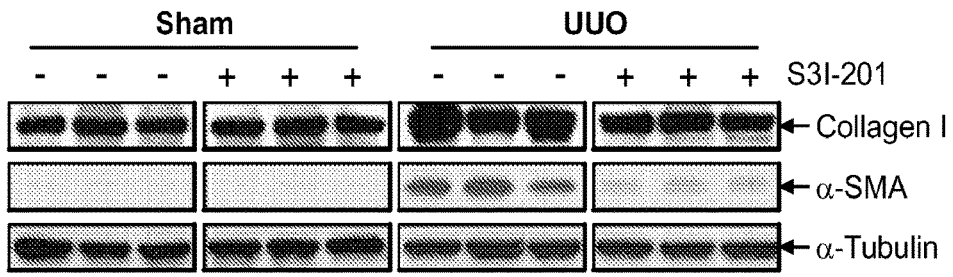
Figure 32B:
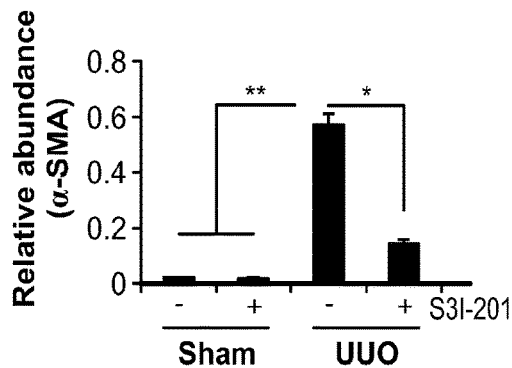
Figure 32C:
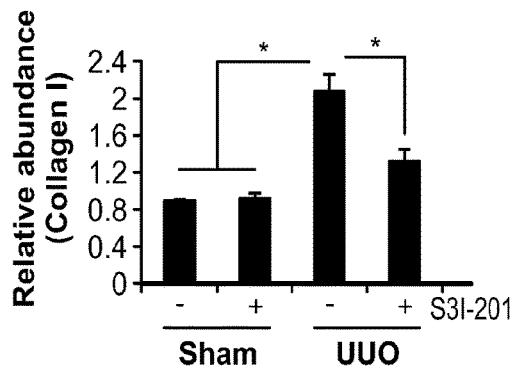
Figure 32D:
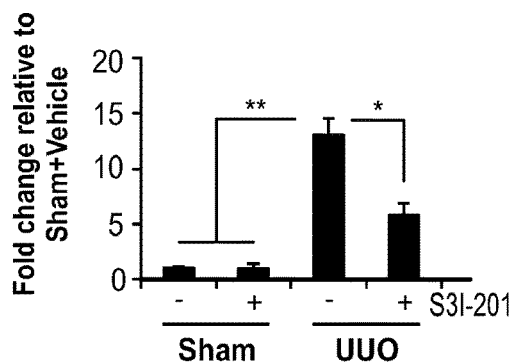

S3I-201 Inhibits Expression of Collagen Type 1 and α-SMA, but not β-Catenin and Snail After Obstructive Injury To further elucidate the role of STAT3 in fibroblast activation and production of a particular ECM protein, we examined the effect of S3I-201 on the expression of collagen type 1 and α-SMA, the hallmark of fibroblast activation, after UUO injury. As indicated in FIG. 32A, B, C, basal levels of α-SMA and abundant collagen type 1 were detected in the kidney tissue of sham-operated mice. UUO injury resulted in a marked increase in their expression. S3I-201 treatment inhibited α-SMA expression and also decreased collagen type 1 to the basal level in obstructive kidneys. Interestingly, S3I-201 did not affect the basal levels of collagen type 1 and α-SMA expression in control kidneys. In addition, we also examined the effect of S3I-201 on the expression of collagen type 1 at mRNA level and found that UUO injury also resulted in increased expression of collagen type 1 (FIG. 32D), while S3I-201 treatment attenuated this response. In contrast to those observations, administration of S3I-201 did not affect expression of β-catenin and snail (FIG. 40). Therefore, increased collagen type 1 and α-SMA after UUO injury rather than their basal levels are regulated by STAT3. Furthermore, STAT3 does not play a role in regulation of β-catenin and snail, two transcriptional regulators involved in the epithelial-mesenchymal transition.

We further examined the effect of S3I-201 on activation of renal interstitial fibroblasts on day 14 after UUO injury. S3I-201 at 10 mg/kg also decreased α-SMA and collagen type 1 expression at that time.

S3I-201 Inhibits Expression of Fibronectin after Obstructive Injury

To determine whether S3I-201 administration inhibits other ECM proteins, we assessed the effect of S3I-201 on fibronectin expression by immunostaining and immunoblot analysis. Fibronectin staining demonstrated increased expression of fibronectin after UUO injury. S3I-201 administration decreased its expression (FIG. 33A-D). Similar results were also obtained by immunoblot analysis of kidney tissue lysates (FIG. 33E). Densitometry analysis of immunoblot results showed a significant increase in the expression of fibronectin in the kidneys of mice following UUO compared with control sham-operated mice. In contrast, fibronectin expression was blocked in mice treated with S3I-201 (FIG. 33F). These data, taken together with the inhibitory effect of S3I-201 on collagen type 1 expression, suggest that STAT3 is critically involved in the production of ECM proteins after UUO injury.

S3I-201 Decreases TGF-β1 and TβRII Up-Regulation Induced by Obstructive Injury

Figure 34A:
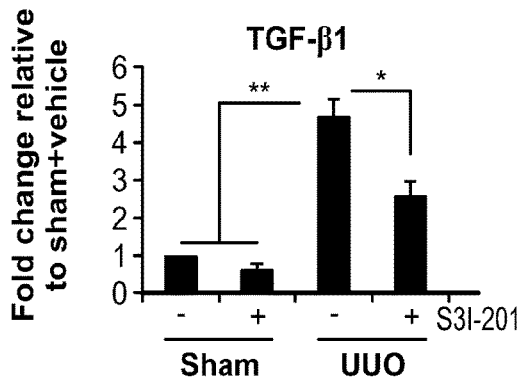
Figure 34B:
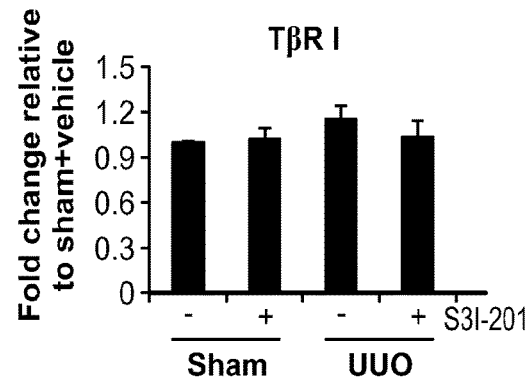
Figure 34C:
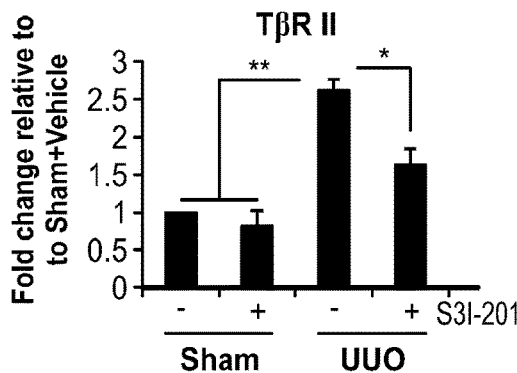
Figure 34D:
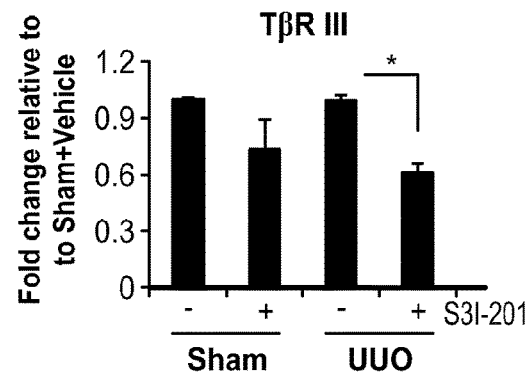
Figure 34E:
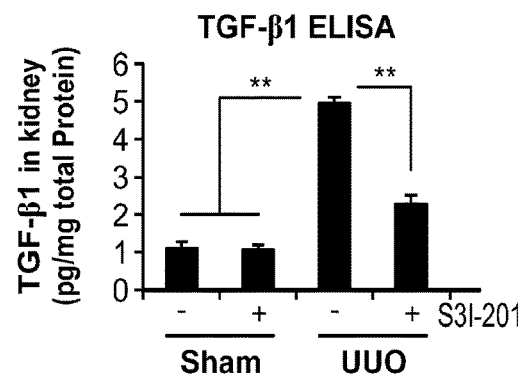
Figure 35A:
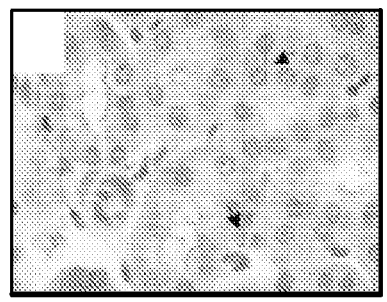
Figure 35B:
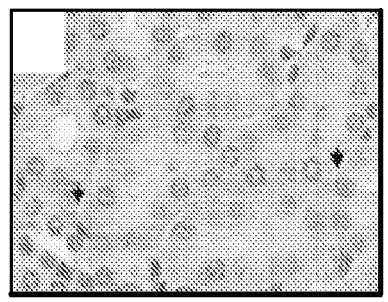
Figure 35C:
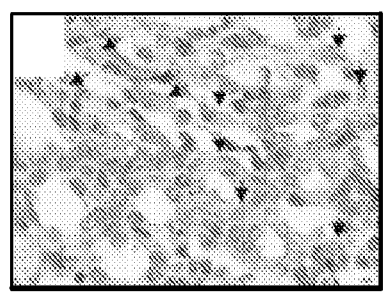
Figure 35D:
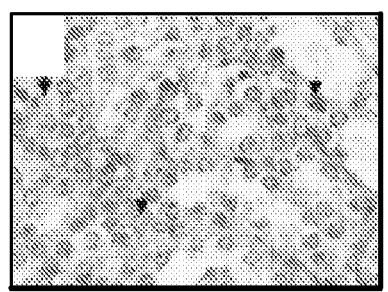
Figure 35E:
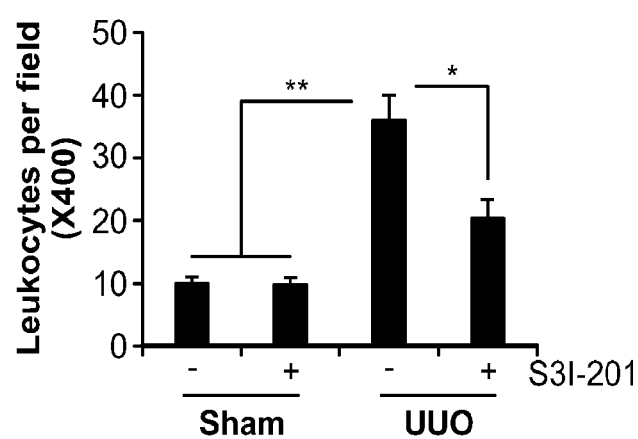

Since increased expression of TGF-β1 and/or TGF-β receptors is found in almost all forms of kidney diseases with interstitial fibrosis, we examined the effects of S3I-201 on the expression of TGF-β1 and three TGF-β receptors (type I, type II and type III) in obstructive kidneys using real-time PCR. Expression of TGF-β1 and TβRII was significantly increased in mice after obstructive injury and administration of S3I-201 reduced their levels (FIG. 34A, C). In contrast, expression levels of TβRI and TβRIII were not changed after UUO injury compared with control groups (FIG. 34B, D). S3I-201 still reduced the basal level of TβRIII, whereas TβRI expression at the basal level was not affected by this treatment. Similarly, S3I-201 significantly decreased expression of TGF-β1, TβRII, and TβRIII, but not TβRI in cultured renal interstitial fibroblasts (FIG. 38). In addition, we examined expression levels of TGF-β1 protein using the ELISA assay and demonstrated that S3I-201 also decreased expression of TGF-β1 protein in obstructive kidneys (FIG. 34E). These data indicate that STAT3 mediates expression of both TGF-β1 and its receptor, TβRII, in the obstructive kidney.

Figure 36A:
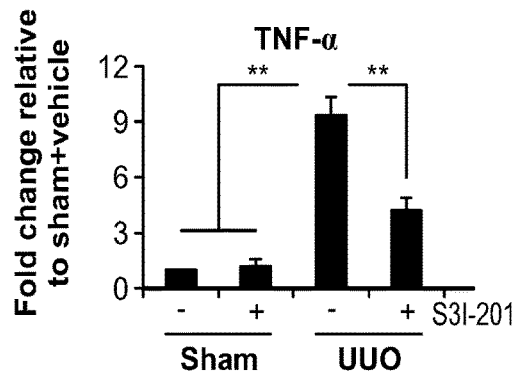
Figure 36B:
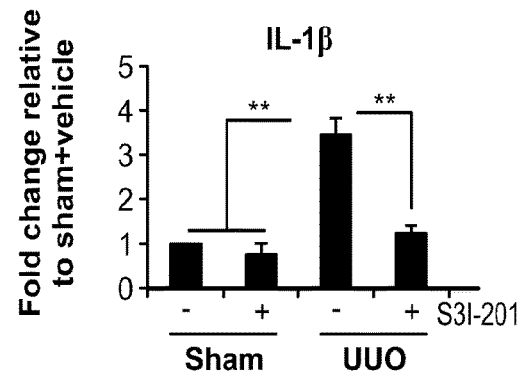
Figure 36C:
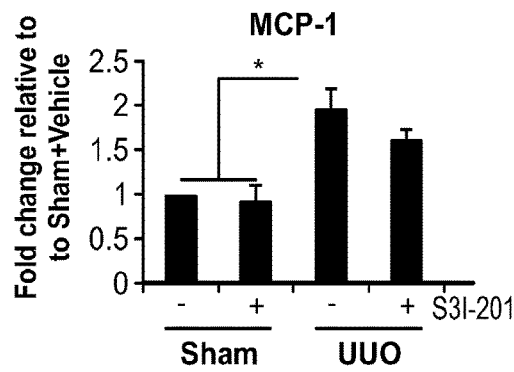
Figure 36D:
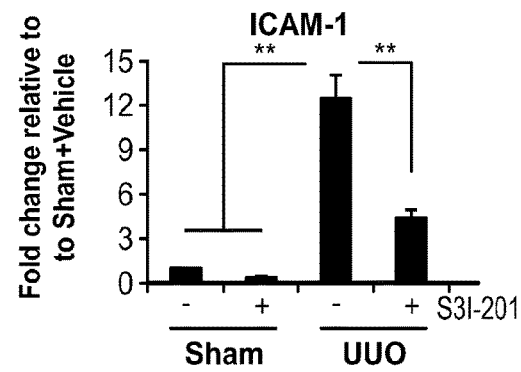
Figure 36E:
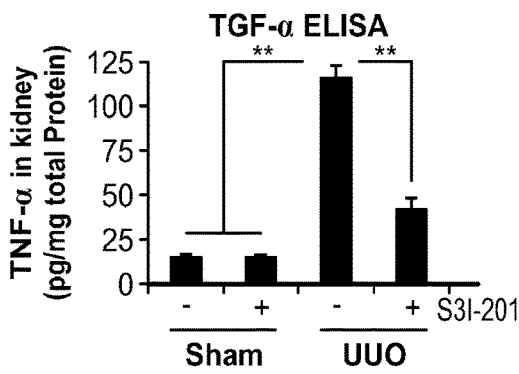
Figure 36F:
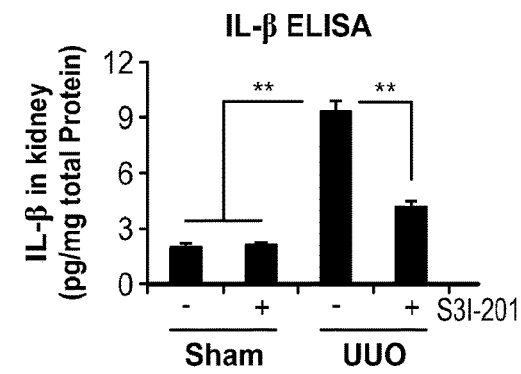

Effect of S3I-201 on Leukocyte Infiltration and Expression of Proinflammatory Cytokines after Obstructive Injury We also examined the effect of S3I-201 on leukocyte infiltration and expression of multiple pro-inflammatory cytokines, including TNF-α, IL-1β, MCP-1 and ICAM-1. Staining of kidney sections with naphthol AS-D chloroacetate esterase showed prominent interstitial infiltration of neutrophils and monocytes after obstructive injury. S3I-201 treatment reduced leukocyte infiltration to basal levels (FIG. 35). The expression levels of TNF-α, IL-1β, ICAM-1 and MCP-1 were also increased in obstructive kidneys. S3I-201 treatment reduced expression of TNF-α, IL-1β and ICAM-1 mRNA, but did not affect UUO injury-induced MCP-1 mRNA expression (FIG. 36A-D). To verify these observations, we examined the effect of S3I-201 on the expression of TNF-α and IL-1β proteins using the ELISA assay. S3I-201 also significantly suppressed their expression at the protein levels (FIG. 36E, F). These data suggest that STAT3 activity contributes to leukocyte infiltration and is selectively involved in the production of pro-inflammatory cytokines in UUO-induced renal fibrosis.

Effect of S3I-201 on Proliferation and Apoptosis of Renal Interstitial Fibroblasts after Obstructive Injury We further examined the effect of S3I-201 on apoptosis and proliferation of renal interstitial fibroblasts after UUO injury using the TUNEL assay and by evaluating cells for phospho-histone (Ser-10) positivity, respectively. Phosphorylation of histone H3 at this site specifically mark cells undergoing mitosis. As shown in FIGS. 41 and 42, animals with UUO injury displayed a greater number of TUNEL-positive and p-histone H3-positive cells, predominantly in the renal interstitium. S3I-201 treatment resulted in increased apoptosis of interstitial cells and decreased their proliferation. S3I-201 administration did not induce apoptosis of renal tubular cells (FIG. 41B). These data illustrate that UUO injury-induced STAT3 activation contributes to survival and proliferation of interstitial cells, most probably renal interstitial fibroblasts.

Inhibition of the STAT3 Prevents the Development of Nephropathy and Attenuate the Progression of Renal Fibrosis Using S3I-201, a selective inhibitor of STAT3, we provided evidence that STAT3 activity is necessary for the activation and proliferation of renal interstitial fibroblasts and the destruction of the kidney. We have shown that S3I-201 treatment inhibits the expression of α-SMA and interstitial ECM proteins, decreases proliferation of renal interstitial fibroblasts, attenuates progression of renal fibrosis, and suppresses infiltration of leukocytes and expression of multiple inflammatory cytokines in obstructive nephropathy.

We observed that UUO injury induces STAT3 phosphorylation at Tyr705 in the fibrotic mouse kidney, as early as day 1, reaching a maximum level at day 7 and remaining elevated for 14 days after UUO injury. Further immunohistochemical analysis localized p-STAT3 in most tubulointerstitial cells expressing α-SMA (FIG. 29). These observations indicate that p-STAT3 preferentially co-localizes with α-SMA in the tubulointerstitium in the rat kidney. The marked and persistent increase in activated STAT3 in the interstitial cells of fibrotic kidney suggests the importance of STAT3 in mediating activation of renal interstitial fibroblasts and progression of renal fibrosis following UUO injury. Indeed, inactivation of STAT3 by S3I-201 significantly attenuated the pathogenesis of renal fibrosis as described above. Furthermore, inhibition of STAT3 with either S3I-201 or its specific siRNA blocked the expression of α-SMA and fibronectin in cultured renal interstitial fibroblasts (FIGS. 27A-D and 28A-B).

STAT3 activation can be induced by multiple growth factors and cytokines such as TGF-β1, PDGF, and IL-6, that contribute to the development of renal fibrosis, and increased expression of activated STAT3 was detected in several kidney diseases associated with progressive fibrosis, including glomerularnephritis and diabetic nephropathy. These data indicate that STAT3 acts as a common mediator in chronic renal damage. Consistent with our observations on the profibrotic role of STAT3 in the kidney, hyperactivated STAT3 is associated with chemically-induced liver fibrosis and scar formation after spinal cord injury.

Inhibition of STAT3 activation elicits an anti-fibrotic effect by multiple mechanisms. Since TGF-β1 signaling plays a central role in a variety of fibrogenic processes such as fibroblast activation, and STAT3 is a known transcription factor, we examined the effect of S3I-201 on the expression of TGF-β1 and TGF-β receptors in the kidney after UUO. Our results indicated that expression levels of TGF-β1 and TβRII mRNA were up-regulated in the obstructed kidney, and S3I-201 treatment suppressed their expression (FIG. 34A, C). Furthermore, treatment with S3I-201 also suppressed the expression of TGF-β1 protein in the obstructed kidney (FIG. 34E). Thus, we suggest that S3I-201-elicited inhibition of myofibroblast activation is likely mediated by antagonizing TGF-β1 signaling through suppression of TGF-β1 and TβRII expression. Two potential STAT3-binding sites have been reported to exist in the promoter region of TGF-β1, and STAT3 activates promoter activity in vitro, suggesting that STAT3 may directly regulate TGF-β1 gene expression.

Progression of renal fibrosis is closely associated with the inflammatory response. We observed that administration of S3I-201 inhibited infiltration of neutrophils and monocytes and suppressed the expression of TNF-α, IL-1β, and ICAM-1, but not MCP-1, in the obstructed kidney. These results suggest that inhibition of inflammatory responses may be another mechanism by which S3I-201 attenuates renal fibrosis. Since MCP-1 is a chemokine for monocytes, we also suggest that STAT3 may induce monocyte infiltration into sites of injury in the kidney through a mechanism that is not involved in MCP-1 expression. In addition to MCP-1, other chemokines such as RANTES, monocyte inflammatory protein-1α, and macrophage inflammatory protein are also associated with the progression of renal fibrosis. Thus, STAT3 is useful to diminish or reduce monocyte infiltration by reducing expression of those chemokines.

S3I-201 is a selective and potent inhibitor of constitutive activation of STAT3 DNA-binding and STAT3-mediated gene expression. Unlike other commonly used STAT3 inhibitors such as AG490, which acts on JAKs, the upstream activators of STAT3 and other STAT isoforms S3I-201 inhibits STAT3-STAT3 complex formation, and STAT3 DNA-binding and transcriptional activities in cells that contain constitutively activated STAT3 without acting on JAKS. By binding to STAT3, S3I-201 may also prevent STAT3 protein from binding to the pTyr motifs of the receptor tyrosine kinases and subsequently block de novo phosphorylation by tyrosine kinases. These properties are very important for treatment of renal fibrosis since recent studies using knockout mice showed that in contrast to STAT3, STAT1 and STAT5 play a role in abrogating liver and lung fibrosis after injury. Our results showed that S3I-201, at the concentration that blocked STAT3 phosphorylation, increased expression of p-STAT1 but did not affect that of p-STAT5 in NRK-49F cells (FIG. 37), suggesting that the resultant increased expression of p-STAT1 and preservation of p-STAT5 in renal interstitial fibroblasts after STAT3 inhibition may also be important for attenuating the progression of tissue fibrosis.

The expanded population of fibroblasts in the diseased kidney could result from an increase in proliferation and/or a decrease in cell death. Our results showed that administration of S3I-201 inhibited proliferation and promoted death in renal interstitial cells at day 7 after UUO injury (FIGS. 41 and 42). In view of the fact that most of those cells are expressed with both α-SMA and STAT3 as shown in FIG. 29D, we suggest that STAT3 may also mediate the progression of renal fibrosis through increasing survival and proliferation of renal interstitial fibroblasts. Consequently, inhibition of STAT3-mediated renal interstitial fibroblast proliferation and survival would be additional mechanisms for alleviating the development of renal interstitial fibrosis.

In summary, our results clearly show that inhibition of STAT3 with S3I-201 can suppress activation and proliferation, and induce death of renal interstitial fibroblasts. Furthermore, S3I-301 treatment inhibits excessive deposition of ECM and transcriptional expression of TGF-β1, TβRII and several pro-inflammatory cytokines that are associated with progressive kidney diseases. Therefore, selective inhibition of the STAT3 signaling pathway is useful to prevent the development of nephropathy and attenuate the progression of renal fibrosis.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A method of treating or alleviating symptoms of chronic kidney disease in a subject who has chronic kidney disease, comprising administering to said subject a suramin compound having the structure:

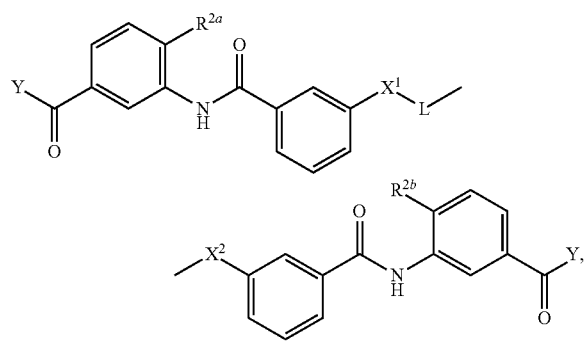

or a pharmaceutically acceptable salt, solvate, or prodrug thereof, wherein
$X^1$ and $X^2$ are each NH,
L is CO,
$R^{2a}=R^{2b}$, and are each $C_1$-$C_6$ alkyl,
Y is selected from:

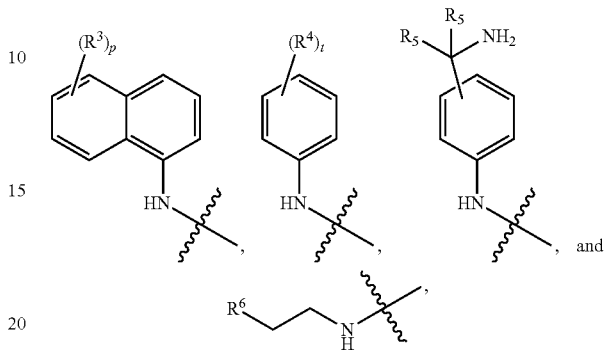

$R^3$, $R^4$, $R^5$, and $R^6$ are independently selected from $SO_3H$, $OPO_3H_2$, OH, $C_1$-$C_6$ alkyl, $C_1$-$C_6$ alkoxy, halogen, $NO_2$, $NH_2$, $CH_2F$, $CHF_2$, $CF_3$, $OCH_2F$, $OCHF_2$, and $OCF_3$, p is selected from 0, 1, 2, 3, 4, 5, 6, and 7, and t is selected from 0, 1, 2, 3, 4, and 5;

wherein said symptoms of chronic kidney disease comprise renal fibrosis and glomerulosclerosis.

2. The method of claim 1, wherein said renal fibrosis comprises tubulointerstitial fibrosis.

3. The method of claim 1, wherein said subject has an obstructive nephropathy.

4. The method of claim 1, wherein said compound is administered at the time of renal injury.

5. The method of claim 1, wherein said compound is administered after establishment of tubulointerstitial fibrosis.

6. The method of claim 1, wherein said compound is administered weekly or biweekly.

7. The method of claim 1, wherein said subject has not been diagnosed with cancer.

8. The method of claim 1, wherein said subject has been diagnosed as suffering from Stage 3 chronic kidney disease.

9. The method of claim 1, wherein said subject has been diagnosed as suffering from Stage 4 chronic kidney disease.

10. The method of claim 1, wherein said subject has been diagnosed as suffering from Stage 5 chronic kidney disease.

11. The method of claim 1, wherein said subject has been diagnosed as suffering from an autoimmune disorder.

12. The method of claim 11, wherein said autoimmune disorder is selected from systemic lupus erythematosus and scleroderma.

13. The method of claim 1, wherein said subject has been diagnosed as suffering from polycystic kidney disease.

14. The method of claim 1, wherein said subject has been diagnosed as suffering from glomerulonephritis.

15. The method of claim 1, wherein said subject has been diagnosed as suffering from kidney stones or a kidney infection.

16. The method of claim 1, wherein said suramin compound has the structure of:

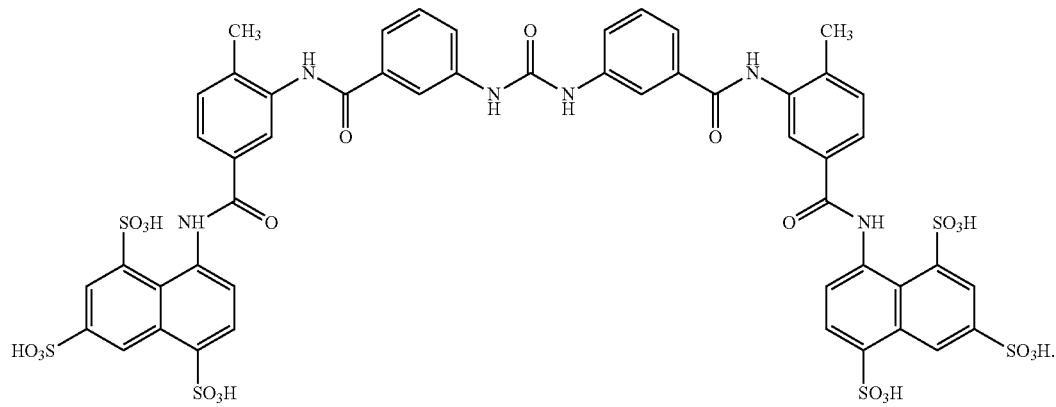 [SMILES: Cc1ccc(C(=O)Nc2ccc(S(=O)(=O)O)c3cc(S(=O)(=O)O)cc(S(=O)(=O)O)c23)cc1NC(=O)c1cccc(NC(=O)Nc2cccc(C(=O)Nc3cc(C(=O)Nc4ccc(S(=O)(=O)O)c5cc(S(=O)(=O)O)cc(S(=O)(=O)O)c45)ccc3C)c2)c1]
17. The method of claim 1, wherein said subject is a human.
18. The method of claim 5, wherein said subject has been diagnosed as suffering from reflux nephropathy.
19. The method of claim 10, wherein said subject's kidney function improves by at least 15% following administration of said suramin compound.
* * * * *